United States Patent
Li et al.

(10) Patent No.: US 12,419,304 B2
(45) Date of Patent: *Sep. 23, 2025

(54) ARYL SULFIDE COMPRISING BENZYLAMINE, SYNTHESIS METHOD AND APPLICATION THEREOF

(71) Applicant: Shandong Kangqiao Bio-Technology Co., Ltd., Binzhou (CN)

(72) Inventors: Ning Li, Binzhou (CN); Yingshuai Liu, Binzhou (CN); Xianjiang Li, Binzhou (CN); Jian Xiao, Binzhou (CN); Xiangwei Liu, Binzhou (CN); Ruibin Liu, Binzhou (CN); Guozhu Sheng, Binzhou (CN); Ruijie Feng, Binzhou (CN); Xiaozhong Xiang, Binzhou (CN); Yingrui Cui, Binzhou (CN); Yu Chen, Binzhou (CN); Shiling Wang, Binzhou (CN)

(73) Assignee: SHANDONG KANGQIAO BIO-TECHNOLOGY CO., LTD., Binzhou (CN)

( * ) Notice: Subject to any disclaimer, the term of this patent is extended or adjusted under 35 U.S.C. 154(b) by 1056 days.

This patent is subject to a terminal disclaimer.

(21) Appl. No.: 17/397,984

(22) Filed: Aug. 9, 2021

(65) Prior Publication Data

US 2021/0360919 A1 Nov. 25, 2021

Related U.S. Application Data

(63) Continuation-in-part of application No. PCT/CN2020/000198, filed on Aug. 31, 2020.

(30) Foreign Application Priority Data

Sep. 23, 2019 (CN) .......................... 201910900234.4
Aug. 10, 2020 (CN) .......................... 202010796915.3

(51) Int. Cl.
| | |
|---|---|
| *A01N 41/10* | (2006.01) |
| *A01N 33/10* | (2006.01) |
| *A01N 33/18* | (2006.01) |
| *A01N 37/34* | (2006.01) |
| *A01N 37/44* | (2006.01) |
| *A01P 7/02* | (2006.01) |
| *C07C 317/36* | (2006.01) |
| *C07C 319/14* | (2006.01) |
| *C07C 323/36* | (2006.01) |

(52) U.S. Cl.
CPC ............. *A01N 41/10* (2013.01); *A01N 33/10* (2013.01); *A01N 33/18* (2013.01); *A01N 37/34* (2013.01); *A01N 37/44* (2013.01); *A01P 7/02* (2021.08); *C07C 317/36* (2013.01); *C07C 319/14* (2013.01); *C07C 323/36* (2013.01)

(58) Field of Classification Search
CPC ........ A01N 33/10; A01N 33/18; A01N 37/34; A01N 37/44; A01N 41/10; C07C 317/36; C07C 319/14; C07C 323/36; Y02A 40/20; A01P 7/02

See application file for complete search history.

(56) References Cited

U.S. PATENT DOCUMENTS

| | | | | |
|---|---|---|---|---|
| 4,339,461 A | * | 7/1982 | King | A01N 41/10 564/384 |
| 2015/0119426 A1 | * | 4/2015 | Marugan | C07C 257/18 514/447 |
| 2024/0138408 A1 | * | 5/2024 | Li | A01P 3/00 |

FOREIGN PATENT DOCUMENTS

WO WO-2018015852 A1 * 1/2018 .............. A61P 33/14

OTHER PUBLICATIONS

Tetrahedron Letters, 2016, 57, pp. 5872-5876. (Year: 2016).*
PubChem CID 29286743 (May 28, 2009) (Year: 2009).*
PubChem CID 28437015 (May 28, 2009). (Year: 2009).*
Pang et al. Journal of Molecular Catalysis (China) vol. 31, No. Apr. 2, 2017 pp. 105-116. (Year: 2017).*

* cited by examiner

*Primary Examiner* — Kara R. Mcmillian
(74) *Attorney, Agent, or Firm* — MATTHIAS SCHOLL P.C.; Matthias Scholl

(57) ABSTRACT

The invention belongs to the technical field of pesticides and specifically relates to an aryl sulfide containing a benzylamine structure, a synthesis method therefor, and an application thereof. The aryl sulfide is denoted as compound I. Also provided is an agriculturally acceptable salt of the aryl sulfide. The compound represented by formula I shows excellent effects on various harmful organisms, especially spider mites represented by *Tetranychus cinnabarinus, Tetranychus urticae, Tetranychus Kanzawai Kishida, Panonychus citri*, etc., and can be used for controlling all kinds of harmful mites.

3 Claims, No Drawings

ARYL SULFIDE COMPRISING BENZYLAMINE, SYNTHESIS METHOD AND APPLICATION THEREOF

CROSS-REFERENCE TO RELATED APPLICATIONS

This application is a continuation-in-part of International Patent Application No. PCT/CN2020/000198 with an international filing date of Aug. 31, 2020, designating the United States, now pending, and further claims foreign priority benefits to Chinese Patent Application No. 201910900234.4 filed Sep. 23, 2019, and to Chinese Patent Application No. 202010796915.3 filed Aug. 10, 2020. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to the field of pesticides, and more particularly to an aryl sulfide comprising benzylamine, a synthesis method and application thereof.

The compound with the following general formula has acaricidal activity:

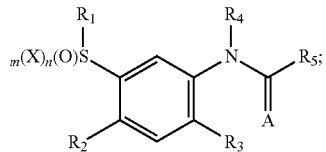

where A is oxygen or sulfur, $R_5$ is a substituted or unsubstituted $C_{1-20}$ alkyl, substituted or unsubstituted amino, nitrogen heterocycle, etc.

The following general formula compound exhibits acaricidal activity:

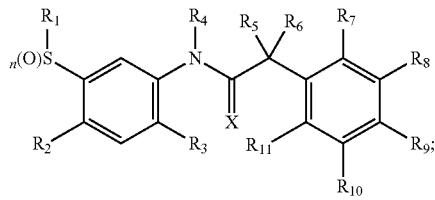

where R4 represents hydrogen, formyl, $C_{1-6}$ alkyl, or the like; $R_5$ and $R_6$ are the same or different and at each occurrence represent hydrogen, halogen, $C_{1-6}$ alkyl, or the like; $R_7$, $R_8$, $R_9$, $R_{10}$, $R_{11}$ are the same or different and at each occurrence represents hydrogen, halogen, or the like; X is oxygen or sulfur.

The active compounds mentioned above have low activity in the control of harmful substances, especially mites. Particularly, in the low usage dose, the acaricidal activity thereof is unsatisfactory, and the control effect on the drug-resistant *Tetranychus* is poor.

SUMMARY

In view of the low acaricidal activity for mite control in the prior art, the disclosure provides an aryl sulfide comprising benzylamine and its synthesis method and application. The results showed that the aryl sulfide derivatives represented by the following general formula showed excellent effects on various pests, especially on *Tetranychus cinnabarinus, Tetranychus urticae, Tetranychus kanzawai, Panonychus citri*, and the like.

The disclosure provides an aryl sulfide comprising benzylamine, being represented by formula I, or an agriculturally acceptable salt thereof:

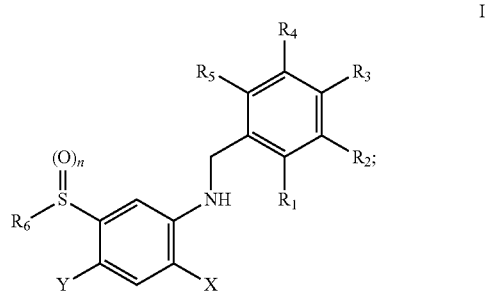

where:

n is 0, 1 or 2;

X and Y at each occurrence represent hydrogen, fluorine, chlorine, bromine, iodine, a cyano group, a $C_{1-4}$ alkyl, a $C_{1-4}$ haloalkyl, a $C_{1-4}$ alkoxy or a $C_{1-4}$ haloalkoxy;

$R_1$, $R_2$, $R_3$, $R_4$, and $R_5$ at each occurrence represent hydrogen, fluorine, chlorine, bromine, iodine, a cyano group, nitro, amino, hydroxymethyl, carboxyl, hydroxyl, sulphydryl, $C_{1-10}$ alkyl, $C_{1-10}$ haloalkyl, $C_{1-10}$ alkoxy, $C_{1-10}$ haloalkoxy, $C_{1-10}$ alkoxycarbonyl, $C_{1-10}$ haloalkoxycarbonyl, $C_{1-10}$ alkylsulfonyloxy, $C_{1-10}$ alkyl sulfonyl, $C_{1-10}$ alkylthiol, $C_{1-10}$ haloalkylthiol, $C_{2-10}$ ethoxycarbonyl, $C_{1-10}$ alkyl carbonyl, amino carbonyl, $C_{1-10}$ N-alkyl carbonyl, N, N-dimethylcarbonyl, N, N-dimethylthiocarbonyl, $C_{1-10}$ N-alkyl thiocarbonyl, 2-oxoprooxycarbonyl, or methoxymethoxycarbonyl; and $R_6$ represents $C_{1-6}$ haloalkyl, $C_{2-6}$ alkynyl, $C_{2-6}$ alkenyl, $C_{1-6}$ alkyl, $C_{3-6}$ cycloalkyl, or $C_{3-6}$ epoxy alkyl.

In a class of this embodiment, in formula I, n is 0 or 1;

X is fluorine, chlorine, or methyl;

Y is chlorine or methyl;

$R_1$ is hydrogen, fluorine, chlorine, bromine, hydroxyl, nitro, hydroxymethyl, a cyano group, trifluoromethyl, $C_{1-3}$ alkyl, $C_{1-4}$ alkoxycarbonyl, acetyl, propionyl, $C_{1-3}$ alkoxy, ethylthio, 2-fluoroethanothioxy, 2-chloroethanothioxy, 2,2-difluoroethylthio, 2,2,2-trifluoroethylthio, propylthio, 2,2,2-trifluoroethylsulfinyl, vinyloxycarbonyl, 2,2,2-trifluoroethoxycarbonyl, or N-methylcarbonyl;

$R_2$ is hydrogen, fluorine, or chlorine;

$R_3$ is hydrogen, fluorine, chlorine, bromine, or a cyano group;

$R_4$ and $R_5$ at each occurrence represent hydrogen; and $R_6$ is N-propyl or 2,2,2-trifluoroethyl.

In a class of this embodiment, in formula I, n is 0 or 1;

X is fluorine;

Y is chlorine or methyl;

$R_1$ is methoxycarbonyl, ethoxycarbonyl, ethylthio, or 2,2,2-trifluoroethylthio;

$R_2$, $R_4$, and $R_5$ at each occurrence represent hydrogen;

$R_3$ is hydrogen, fluorine, chlorine, or a cyano group; and $R_6$ is 2,2,2-trifluoroethyl.

In a class of this embodiment, the formula I comprises:

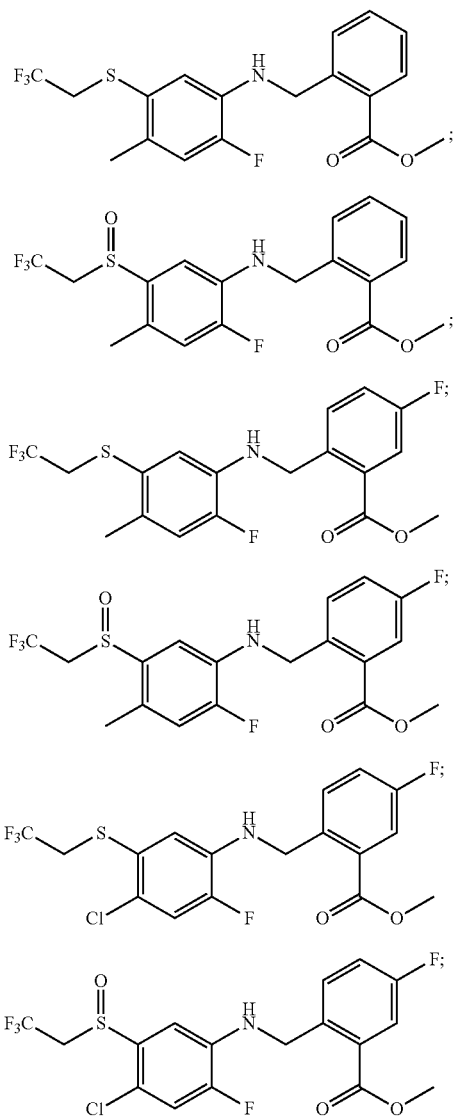

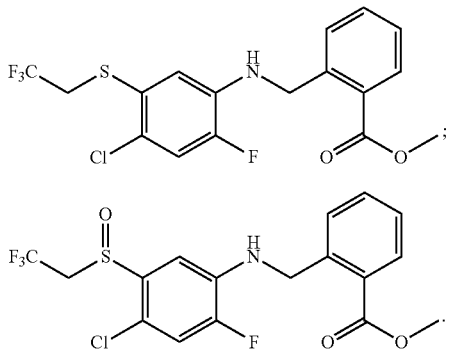

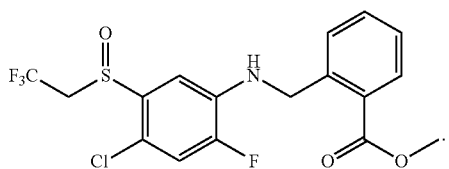

Representative compounds of the general formula I of the disclosure are shown in Table 1. However, the compounds of the disclosure are not limited to those listed therein. In addition, the serial numbers of corresponding compounds are also listed in Table 1.

According to the type of substituents, the compounds of the aryl sulfide derivatives and aryl sulfur oxide derivatives of the disclosure present in the form of E-type and Z-type geometric isomers, and the compounds of the disclosure comprise the E-type, Z-type or a mixture thereof in an arbitrary proportion.

The following abbreviations in Table 1 denote the following groups respectively:

Me: methyl;
Et: ethyl;
tBu: tert butyl;
$CF_3$: trifluoromethyl;
AC: acetyl group;
nPropyl: n-propyl;
isopropyl: Isopropyl;
nButyl: n-butyl;
nPentyl: n-amyl;
nHexyl: n-hexyl;
nHeptyl: n-heptyl;
nOctyl: n-octyl;
nNonyl: nonyl;
nDecyl: n-decyl.

TABLE 1

List of compounds

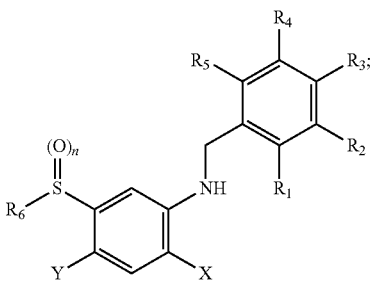

I

| No. | X | Y | n | $R_1$ | $R_2$ | $R_3$ | $R_4$ | $R_5$ | $R_6$ |
|---|---|---|---|---|---|---|---|---|---|
| 1 | F | Me | 0 | Me | H | H | H | H | $CH_2CF_3$ |
| 2 | F | Me | 1 | Me | H | H | H | H | $CH_2CF_3$ |
| 3 | F | Me | 0 | $CF_3$ | H | H | H | H | $CH_2CF_3$ |
| 4 | F | Me | 1 | $CF_3$ | H | H | H | H | $CH_2CF_3$ |

TABLE 1-continued

List of compounds

I $$\text{structure with } R_4, R_5, R_3, R_2, R_1, \text{NH}, (O)_n, S, R_6, Y, X$$

| No. | X | Y | n | R$_1$ | R$_2$ | R$_3$ | R$_4$ | R$_5$ | R$_6$ |
|---|---|---|---|---|---|---|---|---|---|
| 5 | F | Me | 0 | Et | H | H | H | H | CH$_2$CF$_3$ |
| 6 | F | Me | 1 | Et | H | H | H | H | CH$_2$CF$_3$ |
| 7 | F | Me | 0 | nPropyl | H | H | H | H | CH$_2$CF$_3$ |
| 8 | F | Me | 1 | nPropyl | H | H | H | H | CH$_2$CF$_3$ |
| 9 | F | Me | 0 | isopropyl | H | H | H | H | CH$_2$CF$_3$ |
| 10 | F | Me | 1 | isopropyl | H | H | H | H | CH$_2$CF$_3$ |
| 11 | F | Me | 0 | nButyl | H | H | H | H | CH$_2$CF$_3$ |
| 12 | F | Me | 1 | nButyl | H | H | H | H | CH$_2$CF$_3$ |
| 13 | F | Me | 0 | nPentyl | H | H | H | H | CH$_2$CF$_3$ |
| 14 | F | Me | 1 | nPentyl | H | H | H | H | CH$_2$CF$_3$ |
| 15 | F | Me | 0 | nHexyl | H | H | H | H | CH$_2$CF$_3$ |
| 16 | F | Me | 1 | nHexyl | H | H | H | H | CH$_2$CF$_3$ |
| 17 | F | Me | 0 | nHeptyl | H | H | H | H | CH$_2$CF$_3$ |
| 18 | F | Me | 1 | nHeptyl | H | H | H | H | CH$_2$CF$_3$ |
| 19 | F | Me | 0 | nOctyl | H | H | H | H | CH$_2$CF$_3$ |
| 20 | F | Me | 1 | nOctyl | H | H | H | H | CH$_2$CF$_3$ |
| 21 | F | Me | 0 | nNonyl | H | H | H | H | CH$_2$CF$_3$ |
| 22 | F | Me | 1 | nNonyl | H | H | H | H | CH$_2$CF$_3$ |
| 23 | F | Me | 0 | nDecyl | H | H | H | H | CH$_2$CF$_3$ |
| 24 | F | Me | 1 | nDecyl | H | H | H | H | CH$_2$CF$_3$ |
| 25 | F | Me | 0 | F | H | H | H | H | CH$_2$CF$_3$ |
| 26 | F | Me | 1 | F | H | H | H | H | CH$_2$CF$_3$ |
| 27 | F | Me | 0 | Cl | H | H | H | H | CH$_2$CF$_3$ |
| 28 | F | Me | 1 | Cl | H | H | H | H | CH$_2$CF$_3$ |
| 29 | F | Me | 0 | Br | H | H | H | H | CH$_2$CF$_3$ |
| 30 | F | Me | 1 | Br | H | H | H | H | CH$_2$CF$_3$ |
| 31 | F | Me | 0 | I | H | H | H | H | CH$_2$CF$_3$ |
| 32 | F | Me | 1 | I | H | H | H | H | CH$_2$CF$_3$ |
| 33 | F | Me | 0 | CN | H | H | H | H | CH$_2$CF$_3$ |
| 34 | F | Me | 1 | CN | H | H | H | H | CH$_2$CF$_3$ |
| 35 | F | Me | 0 | NO$_2$ | H | H | H | H | CH$_2$CF$_3$ |
| 36 | F | Me | 1 | NO$_2$ | H | H | H | H | CH$_2$CF$_3$ |
| 37 | F | Me | 0 | NH$_2$ | H | H | H | H | CH$_2$CF$_3$ |
| 38 | F | Me | 1 | NH$_2$ | H | H | H | H | CH$_2$CF$_3$ |
| 39 | F | Me | 0 | CH$_2$OH | H | H | H | H | CH$_2$CF$_3$ |
| 40 | F | Me | 1 | CH$_2$OH | H | H | H | H | CH$_2$CF$_3$ |
| 41 | F | Me | 0 | COCH$_3$ | H | H | H | H | CH$_2$CF$_3$ |
| 42 | F | Me | 1 | COCH$_3$ | H | H | H | H | CH$_2$CF$_3$ |
| 43 | F | Me | 0 | COCH$_2$CH$_3$ | H | H | H | H | CH$_2$CF$_3$ |
| 44 | F | Me | 1 | COCH$_2$CH$_3$ | H | H | H | H | CH$_2$CF$_3$ |
| 45 | F | Me | 0 | COCH$_2$CH$_2$CH$_3$ | H | H | H | H | CH$_2$CF$_3$ |
| 46 | F | Me | 1 | COCH$_2$CH$_2$CH$_3$ | H | H | H | H | CH$_2$CF$_3$ |
| 47 | F | Me | 0 | COCH$_2$CH$_2$CH$_2$CH$_3$ | H | H | H | H | CH$_2$CF$_3$ |
| 48 | F | Me | 1 | COCH$_2$CH$_2$CH$_2$CH$_3$ | H | H | H | H | CH$_2$CF$_3$ |
| 49 | F | Me | 0 | COCH$_2$CH$_2$CH$_2$CH$_2$CH$_3$ | H | H | H | H | CH$_2$CF$_3$ |
| 50 | F | Me | 1 | COCH$_2$CH$_2$CH$_2$CH$_2$CH$_3$ | H | H | H | H | CH$_2$CF$_3$ |
| 51 | F | Me | 0 | COOH | H | H | H | H | CH$_2$CF$_3$ |
| 52 | F | Me | 1 | COOH | H | H | H | H | CH$_2$CF$_3$ |
| 53 | F | Me | 0 | CO$_2$CH$_3$ | H | H | H | H | CH$_2$CF$_3$ |
| 54 | F | Me | 1 | CO$_2$CH$_3$ | H | H | H | H | CH$_2$CF$_3$ |
| 55 | F | Me | 0 | CO$_2$CH$_2$CH$_3$ | H | H | H | H | CH$_2$CF$_3$ |
| 56 | F | Me | 1 | CO$_2$CH$_2$CH$_3$ | H | H | H | H | CH$_2$CF$_3$ |
| 57 | F | Me | 0 | CO$_2$CH$_2$CH$_2$CH$_3$ | H | H | H | H | CH$_2$CF$_3$ |
| 58 | F | Me | 1 | CO$_2$CH$_2$CH$_2$CH$_3$ | H | H | H | H | CH$_2$CF$_3$ |
| 59 | F | Me | 0 | CO$_2$CH$_2$CH$_2$CH$_2$CH$_3$ | H | H | H | H | CH$_2$CF$_3$ |
| 60 | F | Me | 1 | CO$_2$CH$_2$CH$_2$CH$_2$CH$_3$ | H | H | H | H | CH$_2$CF$_3$ |
| 61 | F | Me | 0 | CO$_2$CH$_2$CH$_2$CH$_2$CH$_2$CH$_3$ | H | H | H | H | CH$_2$CF$_3$ |
| 62 | F | Me | 1 | CO$_2$CH$_2$CH$_2$CH$_2$CH$_2$CH$_3$ | H | H | H | H | CH$_2$CF$_3$ |
| 63 | F | Me | 0 | CO$_2$CH(CH$_3$)$_2$ | H | H | H | H | CH$_2$CF$_3$ |
| 64 | F | Me | 1 | CO$_2$CH(CH$_3$)$_2$ | H | H | H | H | CH$_2$CF$_3$ |
| 65 | F | Me | 0 | CO$_2$CH$_2$CH(CH$_3$)$_2$ | H | H | H | H | CH$_2$CF$_3$ |

TABLE 1-continued

List of compounds

I

| No. | X | Y | n | R₁ | R₂ | R₃ | R₄ | R₅ | R₆ |
|---|---|---|---|---|---|---|---|---|---|
| 66 | F | Me | 1 | CO₂CH₂CH(CH₃)₂ | H | H | H | H | CH₂CF₃ |
| 67 | F | Me | 0 | CO₂CH=CH₂ | H | H | H | H | CH₂CF₃ |
| 68 | F | Me | 1 | CO₂CH=CH₂ | H | H | H | H | CH₂CF₃ |
| 69 | F | Me | 0 | CO₂CH₂CH=CH₂ | H | H | H | H | CH₂CF₃ |
| 70 | F | Me | 1 | CO₂CH₂CH=CH₂ | H | H | H | H | CH₂CF₃ |
| 71 | F | Me | 0 | CO₂CH₂CF₃ | H | H | H | H | CH₂CF₃ |
| 72 | F | Me | 1 | CO₂CH₂CF₃ | H | H | H | H | CH₂CF₃ |
| 73 | F | Me | 0 | CO₂CH₂CH₂Cl | H | H | H | H | CH₂CF₃ |
| 74 | F | Me | 1 | CO₂CH₂CH₂Cl | H | H | H | H | CH₂CF₃ |
| 75 | F | Me | 0 | CO₂CH₂CH₂Br | H | H | H | H | CH₂CF₃ |
| 76 | F | Me | 1 | CO₂CH₂CH₂Br | H | H | H | H | CH₂CF₃ |
| 77 | F | Me | 0 | CO₂CH₂OCH₃ | H | H | H | H | CH₂CF₃ |
| 78 | F | Me | 1 | CO₂CH₂COCH₃ | H | H | H | H | CH₂CF₃ |
| 79 | F | Me | 0 | CONH₂ | H | H | H | H | CH₂CF₃ |
| 80 | F | Me | 1 | CONH₂ | H | H | H | H | CH₂CF₃ |
| 81 | F | Me | 0 | CONHCH₃ | H | H | H | H | CH₂CF₃ |
| 82 | F | Me | 1 | CONHCH₃ | H | H | H | H | CH₂CF₃ |
| 83 | F | Me | 0 | CON(CH₃)₂ | H | H | H | H | CH₂CF₃ |
| 84 | F | Me | 1 | CON(CH₃)₂ | H | H | H | H | CH₂CF₃ |
| 85 | F | Me | 0 | CONHCH₂CH₃ | H | H | H | H | CH₂CF₃ |
| 86 | F | Me | 1 | CONHCH₂CH₃ | H | H | H | H | CH₂CF₃ |
| 87 | F | Me | 0 | CONHCH₂CH₂CH₃ | H | H | H | H | CH₂CF₃ |
| 88 | F | Me | 1 | CONHCH₂CH₂CH₃ | H | H | H | H | CH₂CF₃ |
| 89 | F | Me | 0 | CONHCH₂CH₂CH₂CH₃ | H | H | H | H | CH₂CF₃ |
| 90 | F | Me | 1 | CONHCH₂CH₂CH₂CH₃ | H | H | H | H | CH₂CF₃ |
| 91 | F | Me | 0 | CONHCH₂CH₂CH₂CH₂CH₃ | H | H | H | H | CH₂CF₃ |
| 92 | F | Me | 1 | CONHCH₂CH₂CH₂CH₂CH₃ | H | H | H | H | CH₂CF₃ |
| 93 | F | Me | 0 | OH | H | H | H | H | CH₂CF₃ |
| 94 | F | Me | 1 | OH | H | H | H | H | CH₂CF₃ |
| 95 | F | Me | 0 | OCH₃ | H | H | H | H | CH₂CF₃ |
| 96 | F | Me | 1 | OCH₃ | H | H | H | H | CH₂CF₃ |
| 97 | F | Me | 0 | OCH₂CH₃ | H | H | H | H | CH₂CF₃ |
| 98 | F | Me | 1 | OCH₂CH₃ | H | H | H | H | CH₂CF₃ |
| 99 | F | Me | 0 | OCH₂CH₂CH₃ | H | H | H | H | CH₂CF₃ |
| 100 | F | Me | 1 | OCH₂CH₂CH₃ | H | H | H | H | CH₂CF₃ |
| 101 | F | Me | 0 | OCH₂CH₂CH₂CH₃ | H | H | H | H | CH₂CF₃ |
| 102 | F | Me | 1 | OCH₂CH₂CH₂CH₃ | H | H | H | H | CH₂CF₃ |
| 103 | F | Me | 0 | OCH₂CH₂CH₂CH₂CH₃ | H | H | H | H | CH₂CF₃ |
| 104 | F | Me | 1 | SH | H | H | H | H | CH₂CF₃ |
| 105 | F | Me | 0 | SH | H | H | H | H | CH₂CF₃ |
| 106 | F | Me | 1 | SCH₃ | H | H | H | H | CH₂CF₃ |
| 107 | F | Me | 0 | SCH₃ | H | H | H | H | CH₂CF₃ |
| 108 | F | Me | 1 | SCH₂CH₃ | H | H | H | H | CH₂CF₃ |
| 109 | F | Me | 0 | SCH₂CH₃ | H | H | H | H | CH₂CF₃ |
| 110 | F | Me | 1 | SCH₂CH₂CH₃ | H | H | H | H | CH₂CF₃ |
| 111 | F | Me | 0 | SCH₂CH₂CH₃ | H | H | H | H | CH₂CF₃ |
| 112 | F | Me | 1 | SCH₂CH₂CH₂CH₃ | H | H | H | H | CH₂CF₃ |
| 113 | F | Me | 0 | SCH₂CH₂CH₂CH₃ | H | H | H | H | CH₂CF₃ |
| 114 | F | Me | 1 | SCH₂CH₂CH₂CH₂CH₃ | H | H | H | H | CH₂CF₃ |
| 115 | Me | Me | 0 | Me | H | H | H | H | CH₂CF₃ |
| 116 | Me | Me | 1 | Me | H | H | H | H | CH₂CF₃ |
| 117 | Me | Me | 0 | CF₃ | H | H | H | H | CH₂CF₃ |
| 118 | Me | Me | 1 | CF₃ | H | H | H | H | CH₂CF₃ |
| 119 | Me | Me | 0 | Et | H | H | H | H | CH₂CF₃ |
| 120 | Me | Me | 1 | Et | H | H | H | H | CH₂CF₃ |
| 121 | Me | Me | 0 | nPropyl | H | H | H | H | CH₂CF₃ |
| 122 | Me | Me | 1 | nPropyl | H | H | H | H | CH₂CF₃ |
| 123 | Me | Me | 0 | isopropyl | H | H | H | H | CH₂CF₃ |
| 124 | Me | Me | 1 | isopropyl | H | H | H | H | CH₂CF₃ |
| 125 | Me | Me | 0 | nButyl | H | H | H | H | CH₂CF₃ |
| 126 | Me | Me | 1 | nButyl | H | H | H | H | CH₂CF₃ |

TABLE 1-continued

List of compounds

I

| No. | X | Y | n | $R_1$ | $R_2$ | $R_3$ | $R_4$ | $R_5$ | $R_6$ |
|---|---|---|---|---|---|---|---|---|---|
| 127 | Me | Me | 0 | nPentyl | H | H | H | H | $CH_2CF_3$ |
| 128 | Me | Me | 1 | nPentyl | H | H | H | H | $CH_2CF_3$ |
| 129 | Me | Me | 0 | nHexyl | H | H | H | H | $CH_2CF_3$ |
| 130 | Me | Me | 1 | nHexyl | H | H | H | H | $CH_2CF_3$ |
| 131 | Me | Me | 0 | nHeptyl | H | H | H | H | $CH_2CF_3$ |
| 132 | Me | Me | 1 | nHeptyl | H | H | H | H | $CH_2CF_3$ |
| 133 | Me | Me | 0 | nOctyl | H | H | H | H | $CH_2CF_3$ |
| 134 | Me | Me | 1 | nOctyl | H | H | H | H | $CH_2CF_3$ |
| 135 | Me | Me | 0 | nNonyl | H | H | H | H | $CH_2CF_3$ |
| 136 | Me | Me | 1 | nNonyl | H | H | H | H | $CH_2CF_3$ |
| 137 | Me | Me | 0 | nDecyl | H | H | H | H | $CH_2CF_3$ |
| 138 | Me | Me | 1 | nDecyl | H | H | H | H | $CH_2CF_3$ |
| 139 | Me | Me | 0 | F | H | H | H | H | $CH_2CF_3$ |
| 140 | Me | Me | 1 | F | H | H | H | H | $CH_2CF_3$ |
| 141 | Me | Me | 0 | Cl | H | H | H | H | $CH_2CF_3$ |
| 142 | Me | Me | 1 | Cl | H | H | H | H | $CH_2CF_3$ |
| 143 | Me | Me | 0 | Br | H | H | H | H | $CH_2CF_3$ |
| 144 | Me | Me | 1 | Br | H | H | H | H | $CH_2CF_3$ |
| 145 | Me | Me | 0 | I | H | H | H | H | $CH_2CF_3$ |
| 146 | Me | Me | 1 | I | H | H | H | H | $CH_2CF_3$ |
| 147 | Me | Me | 0 | CN | H | H | H | H | $CH_2CF_3$ |
| 148 | Me | Me | 1 | CN | H | H | H | H | $CH_2CF_3$ |
| 149 | Me | Me | 0 | $NO_2$ | H | H | H | H | $CH_2CF_3$ |
| 150 | Me | Me | 1 | $NO_2$ | H | H | H | H | $CH_2CF_3$ |
| 151 | Me | Me | 0 | $NH_2$ | H | H | H | H | $CH_2CF_3$ |
| 152 | Me | Me | 1 | $NH_2$ | H | H | H | H | $CH_2CF_3$ |
| 153 | Me | Me | 0 | $CH_2OH$ | H | H | H | H | $CH_2CF_3$ |
| 154 | Me | Me | 1 | $CH_2OH$ | H | H | H | H | $CH_2CF_3$ |
| 155 | Me | Me | 0 | $COCH_3$ | H | H | H | H | $CH_2CF_3$ |
| 156 | Me | Me | 1 | $COCH_3$ | H | H | H | H | $CH_2CF_3$ |
| 157 | Me | Me | 0 | $COCH_2CH_3$ | H | H | H | H | $CH_2CF_3$ |
| 158 | Me | Me | 1 | $COCH_2CH_3$ | H | H | H | H | $CH_2CF_3$ |
| 159 | Me | Me | 0 | $COCH_2CH_2CH_3$ | H | H | H | H | $CH_2CF_3$ |
| 160 | Me | Me | 1 | $COCH_2CH_2CH_3$ | H | H | H | H | $CH_2CF_3$ |
| 161 | Me | Me | 0 | $COCH_2CH_2CH_2CH_3$ | H | H | H | H | $CH_2CF_3$ |
| 162 | Me | Me | 1 | $COCH_2CH_2CH_2CH_3$ | H | H | H | H | $CH_2CF_3$ |
| 163 | Me | Me | 0 | $COCH_2CH_2CH_2CH_2CH_3$ | H | H | H | H | $CH_2CF_3$ |
| 164 | Me | Me | 1 | $COCH_2CH_2CH_2CH_2CH_3$ | H | H | H | H | $CH_2CF_3$ |
| 165 | Me | Me | 0 | COOH | H | H | H | H | $CH_2CF_3$ |
| 166 | Me | Me | 1 | COOH | H | H | H | H | $CH_2CF_3$ |
| 167 | Me | Me | 0 | $CO_2CH_3$ | H | H | H | H | $CH_2CF_3$ |
| 168 | Me | Me | 1 | $CO_2CH_3$ | H | H | H | H | $CH_2CF_3$ |
| 169 | Me | Me | 0 | $CO_2CH_2CH_3$ | H | H | H | H | $CH_2CF_3$ |
| 170 | Me | Me | 1 | $CO_2CH_2CH_3$ | H | H | H | H | $CH_2CF_3$ |
| 171 | Me | Me | 0 | $CO_2CH_2CH_2CH_3$ | H | H | H | H | $CH_2CF_3$ |
| 172 | Me | Me | 1 | $CO_2CH_2CH_2CH_3$ | H | H | H | H | $CH_2CF_3$ |
| 173 | Me | Me | 0 | $CO_2CH_2CH_2CH_2CH_3$ | H | H | H | H | $CH_2CF_3$ |
| 174 | Me | Me | 1 | $CO_2CH_2CH_2CH_2CH_3$ | H | H | H | H | $CH_2CF_3$ |
| 175 | Me | Me | 0 | $CO_2CH_2CH_2CH_2CH_2CH_3$ | H | H | H | H | $CH_2CF_3$ |
| 176 | Me | Me | 1 | $CO_2CH_2CH_2CH_2CH_2CH_3$ | H | H | H | H | $CH_2CF_3$ |
| 177 | Me | Me | 0 | $CO_2CH(CH_3)_2$ | H | H | H | H | $CH_2CF_3$ |
| 178 | Me | Me | 1 | $CO_2CH(CH_3)_2$ | H | H | H | H | $CH_2CF_3$ |
| 179 | Me | Me | 0 | $CO_2CH_2CH(CH_3)_2$ | H | H | H | H | $CH_2CF_3$ |
| 180 | Me | Me | 1 | $CO_2CH_2CH(CH_3)_2$ | H | H | H | H | $CH_2CF_3$ |
| 181 | Me | Me | 0 | $CO_2CH=CH_2$ | H | H | H | H | $CH_2CF_3$ |
| 182 | Me | Me | 1 | $CO_2CH=CH_2$ | H | H | H | H | $CH_2CF_3$ |
| 183 | Me | Me | 0 | $CO_2CH_2CH=CH_2$ | H | H | H | H | $CH_2CF_3$ |
| 184 | Me | Me | 1 | $CO_2CH_2CH=CH_2$ | H | H | H | H | $CH_2CF_3$ |
| 185 | Me | Me | 0 | $CO_2CH_2CF_3$ | H | H | H | H | $CH_2CF_3$ |
| 186 | Me | Me | 1 | $CO_2CH_2CF_3$ | H | H | H | H | $CH_2CF_3$ |
| 187 | Me | Me | 0 | $CO_2CH_2CH_2Cl$ | H | H | H | H | $CH_2CF_3$ |

TABLE 1-continued

List of compounds

I

| No. | X | Y | n | R$_1$ | R$_2$ | R$_3$ | R$_4$ | R$_5$ | R$_6$ |
|---|---|---|---|---|---|---|---|---|---|
| 188 | Me | Me | 1 | CO$_2$CH$_2$CH$_2$Cl | H | H | H | H | CH$_2$CF$_3$ |
| 189 | Me | Me | 0 | CO$_2$CH$_2$CH$_2$Br | H | H | H | H | CH$_2$CF$_3$ |
| 190 | Me | Me | 1 | CO$_2$CH$_2$CH$_2$Br | H | H | H | H | CH$_2$CF$_3$ |
| 191 | Me | Me | 0 | CO$_2$CH$_2$OCH$_3$ | H | H | H | H | CH$_2$CF$_3$ |
| 192 | Me | Me | 1 | CO$_2$CH$_2$COCH$_3$ | H | H | H | H | CH$_2$CF$_3$ |
| 193 | Me | Me | 0 | CONH$_2$ | H | H | H | H | CH$_2$CF$_3$ |
| 194 | Me | Me | 1 | CONH$_2$ | H | H | H | H | CH$_2$CF$_3$ |
| 195 | Me | Me | 0 | CONHCH$_3$ | H | H | H | H | CH$_2$CF$_3$ |
| 196 | Me | Me | 1 | CONHCH$_3$ | H | H | H | H | CH$_2$CF$_3$ |
| 197 | Me | Me | 0 | CON(CH$_3$)$_2$ | H | H | H | H | CH$_2$CF$_3$ |
| 198 | Me | Me | 1 | CON(CH$_3$)$_2$ | H | H | H | H | CH$_2$CF$_3$ |
| 199 | Me | Me | 0 | CONHCH$_2$CH$_3$ | H | H | H | H | CH$_2$CF$_3$ |
| 200 | Me | Me | 1 | CONHCH$_2$CH$_3$ | H | H | H | H | CH$_2$CF$_3$ |
| 201 | Me | Me | 0 | CONHCH$_2$CH$_2$CH$_3$ | H | H | H | H | CH$_2$CF$_3$ |
| 202 | Me | Me | 1 | CONHCH$_2$CH$_2$CH$_3$ | H | H | H | H | CH$_2$CF$_3$ |
| 203 | Me | Me | 0 | CONHCH$_2$CH$_2$CH$_2$CH$_3$ | H | H | H | H | CH$_2$CF$_3$ |
| 204 | Me | Me | 1 | CONHCH$_2$CH$_2$CH$_2$CH$_3$ | H | H | H | H | CH$_2$CF$_3$ |
| 205 | Me | Me | 0 | CONHCH$_2$CH$_2$CH$_2$CH$_2$CH$_3$ | H | H | H | H | CH$_2$CF$_3$ |
| 206 | Me | Me | 1 | CONHCH$_2$CH$_2$CH$_2$CH$_2$CH$_3$ | H | H | H | H | CH$_2$CF$_3$ |
| 207 | Me | Me | 0 | OH | H | H | H | H | CH$_2$CF$_3$ |
| 208 | Me | Me | 1 | OH | H | H | H | H | CH$_2$CF$_3$ |
| 209 | Me | Me | 0 | OCH$_3$ | H | H | H | H | CH$_2$CF$_3$ |
| 210 | Me | Me | 1 | OCH$_3$ | H | H | H | H | CH$_2$CF$_3$ |
| 211 | Me | Me | 0 | OCH$_2$CH$_3$ | H | H | H | H | CH$_2$CF$_3$ |
| 212 | Me | Me | 1 | OCH$_2$CH$_3$ | H | H | H | H | CH$_2$CF$_3$ |
| 213 | Me | Me | 0 | OCH$_2$CH$_2$CH$_3$ | H | H | H | H | CH$_2$CF$_3$ |
| 214 | Me | Me | 1 | OCH$_2$CH$_2$CH$_3$ | H | H | H | H | CH$_2$CF$_3$ |
| 215 | Me | Me | 0 | OCH$_2$CH$_2$CH$_2$CH$_3$ | H | H | H | H | CH$_2$CF$_3$ |
| 216 | Me | Me | 1 | OCH$_2$CH$_2$CH$_2$CH$_3$ | H | H | H | H | CH$_2$CF$_3$ |
| 217 | Me | Me | 0 | OCH$_2$CH$_2$CH$_2$CH$_2$CH$_3$ | H | H | H | H | CH$_2$CF$_3$ |
| 218 | Me | Me | 1 | SH | H | H | H | H | CH$_2$CF$_3$ |
| 219 | Me | Me | 0 | SH | H | H | H | H | CH$_2$CF$_3$ |
| 220 | Me | Me | 1 | SCH$_3$ | H | H | H | H | CH$_2$CF$_3$ |
| 221 | Me | Me | 0 | SCH$_3$ | H | H | H | H | CH$_2$CF$_3$ |
| 222 | Me | Me | 1 | SCH$_2$CH$_3$ | H | H | H | H | CH$_2$CF$_3$ |
| 223 | Me | Me | 0 | SCH$_2$CH$_3$ | H | H | H | H | CH$_2$CF$_3$ |
| 224 | Me | Me | 1 | SCH$_2$CH$_2$CH$_3$ | H | H | H | H | CH$_2$CF$_3$ |
| 225 | Me | Me | 0 | SCH$_2$CH$_2$CH$_3$ | H | H | H | H | CH$_2$CF$_3$ |
| 226 | Me | Me | 1 | SCH$_2$CH$_2$CH$_2$CH$_3$ | H | H | H | H | CH$_2$CF$_3$ |
| 227 | Me | Me | 0 | SCH$_2$CH$_2$CH$_2$CH$_3$ | H | H | H | H | CH$_2$CF$_3$ |
| 228 | Me | Me | 1 | SCH$_2$CH$_2$CH$_2$CH$_3$ | H | H | H | H | CH$_2$CF$_3$ |
| 229 | F | Me | 0 | H | F | H | H | H | CH$_2$CF$_3$ |
| 230 | F | Me | 1 | H | F | H | H | H | CH$_2$CF$_3$ |
| 231 | F | Me | 0 | H | Cl | H | H | H | CH$_2$CF$_3$ |
| 232 | F | Me | 1 | H | Cl | H | H | H | CH$_2$CF$_3$ |
| 233 | F | Me | 0 | H | Br | H | H | H | CH$_2$CF$_3$ |
| 234 | F | Me | 1 | H | Br | H | H | H | CH$_2$CF$_3$ |
| 235 | F | Me | 0 | H | I | H | H | H | CH$_2$CF$_3$ |
| 236 | F | Me | 1 | H | I | H | H | H | CH$_2$CF$_3$ |
| 237 | F | Me | 0 | H | Me | H | H | H | CH$_2$CF$_3$ |
| 238 | F | Me | 1 | H | Me | H | H | H | CH$_2$CF$_3$ |
| 239 | F | Me | 0 | H | OCH$_3$ | H | H | H | CH$_2$CF$_3$ |
| 240 | F | Me | 1 | H | OCH$_3$ | H | H | H | CH$_2$CF$_3$ |
| 241 | F | Me | 0 | H | NO$_2$ | H | H | H | CH$_2$CF$_3$ |
| 242 | F | Me | 1 | H | NO$_2$ | H | H | H | CH$_2$CF$_3$ |
| 243 | F | Me | 0 | H | CN | H | H | H | CH$_2$CF$_3$ |
| 244 | F | Me | 1 | H | CN | H | H | H | CH$_2$CF$_3$ |
| 245 | F | Me | 0 | H | CO$_2$CH$_3$ | H | H | H | CH$_2$CF$_3$ |
| 246 | F | Me | 1 | H | CO$_2$CH$_3$ | H | H | H | CH$_2$CF$_3$ |
| 247 | F | Me | 0 | H | Cl | Cl | H | H | CH$_2$CF$_3$ |
| 248 | F | Me | 1 | H | Cl | Cl | H | H | CH$_2$CF$_3$ |

TABLE 1-continued

List of compounds

I

| No. | X | Y | n | R₁ | R₂ | R₃ | R₄ | R₅ | R₆ |
|---|---|---|---|---|---|---|---|---|---|
| 249 | F | Me | 0 | H | F | CL | H | H | $CH_2CF_3$ |
| 250 | F | Me | 1 | H | F | Cl | H | H | $CH_2CF_3$ |
| 251 | F | Me | 0 | H | Br | H | F | H | $CH_2CF_3$ |
| 252 | F | Me | 1 | H | Br | H | F | H | $CH_2CF_3$ |
| 253 | F | Me | 0 | Me | H | F | H | H | $CH_2CF_3$ |
| 254 | F | Me | 1 | Me | H | F | H | H | $CH_2CF_3$ |
| 255 | F | Me | 0 | Et | H | F | H | H | $CH_2CF_3$ |
| 256 | F | Me | 1 | Et | H | F | H | H | $CH_2CF_3$ |
| 257 | F | Me | 0 | nPropyl | H | F | H | H | $CH_2CF_3$ |
| 258 | F | Me | 1 | nPropyl | H | F | H | H | $CH_2CF_3$ |
| 259 | F | Me | 0 | isopropyl | H | F | H | H | $CH_2CF_3$ |
| 260 | F | Me | 1 | isopropyl | H | F | H | H | $CH_2CF_3$ |
| 261 | F | Me | 0 | nButyl | H | F | H | H | $CH_2CF_3$ |
| 262 | F | Me | 1 | nButyl | H | F | H | H | $CH_2CF_3$ |
| 263 | F | Me | 0 | nPentyl | H | F | H | H | $CH_2CF_3$ |
| 264 | F | Me | 1 | nPentyl | H | F | H | H | $CH_2CF_3$ |
| 265 | F | Me | 0 | nHexyl | H | F | H | H | $CH_2CF_3$ |
| 266 | F | Me | 1 | nHexyl | H | F | H | H | $CH_2CF_3$ |
| 267 | F | Me | 0 | nHeptyl | H | F | H | H | $CH_2CF_3$ |
| 268 | F | Me | 1 | nHeptyl | H | F | H | H | $CH_2CF_3$ |
| 269 | F | Me | 0 | nOctyl | H | F | H | H | $CH_2CF_3$ |
| 270 | F | Me | 1 | nOctyl | H | F | H | H | $CH_2CF_3$ |
| 271 | F | Me | 0 | nNonyl | H | F | H | H | $CH_2CF_3$ |
| 272 | F | Me | 1 | nNonyl | H | F | H | H | $CH_2CF_3$ |
| 273 | F | Me | 0 | nDecyl | H | F | H | H | $CH_2CF_3$ |
| 274 | F | Me | 1 | nDecyl | H | F | H | H | $CH_2CF_3$ |
| 275 | F | Me | 0 | F | H | F | H | H | $CH_2CF_3$ |
| 276 | F | Me | 1 | F | H | F | H | H | $CH_2CF_3$ |
| 277 | F | Me | 0 | Cl | H | F | H | H | $CH_2CF_3$ |
| 278 | F | Me | 1 | Cl | H | F | H | H | $CH_2CF_3$ |
| 279 | F | Me | 0 | Br | H | F | H | H | $CH_2CF_3$ |
| 280 | F | Me | 1 | Br | H | F | H | H | $CH_2CF_3$ |
| 281 | F | Me | 0 | I | H | F | H | H | $CH_2CF_3$ |
| 282 | F | Me | 1 | I | H | F | H | H | $CH_2CF_3$ |
| 283 | F | Me | 0 | CN | H | F | H | H | $CH_2CF_3$ |
| 284 | F | Me | 1 | CN | H | F | H | H | $CH_2CF_3$ |
| 285 | F | Me | 0 | $NO_2$ | H | F | H | H | $CH_2CF_3$ |
| 286 | F | Me | 1 | $NO_2$ | H | F | H | H | $CH_2CF_3$ |
| 287 | F | Me | 0 | $NH_2$ | H | F | H | H | $CH_2CF_3$ |
| 288 | F | Me | 1 | $NH_2$ | H | F | H | H | $CH_2CF_3$ |
| 289 | F | Me | 0 | $CH_2OH$ | H | F | H | H | $CH_2CF_3$ |
| 290 | F | Me | 1 | $CH_2OH$ | H | F | H | H | $CH_2CF_3$ |
| 291 | F | Me | 0 | $COCH_3$ | H | F | H | H | $CH_2CF_3$ |
| 292 | F | Me | 1 | $COCH_3$ | H | F | H | H | $CH_2CF_3$ |
| 293 | F | Me | 0 | $COCH_2CH_3$ | H | F | H | H | $CH_2CF_3$ |
| 294 | F | Me | 1 | $COCH_2CH_3$ | H | F | H | H | $CH_2CF_3$ |
| 295 | F | Me | 0 | $COCH_2CH_2CH_3$ | H | F | H | H | $CH_2CF_3$ |
| 296 | F | Me | 1 | $COCH_2CH_2CH_3$ | H | F | H | H | $CH_2CF_3$ |
| 297 | F | Me | 0 | $COCH_2CH_2CH_2CH_3$ | H | F | H | H | $CH_2CF_3$ |
| 298 | F | Me | 1 | $COCH_2CH_2CH_2CH_3$ | H | F | H | H | $CH_2CF_3$ |
| 299 | F | Me | 0 | $COCH_2CH_2CH_2CH_2CH_3$ | H | F | H | H | $CH_2CF_3$ |
| 300 | F | Me | 1 | $COCH_2CH_2CH_2CH_2CH_3$ | H | F | H | H | $CH_2CF_3$ |
| 301 | F | Me | 0 | COOH | H | F | H | H | $CH_2CF_3$ |
| 302 | F | Me | 1 | COOH | H | F | H | H | $CH_2CF_3$ |
| 303 | F | Me | 0 | $CO_2CH_3$ | H | F | H | H | $CH_2CF_3$ |
| 304 | F | Me | 1 | $CO_2CH_3$ | H | F | H | H | $CH_2CF_3$ |
| 305 | F | Me | 0 | $CO_2CH_2CH_3$ | H | F | H | H | $CH_2CF_3$ |
| 306 | F | Me | 1 | $CO_2CH_2CH_3$ | H | F | H | H | $CH_2CF_3$ |
| 307 | F | Me | 0 | $CO_2CH_2CH_2CH_3$ | H | F | H | H | $CH_2CF_3$ |
| 308 | F | Me | 1 | $CO_2CH_2CH_2CH_3$ | H | F | H | H | $CH_2CF_3$ |
| 309 | F | Me | 0 | $CO_2CH_2CH_2CH_2CH_3$ | H | F | H | H | $CH_2CF_3$ |

TABLE 1-continued

List of compounds

I

| No. | X | Y | n | R$_1$ | R$_2$ | R$_3$ | R$_4$ | R$_5$ | R$_6$ |
|---|---|---|---|---|---|---|---|---|---|
| 310 | F | Me | 1 | CO$_2$CH$_2$CH$_2$CH$_3$ | H | F | H | H | CH$_2$CF$_3$ |
| 311 | F | Me | 0 | CO$_2$CH$_2$CH$_2$CH$_2$CH$_3$ | H | F | H | H | CH$_2$CF$_3$ |
| 312 | F | Me | 1 | CO$_2$CH$_2$CH$_2$CH$_2$CH$_3$ | H | F | H | H | CH$_2$CF$_3$ |
| 313 | F | Me | 0 | CO$_2$CH(CH$_3$)$_2$ | H | F | H | H | CH$_2$CF$_3$ |
| 314 | F | Me | 1 | CO$_2$CH(CH$_3$)$_2$ | H | F | H | H | CH$_2$CF$_3$ |
| 315 | F | Me | 0 | CO$_2$CH$_2$CH(CH$_3$)$_2$ | H | F | H | H | CH$_2$CF$_3$ |
| 316 | F | Me | 1 | CO$_2$CH$_2$CH(CH$_3$)$_2$ | H | F | H | H | CH$_2$CF$_3$ |
| 317 | F | Me | 0 | CO$_2$CH=CH$_2$ | H | F | H | H | CH$_2$CF$_3$ |
| 318 | F | Me | 1 | CO$_2$CH=CH$_2$ | H | F | H | H | CH$_2$CF$_3$ |
| 319 | F | Me | 0 | CO$_2$CH$_2$CH=CH$_2$ | H | F | H | H | CH$_2$CF$_3$ |
| 320 | F | Me | 1 | CO$_2$CH$_2$CH=CH$_2$ | H | F | H | H | CH$_2$CF$_3$ |
| 321 | F | Me | 0 | CO$_2$CH$_2$CF$_3$ | H | F | H | H | CH$_2$CF$_3$ |
| 322 | F | Me | 1 | CO$_2$CH$_2$CF$_3$ | H | F | H | H | CH$_2$CF$_3$ |
| 323 | F | Me | 0 | CO$_2$CH$_2$CH$_2$Cl | H | F | H | H | CH$_2$CF$_3$ |
| 324 | F | Me | 1 | CO$_2$CH$_2$CH$_2$Cl | H | F | H | H | CH$_2$CF$_3$ |
| 325 | F | Me | 0 | CO$_2$CH$_2$CH$_2$Br | H | F | H | H | CH$_2$CF$_3$ |
| 326 | F | Me | 1 | CO$_2$CH$_2$CH$_2$Br | H | F | H | H | CH$_2$CF$_3$ |
| 327 | F | Me | 0 | CO$_2$CH$_2$OCH$_3$ | H | F | H | H | CH$_2$CF$_3$ |
| 328 | F | Me | 1 | CO$_2$CH$_2$COCH$_3$ | H | F | H | H | CH$_2$CF$_3$ |
| 329 | F | Me | 0 | CONH$_2$ | H | F | H | H | CH$_2$CF$_3$ |
| 330 | F | Me | 1 | CONH$_2$ | H | F | H | H | CH$_2$CF$_3$ |
| 331 | F | Me | 0 | CONHCH$_3$ | H | F | H | H | CH$_2$CF$_3$ |
| 332 | F | Me | 1 | CONHCH$_3$ | H | F | H | H | CH$_2$CF$_3$ |
| 333 | F | Me | 0 | CON(CH$_3$)$_2$ | H | F | H | H | CH$_2$CF$_3$ |
| 334 | F | Me | 1 | CON(CH$_3$)$_2$ | H | F | H | H | CH$_2$CF$_3$ |
| 335 | F | Me | 0 | CONHCH$_2$CH$_3$ | H | F | H | H | CH$_2$CF$_3$ |
| 336 | F | Me | 1 | CONHCH$_2$CH$_3$ | H | F | H | H | CH$_2$CF$_3$ |
| 337 | F | Me | 0 | CONHCH$_2$CH$_2$CH$_3$ | H | F | H | H | CH$_2$CF$_3$ |
| 338 | F | Me | 1 | CONHCH$_2$CH$_2$CH$_3$ | H | F | H | H | CH$_2$CF$_3$ |
| 339 | F | Me | 0 | CONHCH$_2$CH$_2$CH$_2$CH$_3$ | H | F | H | H | CH$_2$CF$_3$ |
| 340 | F | Me | 1 | CONHCH$_2$CH$_2$CH$_2$CH$_3$ | H | F | H | H | CH$_2$CF$_3$ |
| 341 | F | Me | 0 | CONHCH$_2$CH$_2$CH$_2$CH$_2$CH$_3$ | H | F | H | H | CH$_2$CF$_3$ |
| 342 | F | Me | 1 | CONHCH$_2$CH$_2$CH$_2$CH$_2$CH$_3$ | H | F | H | H | CH2CF3 |
| 343 | F | Me | 0 | CSNHCH$_3$ | H | F | H | H | CH2CF3 |
| 344 | F | Me | 1 | CSNHCH$_3$ | H | F | H | H | CH2CF3 |
| 345 | F | Me | 0 | CSN(CH$_3$)$_2$ | H | F | H | H | CH2CF3 |
| 346 | F | Me | 1 | CSN(CH$_3$)$_2$ | H | F | H | H | CH2CF3 |
| 347 | F | Me | 0 | CSNHCH$_2$CH$_3$ | H | F | H | H | CH2CF3 |
| 348 | F | Me | 1 | CSNHCH$_2$CH$_3$ | H | F | H | H | CH2CF3 |
| 349 | F | Me | 0 | CONHCH$_2$CH$_3$ | H | F | H | H | CH2CF3 |
| 350 | F | Me | 1 | CONHCH$_2$CH$_3$ | H | F | H | H | CH2CF3 |
| 351 | F | Me | 0 | OH | H | F | H | H | CH$_2$CF$_3$ |
| 352 | F | Me | 1 | OH | H | F | H | H | CH$_2$CF$_3$ |
| 353 | F | Me | 0 | OCH$_3$ | H | F | H | H | CH$_2$CF$_3$ |
| 354 | F | Me | 1 | OCH$_3$ | H | F | H | H | CH$_2$CF$_3$ |
| 355 | F | Me | 0 | OCH$_2$CH$_3$ | H | F | H | H | CH$_2$CF$_3$ |
| 356 | F | Me | 1 | OCH$_2$CH$_3$ | H | F | H | H | CH$_2$CF$_3$ |
| 357 | F | Me | 0 | OCH$_2$CH$_2$CH$_3$ | H | F | H | H | CH$_2$CF$_3$ |
| 358 | F | Me | 1 | OCH$_2$CH$_2$CH$_3$ | H | F | H | H | CH$_2$CF$_3$ |
| 359 | F | Me | 0 | OCH$_2$CH$_2$CH$_2$CH$_3$ | H | F | H | H | CH$_2$CF$_3$ |
| 360 | F | Me | 1 | OCH$_2$CH$_2$CH$_2$CH$_3$ | H | F | H | H | CH$_2$CF$_3$ |
| 361 | F | Me | 0 | OCH$_2$CH$_2$CH$_2$CH$_2$CH$_3$ | H | F | H | H | CH$_2$CF$_3$ |
| 362 | F | Me | 1 | SH | H | F | H | H | CH$_2$CF$_3$ |
| 363 | F | Me | 0 | SH | H | F | H | H | CH$_2$CF$_3$ |
| 364 | F | Me | 1 | SCH$_3$ | H | F | H | H | CH$_2$CF$_3$ |
| 365 | F | Me | 0 | SCH$_3$ | H | F | H | H | CH$_2$CF$_3$ |
| 366 | F | Me | 1 | SCH$_2$CH$_3$ | H | F | H | H | CH$_2$CF$_3$ |
| 367 | F | Me | 0 | SCH$_2$CH$_3$ | H | F | H | H | CH$_2$CF$_3$ |
| 368 | F | Me | 1 | SCH$_2$CH$_2$CH$_3$ | H | F | H | H | CH$_2$CF$_3$ |
| 369 | F | Me | 0 | SCH$_2$CH$_2$CH$_3$ | H | F | H | H | CH$_2$CF$_3$ |
| 370 | F | Me | 1 | SCH$_2$CH$_2$CH$_2$CH$_3$ | H | F | H | H | CH$_2$CF$_3$ |

TABLE 1-continued

List of compounds

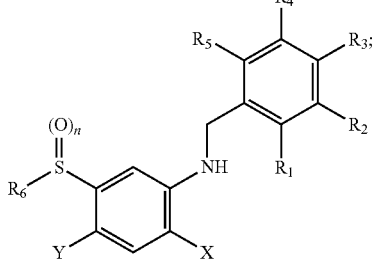

I

| No. | X | Y | n | R₁ | R₂ | R₃ | R₄ | R₅ | R₆ |
|---|---|---|---|---|---|---|---|---|---|
| 371 | F | Me | 0 | SCH$_2$CH$_2$CH$_2$CH$_3$ | H | F | H | H | CH$_2$CF$_3$ |
| 372 | F | Me | 1 | SCH$_2$CH$_2$CH$_2$CH$_2$CH$_3$ | H | F | H | H | CH$_2$CF$_3$ |
| 373 | Me | Me | 0 | Me | H | F | H | H | CH$_2$CF$_3$ |
| 374 | Me | Me | 1 | Me | H | F | H | H | CH$_2$CF$_3$ |
| 375 | Me | Me | 0 | Et | H | F | H | H | CH$_2$CF$_3$ |
| 376 | Me | Me | 1 | Et | H | F | H | H | CH$_2$CF$_3$ |
| 377 | Me | Me | 0 | nPropyl | H | F | H | H | CH$_2$CF$_3$ |
| 378 | Me | Me | 1 | nPropyl | H | F | H | H | CH$_2$CF$_3$ |
| 379 | Me | Me | 0 | isopropyl | H | F | H | H | CH$_2$CF$_3$ |
| 380 | Me | Me | 1 | isopropyl | H | F | H | H | CH$_2$CF$_3$ |
| 381 | Me | Me | 0 | nButyl | H | F | H | H | CH$_2$CF$_3$ |
| 382 | Me | Me | 1 | nButyl | H | F | H | H | CH$_2$CF$_3$ |
| 383 | Me | Me | 0 | nPentyl | H | F | H | H | CH$_2$CF$_3$ |
| 384 | Me | Me | 1 | nPentyl | H | F | H | H | CH$_2$CF$_3$ |
| 385 | Me | Me | 0 | nHexyl | H | F | H | H | CH$_2$CF$_3$ |
| 386 | Me | Me | 1 | nHexyl | H | F | H | H | CH$_2$CF$_3$ |
| 387 | Me | Me | 0 | nHeptyl | H | F | H | H | CH$_2$CF$_3$ |
| 388 | Me | Me | 1 | nHeptyl | H | F | H | H | CH$_2$CF$_3$ |
| 389 | Me | Me | 0 | nOctyl | H | F | H | H | CH$_2$CF$_3$ |
| 390 | Me | Me | 1 | nOctyl | H | F | H | H | CH$_2$CF$_3$ |
| 391 | Me | Me | 0 | nNonyl | H | F | H | H | CH$_2$CF$_3$ |
| 392 | Me | Me | 1 | nNonyl | H | F | H | H | CH$_2$CF$_3$ |
| 393 | Me | Me | 0 | nDecyl | H | F | H | H | CH$_2$CF$_3$ |
| 394 | Me | Me | 1 | nDecyl | H | F | H | H | CH$_2$CF$_3$ |
| 395 | Me | Me | 0 | F | H | F | H | H | CH$_2$CF$_3$ |
| 396 | Me | Me | 1 | F | H | F | H | H | CH$_2$CF$_3$ |
| 397 | Me | Me | 0 | Cl | H | F | H | H | CH$_2$CF$_3$ |
| 398 | Me | Me | 1 | Cl | H | F | H | H | CH$_2$CF$_3$ |
| 399 | Me | Me | 0 | Br | H | F | H | H | CH$_2$CF$_3$ |
| 400 | Me | Me | 1 | Br | H | F | H | H | CH$_2$CF$_3$ |
| 401 | Me | Me | 0 | I | H | F | H | H | CH$_2$CF$_3$ |
| 402 | Me | Me | 1 | I | H | F | H | H | CH$_2$CF$_3$ |
| 403 | Me | Me | 0 | CN | H | F | H | H | CH$_2$CF$_3$ |
| 404 | Me | Me | 1 | CN | H | F | H | H | CH$_2$CF$_3$ |
| 405 | Me | Me | 0 | NO$_2$ | H | F | H | H | CH$_2$CF$_3$ |
| 406 | Me | Me | 1 | NO$_2$ | H | F | H | H | CH$_2$CF$_3$ |
| 407 | Me | Me | 0 | NH$_2$ | H | F | H | H | CH$_2$CF$_3$ |
| 408 | Me | Me | 1 | NH$_2$ | H | F | H | H | CH$_2$CF$_3$ |
| 409 | Me | Me | 0 | CH$_2$OH | H | F | H | H | CH$_2$CF$_3$ |
| 410 | Me | Me | 1 | CH$_2$OH | H | F | H | H | CH$_2$CF$_3$ |
| 411 | Me | Me | 0 | COCH$_3$ | H | F | H | H | CH$_2$CF$_3$ |
| 412 | Me | Me | 1 | COCH$_3$ | H | F | H | H | CH$_2$CF$_3$ |
| 413 | Me | Me | 0 | COCH$_2$CH$_3$ | H | F | H | H | CH$_2$CF$_3$ |
| 414 | Me | Me | 1 | COCH$_2$CH$_3$ | H | F | H | H | CH$_2$CF$_3$ |
| 415 | Me | Me | 0 | COCH$_2$CH$_2$CH$_3$ | H | F | H | H | CH$_2$CF$_3$ |
| 416 | Me | Me | 1 | COCH$_2$CH$_2$CH$_3$ | H | F | H | H | CH$_2$CF$_3$ |
| 417 | Me | Me | 0 | COCH$_2$CH$_2$CH$_2$CH$_3$ | H | F | H | H | CH$_2$CF$_3$ |
| 418 | Me | Me | 1 | COCH$_2$CH$_2$CH$_2$CH$_3$ | H | F | H | H | CH$_2$CF$_3$ |
| 419 | Me | Me | 0 | COCH$_2$CH$_2$CH$_2$CH$_2$CH$_3$ | H | F | H | H | CH$_2$CF$_3$ |
| 420 | Me | Me | 1 | COCH$_2$CH$_2$CH$_2$CH$_2$CH$_3$ | H | F | H | H | CH$_2$CF$_3$ |
| 421 | Me | Me | 0 | COOH | H | F | H | H | CH$_2$CF$_3$ |
| 422 | Me | Me | 1 | COOH | H | F | H | H | CH$_2$CF$_3$ |
| 423 | Me | Me | 0 | CO$_2$CH$_3$ | H | F | H | H | CH$_2$CF$_3$ |
| 424 | Me | Me | 1 | CO$_2$CH$_3$ | H | F | H | H | CH$_2$CF$_3$ |
| 425 | Me | Me | 0 | CO$_2$CH$_2$CH$_3$ | H | F | H | H | CH$_2$CF$_3$ |
| 426 | Me | Me | 1 | CO$_2$CH$_2$CH$_3$ | H | F | H | H | CH$_2$CF$_3$ |
| 427 | Me | Me | 0 | CO$_2$CH$_2$CH$_2$CH$_3$ | H | F | H | H | CH$_2$CF$_3$ |
| 428 | Me | Me | 1 | CO$_2$CH$_2$CH$_2$CH$_3$ | H | F | H | H | CH$_2$CF$_3$ |
| 429 | Me | Me | 0 | CO$_2$CH$_2$CH$_2$CH$_2$CH$_3$ | H | F | H | H | CH$_2$CF$_3$ |
| 430 | Me | Me | 1 | CO$_2$CH$_2$CH$_2$CH$_2$CH$_3$ | H | F | H | H | CH$_2$CF$_3$ |
| 431 | Me | Me | 0 | CO$_2$CH$_2$CH$_2$CH$_2$CH$_2$CH$_3$ | H | F | H | H | CH$_2$CF$_3$ |

TABLE 1-continued

List of compounds

I

| No. | X | Y | n | $R_1$ | $R_2$ | $R_3$ | $R_4$ | $R_5$ | $R_6$ |
|---|---|---|---|---|---|---|---|---|---|
| 432 | Me | Me | 1 | $CO_2CH_2CH_2CH_2CH_2CH_3$ | H | F | H | H | $CH_2CF_3$ |
| 433 | Me | Me | 0 | $CO_2CH(CH_3)_2$ | H | F | H | H | $CH_2CF_3$ |
| 434 | Me | Me | 1 | $CO_2CH(CH_3)_2$ | H | F | H | H | $CH_2CF_3$ |
| 435 | Me | Me | 0 | $CO_2CH_2CH(CH_3)_2$ | H | F | H | H | $CH_2CF_3$ |
| 436 | Me | Me | 1 | $CO_2CH_2CH(CH_3)_2$ | H | F | H | H | $CH_2CF_3$ |
| 437 | Me | Me | 0 | $CO_2CH=CH_2$ | H | F | H | H | $CH_2CF_3$ |
| 438 | Me | Me | 1 | $CO_2CH=CH_2$ | H | F | H | H | $CH_2CF_3$ |
| 439 | Me | Me | 0 | $CO_2CH_2CH=CH_2$ | H | F | H | H | $CH_2CF_3$ |
| 440 | Me | Me | 1 | $CO_2CH_2CH=CH_2$ | H | F | H | H | $CH_2CF_3$ |
| 441 | Me | Me | 0 | $CO_2CH_2CF_3$ | H | F | H | H | $CH_2CF_3$ |
| 442 | Me | Me | 1 | $CO_2CH_2CF_3$ | H | F | H | H | $CH_2CF_3$ |
| 443 | Me | Me | 0 | $CO_2CH_2CH_2Cl$ | H | F | H | H | $CH_2CF_3$ |
| 444 | Me | Me | 1 | $CO_2CH_2CH_2Cl$ | H | F | H | H | $CH_2CF_3$ |
| 445 | Me | Me | 0 | $CO_2CH_2CH_2Br$ | H | F | H | H | $CH_2CF_3$ |
| 446 | Me | Me | 1 | $CO_2CH_2CH_2Br$ | H | F | H | H | $CH_2CF_3$ |
| 447 | Me | Me | 0 | $CO_2CH_2OCH_3$ | H | F | H | H | $CH_2CF_3$ |
| 448 | Me | Me | 1 | $CO_2CH_2COCH_3$ | H | F | H | H | $CH_2CF_3$ |
| 449 | Me | Me | 0 | $CONH_2$ | H | F | H | H | $CH_2CF_3$ |
| 450 | Me | Me | 1 | $CONH_2$ | H | F | H | H | $CH_2CF_3$ |
| 451 | Me | Me | 0 | $CONHCH_3$ | H | F | H | H | $CH_2CF_3$ |
| 452 | Me | Me | 1 | $CONHCH_3$ | H | F | H | H | $CH_2CF_3$ |
| 453 | Me | Me | 0 | $CON(CH_3)_2$ | H | F | H | H | $CH_2CF_3$ |
| 454 | Me | Me | 1 | $CON(CH_3)_2$ | H | F | H | H | $CH_2CF_3$ |
| 455 | Me | Me | 0 | $CONHCH_2CH_3$ | H | F | H | H | $CH_2CF_3$ |
| 456 | Me | Me | 1 | $CONHCH_2CH_3$ | H | F | H | H | $CH_2CF_3$ |
| 457 | Me | Me | 0 | $CONHCH_2CH_2CH_3$ | H | F | H | H | $CH_2CF_3$ |
| 458 | Me | Me | 1 | $CONHCH_2CH_2CH_3$ | H | F | H | H | $CH_2CF_3$ |
| 459 | Me | Me | 0 | $CONHCH_2CH_2CH_2CH_3$ | H | F | H | H | $CH_2CF_3$ |
| 460 | Me | Me | 1 | $CONHCH_2CH_2CH_2CH_3$ | H | F | H | H | $CH_2CF_3$ |
| 461 | Me | Me | 0 | $CONHCH_2CH_2CH_2CH_2CH_3$ | H | F | H | H | $CH_2CF_3$ |
| 462 | Me | Me | 1 | $CONHCH_2CH_2CH_2CH_2CH_3$ | H | F | H | H | $CH_2CF_3$ |
| 463 | Me | Me | 0 | OH | H | F | H | H | $CH_2CF_3$ |
| 464 | Me | Me | 1 | OH | H | F | H | H | $CH_2CF_3$ |
| 465 | Me | Me | 0 | $OCH_3$ | H | F | H | H | $CH_2CF_3$ |
| 466 | Me | Me | 1 | $OCH_3$ | H | F | H | H | $CH_2CF_3$ |
| 467 | Me | Me | 0 | $OCH_2CH_3$ | H | F | H | H | $CH_2CF_3$ |
| 468 | Me | Me | 1 | $OCH_2CH_3$ | H | F | H | H | $CH_2CF_3$ |
| 469 | Me | Me | 0 | $OCH_2CH_2CH_3$ | H | F | H | H | $CH_2CF_3$ |
| 470 | Me | Me | 1 | $OCH_2CH_2CH_3$ | H | F | H | H | $CH_2CF_3$ |
| 471 | Me | Me | 0 | $OCH_2CH_2CH_2CH_3$ | H | F | H | H | $CH_2CF_3$ |
| 472 | Me | Me | 1 | $OCH_2CH_2CH_2CH_3$ | H | F | H | H | $CH_2CF_3$ |
| 473 | Me | Me | 0 | $OCH_2CH_2CH_2CH_2CH_3$ | H | F | H | H | $CH_2CF_3$ |
| 474 | Me | Me | 1 | SH | H | F | H | H | $CH_2CF_3$ |
| 475 | Me | Me | 0 | SH | H | F | H | H | $CH_2CF_3$ |
| 476 | Me | Me | 1 | $SCH_3$ | H | F | H | H | $CH_2CF_3$ |
| 477 | Me | Me | 0 | $SCH_3$ | H | F | H | H | $CH_2CF_3$ |
| 478 | Me | Me | 1 | $SCH_2CH_3$ | H | F | H | H | $CH_2CF_3$ |
| 479 | Me | Me | 0 | $SCH_2CH_3$ | H | F | H | H | $CH_2CF_3$ |
| 480 | Me | Me | 1 | $SCH_2CH_2CH_3$ | H | F | H | H | $CH_2CF_3$ |
| 481 | Me | Me | 0 | $SCH_2CH_2CH_3$ | H | F | H | H | $CH_2CF_3$ |
| 482 | Me | Me | 1 | $SCH_2CH_2CH_2CH_3$ | H | F | H | H | $CH_2CF_3$ |
| 483 | Me | Me | 0 | $SCH_2CH_2CH_2CH_3$ | H | F | H | H | $CH_2CF_3$ |
| 484 | Me | Me | 1 | $SCH_2CH_2CH_2CH_2CH_3$ | H | F | H | H | $CH_2CF_3$ |
| 485 | F | Me | 0 | Me | H | Cl | H | H | $CH_2CF_3$ |
| 486 | F | Me | 1 | Me | H | Cl | H | H | $CH_2CF_3$ |
| 487 | F | Me | 0 | Et | H | Cl | H | H | $CH_2CF_3$ |
| 488 | F | Me | 1 | Et | H | Cl | H | H | $CH_2CF_3$ |
| 489 | F | Me | 0 | nPropyl | H | Cl | H | H | $CH_2CF_3$ |
| 490 | F | Me | 1 | nPropyl | H | Cl | H | H | $CH_2CF_3$ |
| 491 | F | Me | 0 | isopropyl | H | Cl | H | H | $CH_2CF_3$ |
| 492 | F | Me | 1 | isopropyl | H | Cl | H | H | $CH_2CF_3$ |

TABLE 1-continued

List of compounds

I

| No. | X | Y | n | $R_1$ | $R_2$ | $R_3$ | $R_4$ | $R_5$ | $R_6$ |
|---|---|---|---|---|---|---|---|---|---|
| 493 | F | Me | 0 | nButyl | H | Cl | H | H | $CH_2CF_3$ |
| 494 | F | Me | 1 | nButyl | H | Cl | H | H | $CH_2CF_3$ |
| 495 | F | Me | 0 | nPentyl | H | Cl | H | H | $CH_2CF_3$ |
| 496 | F | Me | 1 | nPentyl | H | Cl | H | H | $CH_2CF_3$ |
| 497 | F | Me | 0 | nHexyl | H | Cl | H | H | $CH_2CF_3$ |
| 498 | F | Me | 1 | nHexyl | H | Cl | H | H | $CH_2CF_3$ |
| 499 | F | Me | 0 | nHeptyl | H | Cl | H | H | $CH_2CF_3$ |
| 500 | F | Me | 1 | nHeptyl | H | Cl | H | H | $CH_2CF_3$ |
| 501 | F | Me | 0 | nOctyl | H | Cl | H | H | $CH_2CF_3$ |
| 502 | F | Me | 1 | nOctyl | H | Cl | H | H | $CH_2CF_3$ |
| 503 | F | Me | 0 | nNonyl | H | Cl | H | H | $CH_2CF_3$ |
| 504 | F | Me | 1 | nNonyl | H | Cl | H | H | $CH_2CF_3$ |
| 505 | F | Me | 0 | nDecyl | H | Cl | H | H | $CH_2CF_3$ |
| 506 | F | Me | 1 | nDecyl | H | Cl | H | H | $CH_2CF_3$ |
| 507 | F | Me | 0 | F | H | Cl | H | H | $CH_2CF_3$ |
| 508 | F | Me | 1 | F | H | Cl | H | H | $CH_2CF_3$ |
| 509 | F | Me | 0 | Cl | H | Cl | H | H | $CH_2CF_3$ |
| 510 | F | Me | 1 | Cl | H | Cl | H | H | $CH_2CF_3$ |
| 511 | F | Me | 0 | Br | H | Cl | H | H | $CH_2CF_3$ |
| 512 | F | Me | 1 | Br | H | Cl | H | H | $CH_2CF_3$ |
| 513 | F | Me | 0 | I | H | Cl | H | H | $CH_2CF_3$ |
| 514 | F | Me | 1 | I | H | Cl | H | H | $CH_2CF_3$ |
| 515 | F | Me | 0 | CN | H | Cl | H | H | $CH_2CF_3$ |
| 516 | F | Me | 1 | CN | H | Cl | H | H | $CH_2CF_3$ |
| 517 | F | Me | 0 | $NO_2$ | H | Cl | H | H | $CH_2CF_3$ |
| 518 | F | Me | 1 | $NO_2$ | H | Cl | H | H | $CH_2CF_3$ |
| 519 | F | Me | 0 | $NH_2$ | H | Cl | H | H | $CH_2CF_3$ |
| 520 | F | Me | 1 | $NH_2$ | H | Cl | H | H | $CH_2CF_3$ |
| 521 | F | Me | 0 | $CH_2OH$ | H | Cl | H | H | $CH_2CF_3$ |
| 522 | F | Me | 1 | $CH_2OH$ | H | Cl | H | H | $CH_2CF_3$ |
| 523 | F | Me | 0 | $COCH_3$ | H | Cl | H | H | $CH_2CF_3$ |
| 524 | F | Me | 1 | $COCH_3$ | H | Cl | H | H | $CH_2CF_3$ |
| 525 | F | Me | 0 | $COCH_2CH_3$ | H | Cl | H | H | $CH_2CF_3$ |
| 526 | F | Me | 1 | $COCH_2CH_3$ | H | Cl | H | H | $CH_2CF_3$ |
| 527 | F | Me | 0 | $COCH_2CH_2CH_3$ | H | Cl | H | H | $CH_2CF_3$ |
| 528 | F | Me | 1 | $COCH_2CH_2CH_3$ | H | Cl | H | H | $CH_2CF_3$ |
| 529 | F | Me | 0 | $COCH_2CH_2CH_2CH_3$ | H | Cl | H | H | $CH_2CF_3$ |
| 530 | F | Me | 1 | $COCH_2CH_2CH_2CH_3$ | H | Cl | H | H | $CH_2CF_3$ |
| 531 | F | Me | 0 | $COCH_2CH_2CH_2CH_2CH_3$ | H | Cl | H | H | $CH_2CF_3$ |
| 532 | F | Me | 1 | $COCH_2CH_2CH_2CH_2CH_3$ | H | Cl | H | H | $CH_2CF_3$ |
| 533 | F | Me | 0 | COOH | H | Cl | H | H | $CH_2CF_3$ |
| 534 | F | Me | 1 | COOH | H | Cl | H | H | $CH_2CF_3$ |
| 535 | F | Me | 0 | $CO_2CH_3$ | H | Cl | H | H | $CH_2CF_3$ |
| 536 | F | Me | 1 | $CO_2CH_3$ | H | Cl | H | H | $CH_2CF_3$ |
| 537 | F | Me | 0 | $CO_2CH_2CH_3$ | H | Cl | H | H | $CH_2CF_3$ |
| 538 | F | Me | 1 | $CO_2CH_2CH_3$ | H | Cl | H | H | $CH_2CF_3$ |
| 539 | F | Me | 0 | $CO_2CH_2CH_2CH_3$ | H | Cl | H | H | $CH_2CF_3$ |
| 540 | F | Me | 1 | $CO_2CH_2CH_2CH_3$ | H | Cl | H | H | $CH_2CF_3$ |
| 541 | F | Me | 0 | $CO_2CH_2CH_2CH_2CH_3$ | H | Cl | H | H | $CH_2CF_3$ |
| 542 | F | Me | 1 | $CO_2CH_2CH_2CH_2CH_3$ | H | Cl | H | H | $CH_2CF_3$ |
| 543 | F | Me | 0 | $CO_2CH_2CH_2CH_2CH_2CH_3$ | H | Cl | H | H | $CH_2CF_3$ |
| 544 | F | Me | 1 | $CO_2CH_2CH_2CH_2CH_2CH_3$ | H | Cl | H | H | $CH_2CF_3$ |
| 545 | F | Me | 0 | $CO_2CH(CH_3)_2$ | H | Cl | H | H | $CH_2CF_3$ |
| 546 | F | Me | 1 | $CO_2CH(CH_3)_2$ | H | Cl | H | H | $CH_2CF_3$ |
| 547 | F | Me | 0 | $CO_2CH_2CH(CH_3)_2$ | H | Cl | H | H | $CH_2CF_3$ |
| 548 | F | Me | 1 | $CO_2CH_2CH(CH_3)_2$ | H | Cl | H | H | $CH_2CF_3$ |
| 549 | F | Me | 0 | $CO_2CH=CH_2$ | H | Cl | H | H | $CH_2CF_3$ |
| 550 | F | Me | 1 | $CO_2CH=CH_2$ | H | Cl | H | H | $CH_2CF_3$ |
| 551 | F | Me | 0 | $CO_2CH_2CH=CH_2$ | H | Cl | H | H | $CH_2CF_3$ |
| 552 | F | Me | 1 | $CO_2CH_2CH=CH_2$ | H | Cl | H | H | $CH_2CF_3$ |
| 553 | F | Me | 0 | $CO_2CH_2CF_3$ | H | Cl | H | H | $CH_2CF_3$ |

TABLE 1-continued

List of compounds

I

| No. | X | Y | n | R₁ | R₂ | R₃ | R₄ | R₅ | R₆ |
|---|---|---|---|---|---|---|---|---|---|
| 554 | F | Me | 1 | CO₂CH₂CF₃ | H | Cl | H | H | CH₂CF₃ |
| 555 | F | Me | 0 | CO₂CH₂CH₂Cl | H | Cl | H | H | CH₂CF₃ |
| 556 | F | Me | 1 | CO₂CH₂CH₂Cl | H | Cl | H | H | CH₂CF₃ |
| 557 | F | Me | 0 | CO₂CH₂CH₂Br | H | Cl | H | H | CH₂CF₃ |
| 558 | F | Me | 1 | CO₂CH₂CH₂Br | H | Cl | H | H | CH₂CF₃ |
| 559 | F | Me | 0 | CO₂CH₂OCH₃ | H | Cl | H | H | CH₂CF₃ |
| 560 | F | Me | 1 | CO₂CH₂COCH₃ | H | Cl | H | H | CH₂CF₃ |
| 561 | F | Me | 0 | CONH₂ | H | Cl | H | H | CH₂CF₃ |
| 562 | F | Me | 1 | CONH₂ | H | Cl | H | H | CH₂CF₃ |
| 563 | F | Me | 0 | CONHCH₃ | H | Cl | H | H | CH₂CF₃ |
| 564 | F | Me | 1 | CONHCH₃ | H | Cl | H | H | CH₂CF₃ |
| 565 | F | Me | 0 | CON(CH₃)₂ | H | Cl | H | H | CH₂CF₃ |
| 566 | F | Me | 1 | CON(CH₃)₂ | H | Cl | H | H | CH₂CF₃ |
| 567 | F | Me | 0 | CONHCH₂CH₃ | H | Cl | H | H | CH₂CF₃ |
| 568 | F | Me | 1 | CONHCH₂CH₃ | H | Cl | H | H | CH₂CF₃ |
| 569 | F | Me | 0 | CONHCH₂CH₂CH₃ | H | Cl | H | H | CH₂CF₃ |
| 570 | F | Me | 1 | CONHCH₂CH₂CH₃ | H | Cl | H | H | CH₂CF₃ |
| 571 | F | Me | 0 | CONHCH₂CH₂CH₂CH₃ | H | Cl | H | H | CH₂CF₃ |
| 572 | F | Me | 1 | CONHCH₂CH₂CH₂CH₃ | H | Cl | H | H | CH₂CF₃ |
| 573 | F | Me | 0 | CONHCH₂CH₂CH₂CH₂CH₃ | H | Cl | H | H | CH₂CF₃ |
| 574 | F | Me | 1 | CONHCH₂CH₂CH₂CH₂CH₃ | H | Cl | H | H | CH₂CF₃ |
| 575 | F | Me | 0 | OH | H | Cl | H | H | CH₂CF₃ |
| 576 | F | Me | 1 | OH | H | Cl | H | H | CH₂CF₃ |
| 577 | F | Me | 0 | OCH₃ | H | Cl | H | H | CH₂CF₃ |
| 578 | F | Me | 1 | OCH₃ | H | Cl | H | H | CH₂CF₃ |
| 579 | F | Me | 0 | OCH₂CH₃ | H | Cl | H | H | CH₂CF₃ |
| 580 | F | Me | 1 | OCH₂CH₃ | H | Cl | H | H | CH₂CF₃ |
| 581 | F | Me | 0 | OCH₂CH₂CH₃ | H | Cl | H | H | CH₂CF₃ |
| 582 | F | Me | 1 | OCH₂CH₂CH₃ | H | Cl | H | H | CH₂CF₃ |
| 583 | F | Me | 0 | OCH₂CH₂CH₂CH₃ | H | Cl | H | H | CH₂CF₃ |
| 584 | F | Me | 1 | OCH₂CH₂CH₂CH₃ | H | Cl | H | H | CH₂CF₃ |
| 585 | F | Me | 0 | OCH₂CH₂CH₂CH₂CH₃ | H | Cl | H | H | CH₂CF₃ |
| 586 | F | Me | 1 | SH | H | Cl | H | H | CH₂CF₃ |
| 587 | F | Me | 0 | SH | H | Cl | H | H | CH₂CF₃ |
| 588 | F | Me | 1 | SCH₃ | H | Cl | H | H | CH₂CF₃ |
| 589 | F | Me | 0 | SCH₃ | H | Cl | H | H | CH₂CF₃ |
| 590 | F | Me | 1 | SCH₂CH₃ | H | Cl | H | H | CH₂CF₃ |
| 591 | F | Me | 0 | SCH₂CH₃ | H | Cl | H | H | CH₂CF₃ |
| 592 | F | Me | 1 | SCH₂CH₂CH₃ | H | Cl | H | H | CH₂CF₃ |
| 593 | F | Me | 0 | SCH₂CH₂CH₃ | H | Cl | H | H | CH₂CF₃ |
| 594 | F | Me | 1 | SCH₂CH₂CH₂CH₃ | H | Cl | H | H | CH₂CF₃ |
| 595 | F | Me | 0 | SCH₂CH₂CH₂CH₃ | H | Cl | H | H | CH₂CF₃ |
| 596 | F | Me | 1 | SCH₂CH₂CH₂CH₂CH₃ | H | Cl | H | H | CH₂CF₃ |
| 597 | Me | Me | 0 | Me | H | Cl | H | H | CH₂CF₃ |
| 598 | Me | Me | 1 | Me | H | Cl | H | H | CH₂CF₃ |
| 599 | Me | Me | 0 | Et | H | Cl | H | H | CH₂CF₃ |
| 600 | Me | Me | 1 | Et | H | Cl | H | H | CH₂CF₃ |
| 601 | Me | Me | 0 | nPropyl | H | Cl | H | H | CH₂CF₃ |
| 602 | Me | Me | 1 | nPropyl | H | Cl | H | H | CH₂CF₃ |
| 603 | Me | Me | 0 | isopropyl | H | Cl | H | H | CH₂CF₃ |
| 604 | Me | Me | 1 | isopropyl | H | Cl | H | H | CH₂CF₃ |
| 605 | Me | Me | 0 | nButyl | H | Cl | H | H | CH₂CF₃ |
| 606 | Me | Me | 1 | nButyl | H | Cl | H | H | CH₂CF₃ |
| 607 | Me | Me | 0 | nPentyl | H | Cl | H | H | CH₂CF₃ |
| 608 | Me | Me | 1 | nPentyl | H | Cl | H | H | CH₂CF₃ |
| 609 | Me | Me | 0 | nHexyl | H | Cl | H | H | CH₂CF₃ |
| 610 | Me | Me | 1 | nHexyl | H | Cl | H | H | CH₂CF₃ |
| 611 | Me | Me | 0 | nHeptyl | H | Cl | H | H | CH₂CF₃ |
| 612 | Me | Me | 1 | nHeptyl | H | Cl | H | H | CH₂CF₃ |
| 613 | Me | Me | 0 | nOctyl | H | Cl | H | H | CH₂CF₃ |
| 614 | Me | Me | 1 | nOctyl | H | Cl | H | H | CH₂CF₃ |

TABLE 1-continued

List of compounds

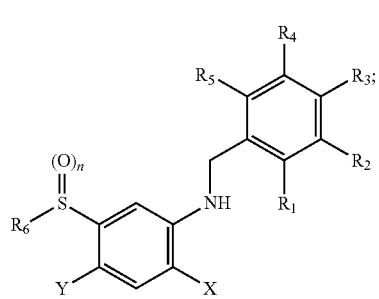

I

| No. | X | Y | n | $R_1$ | $R_2$ | $R_3$ | $R_4$ | $R_5$ | $R_6$ |
|---|---|---|---|---|---|---|---|---|---|
| 615 | Me | Me | 0 | nNonyl | H | Cl | H | H | $CH_2CF_3$ |
| 616 | Me | Me | 1 | nNonyl | H | Cl | H | H | $CH_2CF_3$ |
| 617 | Me | Me | 0 | nDecyl | H | Cl | H | H | $CH_2CF_3$ |
| 618 | Me | Me | 1 | nDecyl | H | Cl | H | H | $CH_2CF_3$ |
| 619 | Me | Me | 0 | F | H | Cl | H | H | $CH_2CF_3$ |
| 620 | Me | Me | 1 | F | H | Cl | H | H | $CH_2CF_3$ |
| 621 | Me | Me | 0 | Cl | H | Cl | H | H | $CH_2CF_3$ |
| 622 | Me | Me | 1 | Cl | H | Cl | H | H | $CH_2CF_3$ |
| 623 | Me | Me | 0 | Br | H | Cl | H | H | $CH_2CF_3$ |
| 624 | Me | Me | 1 | Br | H | Cl | H | H | $CH_2CF_3$ |
| 625 | Me | Me | 0 | I | H | Cl | H | H | $CH_2CF_3$ |
| 626 | Me | Me | 1 | I | H | Cl | H | H | $CH_2CF_3$ |
| 627 | Me | Me | 0 | CN | H | Cl | H | H | $CH_2CF_3$ |
| 628 | Me | Me | 1 | CN | H | Cl | H | H | $CH_2CF_3$ |
| 629 | Me | Me | 0 | $NO_2$ | H | Cl | H | H | $CH_2CF_3$ |
| 630 | Me | Me | 1 | $NO_2$ | H | Cl | H | H | $CH_2CF_3$ |
| 631 | Me | Me | 0 | $NH_2$ | H | Cl | H | H | $CH_2CF_3$ |
| 632 | Me | Me | 1 | $NH_2$ | H | Cl | H | H | $CH_2CF_3$ |
| 633 | Me | Me | 0 | $CH_2OH$ | H | Cl | H | H | $CH_2CF_3$ |
| 634 | Me | Me | 1 | $CH_2OH$ | H | Cl | H | H | $CH_2CF_3$ |
| 635 | Me | Me | 0 | $COCH_3$ | H | Cl | H | H | $CH_2CF_3$ |
| 636 | Me | Me | 1 | $COCH_3$ | H | Cl | H | H | $CH_2CF_3$ |
| 637 | Me | Me | 0 | $COCH_2CH_3$ | H | Cl | H | H | $CH_2CF_3$ |
| 638 | Me | Me | 1 | $COCH_2CH_3$ | H | Cl | H | H | $CH_2CF_3$ |
| 639 | Me | Me | 0 | $COCH_2CH_2CH_3$ | H | Cl | H | H | $CH_2CF_3$ |
| 640 | Me | Me | 1 | $COCH_2CH_2CH_3$ | H | Cl | H | H | $CH_2CF_3$ |
| 641 | Me | Me | 0 | $COCH_2CH_2CH_2CH_3$ | H | Cl | H | H | $CH_2CF_3$ |
| 642 | Me | Me | 1 | $COCH_2CH_2CH_2CH_3$ | H | Cl | H | H | $CH_2CF_3$ |
| 643 | Me | Me | 0 | $COCH_2CH_2CH_2CH_2CH_3$ | H | Cl | H | H | $CH_2CF_3$ |
| 644 | Me | Me | 1 | $COCH_2CH_2CH_2CH_2CH_3$ | H | Cl | H | H | $CH_2CF_3$ |
| 645 | Me | Me | 0 | COOH | H | Cl | H | H | $CH_2CF_3$ |
| 646 | Me | Me | 1 | COOH | H | Cl | H | H | $CH_2CF_3$ |
| 647 | Me | Me | 0 | $CO_2CH_3$ | H | Cl | H | H | $CH_2CF_3$ |
| 648 | Me | Me | 1 | $CO_2CH_3$ | H | Cl | H | H | $CH_2CF_3$ |
| 649 | Me | Me | 0 | $CO_2CH_2CH_3$ | H | Cl | H | H | $CH_2CF_3$ |
| 650 | Me | Me | 1 | $CO_2CH_2CH_3$ | H | Cl | H | H | $CH_2CF_3$ |
| 651 | Me | Me | 0 | $CO_2CH_2CH_2CH_3$ | H | Cl | H | H | $CH_2CF_3$ |
| 652 | Me | Me | 1 | $CO_2CH_2CH_2CH_3$ | H | Cl | H | H | $CH_2CF_3$ |
| 653 | Me | Me | 0 | $CO_2CH_2CH_2CH_2CH_3$ | H | Cl | H | H | $CH_2CF_3$ |
| 654 | Me | Me | 1 | $CO_2CH_2CH_2CH_2CH_3$ | H | Cl | H | H | $CH_2CF_3$ |
| 655 | Me | Me | 0 | $CO_2CH_2CH_2CH_2CH_2CH_3$ | H | Cl | H | H | $CH_2CF_3$ |
| 656 | Me | Me | 1 | $CO_2CH_2CH_2CH_2CH_2CH_3$ | H | Cl | H | H | $CH_2CF_3$ |
| 657 | Me | Me | 0 | $CO_2CH(CH_3)_2$ | H | Cl | H | H | $CH_2CF_3$ |
| 658 | Me | Me | 1 | $CO_2CH(CH_3)_2$ | H | Cl | H | H | $CH_2CF_3$ |
| 659 | Me | Me | 0 | $CO_2CH_2CH(CH_3)_2$ | H | Cl | H | H | $CH_2CF_3$ |
| 660 | Me | Me | 1 | $CO_2CH_2CH(CH_3)_2$ | H | Cl | H | H | $CH_2CF_3$ |
| 661 | Me | Me | 0 | $CO_2CH=CH_2$ | H | Cl | H | H | $CH_2CF_3$ |
| 662 | Me | Me | 1 | $CO_2CH=CH_2$ | H | Cl | H | H | $CH_2CF_3$ |
| 663 | Me | Me | 0 | $CO_2CH_2CH=CH_2$ | H | Cl | H | H | $CH_2CF_3$ |
| 664 | Me | Me | 1 | $CO_2CH_2CH=CH_2$ | H | Cl | H | H | $CH_2CF_3$ |
| 665 | Me | Me | 0 | $CO_2CH_2CF_3$ | H | Cl | H | H | $CH_2CF_3$ |
| 666 | Me | Me | 1 | $CO_2CH_2CF_3$ | H | Cl | H | H | $CH_2CF_3$ |
| 667 | Me | Me | 0 | $CO_2CH_2CH_2Cl$ | H | Cl | H | H | $CH_2CF_3$ |
| 668 | Me | Me | 1 | $CO_2CH_2CH_2Cl$ | H | Cl | H | H | $CH_2CF_3$ |
| 669 | Me | Me | 0 | $CO_2CH_2CH_2Br$ | H | Cl | H | H | $CH_2CF_3$ |
| 670 | Me | Me | 1 | $CO_2CH_2CH_2Br$ | H | Cl | H | H | $CH_2CF_3$ |
| 671 | Me | Me | 0 | $CO_2CH_2OCH_3$ | H | Cl | H | H | $CH_2CF_3$ |
| 672 | Me | Me | 1 | $CO_2CH_2COCH_3$ | H | Cl | H | H | $CH_2CF_3$ |
| 673 | Me | Me | 0 | $CONH_2$ | H | Cl | H | H | $CH_2CF_3$ |
| 674 | Me | Me | 1 | $CONH_2$ | H | Cl | H | H | $CH_2CF_3$ |
| 675 | Me | Me | 0 | $CONHCH_3$ | H | Cl | H | H | $CH_2CF_3$ |

TABLE 1-continued

List of compounds

I

| No. | X | Y | n | R$_1$ | R$_2$ | R$_3$ | R$_4$ | R$_5$ | R$_6$ |
|---|---|---|---|---|---|---|---|---|---|
| 676 | Me | Me | 1 | CONHCH$_3$ | H | Cl | H | H | CH$_2$CF$_3$ |
| 677 | Me | Me | 0 | CON(CH$_3$)$_2$ | H | Cl | H | H | CH$_2$CF$_3$ |
| 678 | Me | Me | 1 | CON(CH$_3$)$_2$ | H | Cl | H | H | CH$_2$CF$_3$ |
| 679 | Me | Me | 0 | CONHCH$_2$CH$_3$ | H | Cl | H | H | CH$_2$CF$_3$ |
| 680 | Me | Me | 1 | CONHCH$_2$CH$_3$ | H | Cl | H | H | CH$_2$CF$_3$ |
| 681 | Me | Me | 0 | CONHCH$_2$CH$_2$CH$_3$ | H | Cl | H | H | CH$_2$CF$_3$ |
| 682 | Me | Me | 1 | CONHCH$_2$CH$_2$CH$_3$ | H | Cl | H | H | CH$_2$CF$_3$ |
| 683 | Me | Me | 0 | CONHCH$_2$CH$_2$CH$_2$CH$_3$ | H | Cl | H | H | CH$_2$CF$_3$ |
| 684 | Me | Me | 1 | CONHCH$_2$CH$_2$CH$_2$CH$_3$ | H | Cl | H | H | CH$_2$CF$_3$ |
| 685 | Me | Me | 0 | CONHCH$_2$CH$_2$CH$_2$CH$_2$CH$_3$ | H | Cl | H | H | CH$_2$CF$_3$ |
| 686 | Me | Me | 1 | CONHCH$_2$CH$_2$CH$_2$CH$_2$CH$_3$ | H | Cl | H | H | CH$_2$CF$_3$ |
| 687 | Me | Me | 0 | OH | H | Cl | H | H | CH$_2$CF$_3$ |
| 688 | Me | Me | 1 | OH | H | Cl | H | H | CH$_2$CF$_3$ |
| 689 | Me | Me | 0 | OCH$_3$ | H | Cl | H | H | CH$_2$CF$_3$ |
| 690 | Me | Me | 1 | OCH$_3$ | H | Cl | H | H | CH$_2$CF$_3$ |
| 691 | Me | Me | 0 | OCH$_2$CH$_3$ | H | Cl | H | H | CH$_2$CF$_3$ |
| 692 | Me | Me | 1 | OCH$_2$CH$_3$ | H | Cl | H | H | CH$_2$CF$_3$ |
| 693 | Me | Me | 0 | OCH$_2$CH$_2$CH$_3$ | H | Cl | H | H | CH$_2$CF$_3$ |
| 694 | Me | Me | 1 | OCH$_2$CH$_2$CH$_3$ | H | Cl | H | H | CH$_2$CF$_3$ |
| 695 | Me | Me | 0 | OCH$_2$CH$_2$CH$_2$CH$_3$ | H | Cl | H | H | CH$_2$CF$_3$ |
| 696 | Me | Me | 1 | OCH$_2$CH$_2$CH$_2$CH$_3$ | H | Cl | H | H | CH$_2$CF$_3$ |
| 697 | Me | Me | 0 | OCH$_2$CH$_2$CH$_2$CH$_2$CH$_3$ | H | Cl | H | H | CH$_2$CF$_3$ |
| 698 | Me | Me | 1 | SH | H | Cl | H | H | CH$_2$CF$_3$ |
| 699 | Me | Me | 0 | SH | H | Cl | H | H | CH$_2$CF$_3$ |
| 700 | Me | Me | 1 | SCH$_3$ | H | Cl | H | H | CH$_2$CF$_3$ |
| 701 | Me | Me | 0 | SCH$_3$ | H | Cl | H | H | CH$_2$CF$_3$ |
| 702 | Me | Me | 1 | SCH$_2$CH$_3$ | H | Cl | H | H | CH$_2$CF$_3$ |
| 703 | Me | Me | 0 | SCH$_2$CH$_3$ | H | Cl | H | H | CH$_2$CF$_3$ |
| 704 | Me | Me | 1 | SCH$_2$CH$_2$CH$_3$ | H | Cl | H | H | CH$_2$CF$_3$ |
| 705 | Me | Me | 0 | SCH$_2$CH$_2$CH$_3$ | H | Cl | H | H | CH$_2$CF$_3$ |
| 706 | Me | Me | 1 | SCH$_2$CH$_2$CH$_2$CH$_3$ | H | Cl | H | H | CH$_2$CF$_3$ |
| 707 | Me | Me | 0 | SCH$_2$CH$_2$CH$_2$CH$_3$ | H | Cl | H | H | CH$_2$CF$_3$ |
| 708 | Me | Me | 1 | SCH$_2$CH$_2$CH$_2$CH$_2$CH$_3$ | H | Cl | H | H | CH$_2$CF$_3$ |
| 709 | F | Me | 0 | H | H | F | H | H | CH$_2$CF$_3$ |
| 710 | F | Me | 1 | H | H | F | H | H | CH$_2$CF$_3$ |
| 711 | F | Me | 0 | H | H | Cl | H | H | CH$_2$CF$_3$ |
| 712 | F | Me | 1 | H | H | Cl | H | H | CH$_2$CF$_3$ |
| 713 | F | Me | 0 | H | H | Br | H | H | CH$_2$CF$_3$ |
| 714 | F | Me | 1 | H | H | Br | H | H | CH$_2$CF$_3$ |
| 715 | F | Me | 0 | H | H | I | H | H | CH$_2$CF$_3$ |
| 716 | F | Me | 1 | H | H | I | H | H | CH$_2$CF$_3$ |
| 717 | F | Me | 0 | H | H | OH | H | H | CH$_2$CF$_3$ |
| 718 | F | Me | 1 | H | H | OH | H | H | CH$_2$CF$_3$ |
| 719 | F | Me | 0 | H | H | NH$_2$ | H | H | CH$_2$CF$_3$ |
| 720 | F | Me | 1 | H | H | NH$_2$ | H | H | CH$_2$CF$_3$ |
| 721 | F | Me | 0 | H | H | CN | H | H | CH$_2$CF$_3$ |
| 722 | F | Me | 1 | H | H | CN | H | H | CH$_2$CF$_3$ |
| 723 | F | Me | 0 | H | H | NO$_2$ | H | H | CH$_2$CF$_3$ |
| 724 | F | Me | 1 | H | H | NO$_2$ | H | H | CH$_2$CF$_3$ |
| 725 | F | Me | 0 | H | H | CF$_3$ | H | H | CH$_2$CF$_3$ |
| 726 | F | Me | 1 | H | H | CF$_3$ | H | H | CH$_2$CF$_3$ |
| 727 | F | Me | 0 | H | H | COCH$_3$ | H | H | CH$_2$CF$_3$ |
| 728 | F | Me | 1 | H | H | COCH$_3$ | H | H | CH$_2$CF$_3$ |
| 729 | F | Me | 0 | H | H | COCH$_2$CH$_3$ | H | H | CH$_2$CF$_3$ |
| 730 | F | Me | 1 | H | H | COCH$_2$CH$_3$ | H | H | CH$_2$CF$_3$ |
| 731 | F | Me | 0 | H | H | COCH$_2$CH$_2$CH$_3$ | H | H | CH$_2$CF$_3$ |
| 732 | F | Me | 1 | H | H | COCH$_2$CH$_2$CH$_3$ | H | H | CH$_2$CF$_3$ |
| 733 | F | Me | 0 | H | H | COCH$_2$CH$_2$CH$_2$CH$_3$ | H | H | CH$_2$CF$_3$ |
| 734 | F | Me | 1 | H | H | COCH$_2$CH$_2$CH$_2$CH$_3$ | H | H | CH$_2$CF$_3$ |
| 735 | F | Me | 0 | H | H | COCH$_2$CH$_2$CH$_2$CH$_2$CH$_3$ | H | H | CH$_2$CF$_3$ |
| 736 | F | Me | 1 | H | H | COCH$_2$CH$_2$CH$_2$CH$_2$CH$_3$ | H | H | CH$_2$CF$_3$ |

TABLE 1-continued

List of compounds

I

| No. | X | Y | n | $R_1$ | $R_2$ | $R_3$ | $R_4$ | $R_5$ | $R_6$ |
|---|---|---|---|---|---|---|---|---|---|
| 737 | F | Me | 0 | H | H | COOH | H | H | $CH_2CF_3$ |
| 738 | F | Me | 1 | H | H | COOH | H | H | $CH_2CF_3$ |
| 739 | F | Me | 0 | H | H | $CO_2CH_3$ | H | H | $CH_2CF_3$ |
| 740 | F | Me | 1 | H | H | $CO_2CH_3$ | H | H | $CH_2CF_3$ |
| 741 | F | Me | 0 | H | H | F | H | H | $CH_2CF_3$ |
| 742 | F | Me | 1 | H | H | F | H | H | $CH_2CF_3$ |
| 743 | F | Me | 0 | H | H | Cl | H | H | $CH_2CF_3$ |
| 744 | F | Me | 1 | H | H | Cl | H | H | $CH_2CF_3$ |
| 745 | F | Me | 0 | H | H | Br | H | H | $CH_2CF_3$ |
| 746 | F | Me | 1 | H | H | Br | H | H | $CH_2CF_3$ |
| 747 | F | Me | 0 | H | H | I | H | H | $CH_2CF_3$ |
| 748 | F | Me | 1 | H | H | I | H | H | $CH_2CF_3$ |
| 749 | F | Me | 0 | H | H | OH | H | H | $CH_2CF_3$ |
| 750 | F | Me | 1 | H | H | OH | H | H | $CH_2CF_3$ |
| 751 | F | Me | 0 | H | H | $NH_2$ | H | H | $CH_2CF_3$ |
| 752 | F | Me | 1 | H | H | $NH_2$ | H | H | $CH_2CF_3$ |
| 753 | F | Me | 0 | H | H | CN | H | H | $CH_2CF_3$ |
| 754 | F | Me | 1 | H | H | CN | H | H | $CH_2CF_3$ |
| 755 | F | Me | 0 | H | H | $NO_2$ | H | H | $CH_2CF_3$ |
| 756 | F | Me | 1 | H | H | $NO_2$ | H | H | $CH_2CF_3$ |
| 757 | F | Me | 0 | H | H | $COCH_3$ | H | H | $CH_2CF_3$ |
| 758 | F | Me | 1 | H | H | $COCH_3$ | H | H | $CH_2CF_3$ |
| 759 | F | Me | 0 | H | H | $COCH_2CH_3$ | H | H | $CH_2CF_3$ |
| 760 | F | Me | 1 | H | H | $COCH_2CH_3$ | H | H | $CH_2CF_3$ |
| 761 | F | Me | 0 | H | H | $COCH_2CH_2CH_3$ | H | H | $CH_2CF_3$ |
| 762 | F | Me | 1 | H | H | $COCH_2CH_2CH_3$ | H | H | $CH_2CF_3$ |
| 763 | F | Me | 0 | H | H | $COCH_2CH_2CH_2CH_3$ | H | H | $CH_2CF_3$ |
| 764 | F | Me | 1 | H | H | $COCH_2CH_2CH_2CH_3$ | H | H | $CH_2CF_3$ |
| 765 | F | Me | 0 | H | H | $COCH_2CH_2CH_2CH_2CH_3$ | H | H | $CH_2CF_3$ |
| 766 | F | Me | 1 | H | H | $COCH_2CH_2CH_2CH_2CH_3$ | H | H | $CH_2CF_3$ |
| 767 | F | Me | 0 | Me | H | H | H | H | nPropyl |
| 768 | F | Me | 1 | Me | H | H | H | H | nPropyl |
| 769 | F | Me | 0 | Et | H | H | H | H | nPropyl |
| 770 | F | Me | 1 | Et | H | H | H | H | nPropyl |
| 771 | F | Me | 0 | nPropyl | H | H | H | H | nPropyl |
| 772 | F | Me | 1 | nPropyl | H | H | H | H | nPropyl |
| 773 | F | Me | 0 | isopropyl | H | H | H | H | nPropyl |
| 774 | F | Me | 1 | isopropyl | H | H | H | H | nPropyl |
| 775 | F | Me | 0 | nButyl | H | H | H | H | nPropyl |
| 776 | F | Me | 1 | nButyl | H | H | H | H | nPropyl |
| 777 | F | Me | 0 | nPentyl | H | H | H | H | nPropyl |
| 778 | F | Me | 1 | nPentyl | H | H | H | H | nPropyl |
| 779 | F | Me | 0 | nHexyl | H | H | H | H | nPropyl |
| 780 | F | Me | 1 | nHexyl | H | H | H | H | nPropyl |
| 781 | F | Me | 0 | nHeptyl | H | H | H | H | nPropyl |
| 782 | F | Me | 1 | nHeptyl | H | H | H | H | nPropyl |
| 783 | F | Me | 0 | nOctyl | H | H | H | H | nPropyl |
| 784 | F | Me | 1 | nOctyl | H | H | H | H | nPropyl |
| 785 | F | Me | 0 | nNonyl | H | H | H | H | nPropyl |
| 786 | F | Me | 1 | nNonyl | H | H | H | H | nPropyl |
| 787 | F | Me | 0 | nDecyl | H | H | H | H | nPropyl |
| 788 | F | Me | 1 | nDecyl | H | H | H | H | nPropyl |
| 789 | F | Me | 0 | F | H | H | H | H | nPropyl |
| 790 | F | Me | 1 | F | H | H | H | H | nPropyl |
| 791 | F | Me | 0 | Cl | H | H | H | H | nPropyl |
| 792 | F | Me | 1 | Cl | H | H | H | H | nPropyl |
| 793 | F | Me | 0 | Br | H | H | H | H | nPropyl |
| 794 | F | Me | 1 | Br | H | H | H | H | nPropyl |
| 795 | F | Me | 0 | I | H | H | H | H | nPropyl |
| 796 | F | Me | 1 | I | H | H | H | H | nPropyl |
| 797 | F | Me | 0 | CN | H | H | H | H | nPropyl |

TABLE 1-continued

List of compounds

I

| No. | X | Y | n | R$_1$ | R$_2$ | R$_3$ | R$_4$ | R$_5$ | R$_6$ |
|---|---|---|---|---|---|---|---|---|---|
| 798 | F | Me | 1 | CN | H | H | H | H | nPropyl |
| 799 | F | Me | 0 | NO$_2$ | H | H | H | H | nPropyl |
| 800 | F | Me | 1 | NO$_2$ | H | H | H | H | nPropyl |
| 801 | F | Me | 0 | NH$_2$ | H | H | H | H | nPropyl |
| 802 | F | Me | 1 | NH$_2$ | H | H | H | H | nPropyl |
| 803 | F | Me | 0 | CH$_2$OH | H | H | H | H | nPropyl |
| 804 | F | Me | 1 | CH$_2$OH | H | H | H | H | nPropyl |
| 805 | F | Me | 0 | COCH$_3$ | H | H | H | H | nPropyl |
| 806 | F | Me | 1 | COCH$_3$ | H | H | H | H | nPropyl |
| 807 | F | Me | 0 | COCH$_2$CH$_3$ | H | H | H | H | nPropyl |
| 808 | F | Me | 1 | COCH$_2$CH$_3$ | H | H | H | H | nPropyl |
| 809 | F | Me | 0 | COCH$_2$CH$_2$CH$_3$ | H | H | H | H | nPropyl |
| 810 | F | Me | 1 | COCH$_2$CH$_2$CH$_3$ | H | H | H | H | nPropyl |
| 811 | F | Me | 0 | COCH$_2$CH$_2$CH$_2$CH$_3$ | H | H | H | H | nPropyl |
| 812 | F | Me | 1 | COCH$_2$CH$_2$CH$_2$CH$_3$ | H | H | H | H | nPropyl |
| 813 | F | Me | 0 | COCH$_2$CH$_2$CH$_2$CH$_2$CH$_3$ | H | H | H | H | nPropyl |
| 814 | F | Me | 1 | COCH$_2$CH$_2$CH$_2$CH$_2$CH$_3$ | H | H | H | H | nPropyl |
| 815 | F | Me | 0 | COOH | H | H | H | H | nPropyl |
| 816 | F | Me | 1 | COOH | H | H | H | H | nPropyl |
| 817 | F | Me | 0 | CO$_2$CH$_3$ | H | H | H | H | nPropyl |
| 818 | F | Me | 1 | CO$_2$CH$_3$ | H | H | H | H | nPropyl |
| 819 | F | Me | 0 | CO$_2$CH$_2$CH$_3$ | H | H | H | H | nPropyl |
| 820 | F | Me | 1 | CO$_2$CH$_2$CH$_3$ | H | H | H | H | nPropyl |
| 821 | F | Me | 0 | CO$_2$CH$_2$CH$_2$CH$_3$ | H | H | H | H | nPropyl |
| 822 | F | Me | 1 | CO$_2$CH$_2$CH$_2$CH$_3$ | H | H | H | H | nPropyl |
| 823 | F | Me | 0 | CO$_2$CH$_2$CH$_2$CH$_2$CH$_3$ | H | H | H | H | nPropyl |
| 824 | F | Me | 1 | CO$_2$CH$_2$CH$_2$CH$_2$CH$_3$ | H | H | H | H | nPropyl |
| 825 | F | Me | 0 | CO$_2$CH$_2$CH$_2$CH$_2$CH$_2$CH$_3$ | H | H | H | H | nPropyl |
| 826 | F | Me | 1 | CO$_2$CH$_2$CH$_2$CH$_2$CH$_2$CH$_3$ | H | H | H | H | nPropyl |
| 827 | F | Me | 0 | CO$_2$CH(CH$_3$)$_2$ | H | H | H | H | nPropyl |
| 828 | F | Me | 1 | CO$_2$CH(CH$_3$)$_2$ | H | H | H | H | nPropyl |
| 829 | F | Me | 0 | CO$_2$CH$_2$CH(CH$_3$)$_2$ | H | H | H | H | nPropyl |
| 830 | F | Me | 1 | CO$_2$CH$_2$CH(CH$_3$)$_2$ | H | H | H | H | nPropyl |
| 831 | F | Me | 0 | CO$_2$CH=CH$_2$ | H | H | H | H | nPropyl |
| 832 | F | Me | 1 | CO$_2$CH=CH$_2$ | H | H | H | H | nPropyl |
| 833 | F | Me | 0 | CO$_2$CH$_2$CH=CH$_2$ | H | H | H | H | nPropyl |
| 834 | F | Me | 1 | CO$_2$CH$_2$CH=CH$_2$ | H | H | H | H | nPropyl |
| 835 | F | Me | 0 | CO$_2$CH$_2$CF$_3$ | H | H | H | H | nPropyl |
| 836 | F | Me | 1 | CO$_2$CH$_2$CF$_3$ | H | H | H | H | nPropyl |
| 837 | F | Me | 0 | CO$_2$CH$_2$CH$_2$Cl | H | H | H | H | nPropyl |
| 838 | F | Me | 1 | CO$_2$CH$_2$CH$_2$Cl | H | H | H | H | nPropyl |
| 839 | F | Me | 0 | CO$_2$CH$_2$CH$_2$Br | H | H | H | H | nPropyl |
| 840 | F | Me | 1 | CO$_2$CH$_2$CH$_2$Br | H | H | H | H | nPropyl |
| 841 | F | Me | 0 | CO$_2$CH$_2$OCH$_3$ | H | H | H | H | nPropyl |
| 842 | F | Me | 1 | CO$_2$CH$_2$COCH$_3$ | H | H | H | H | nPropyl |
| 843 | F | Me | 0 | CONH$_2$ | H | H | H | H | nPropyl |
| 844 | F | Me | 1 | CONH$_2$ | H | H | H | H | nPropyl |
| 845 | F | Me | 0 | CONHCH$_3$ | H | H | H | H | nPropyl |
| 846 | F | Me | 1 | CONHCH$_3$ | H | H | H | H | nPropyl |
| 847 | F | Me | 0 | CON(CH$_3$)$_2$ | H | H | H | H | nPropyl |
| 848 | F | Me | 1 | CON(CH$_3$)$_2$ | H | H | H | H | nPropyl |
| 849 | F | Me | 0 | CONHCH$_2$CH$_3$ | H | H | H | H | nPropyl |
| 850 | F | Me | 1 | CONHCH$_2$CH$_3$ | H | H | H | H | nPropyl |
| 851 | F | Me | 0 | CONHCH$_2$CH$_2$CH$_3$ | H | H | H | H | nPropyl |
| 852 | F | Me | 1 | CONHCH$_2$CH$_2$CH$_3$ | H | H | H | H | nPropyl |
| 853 | F | Me | 0 | CONHCH$_2$CH$_2$CH$_2$CH$_3$ | H | H | H | H | nPropyl |
| 854 | F | Me | 1 | CONHCH$_2$CH$_2$CH$_2$CH$_3$ | H | H | H | H | nPropyl |
| 855 | F | Me | 0 | CONHCH$_2$CH$_2$CH$_2$CH$_2$CH$_3$ | H | H | H | H | nPropyl |
| 856 | F | Me | 1 | CONHCH$_2$CH$_2$CH$_2$CH$_2$CH$_3$ | H | H | H | H | nPropyl |
| 857 | F | Me | 0 | OH | H | H | H | H | nPropyl |
| 858 | F | Me | 1 | OH | H | H | H | H | nPropyl |

TABLE 1-continued

List of compounds

I

| No. | X | Y | n | R₁ | R₂ | R₃ | R₄ | R₅ | R₆ |
|---|---|---|---|---|---|---|---|---|---|
| 859 | F | Me | 0 | OCH₃ | H | H | H | H | nPropyl |
| 860 | F | Me | 1 | OCH₃ | H | H | H | H | nPropyl |
| 861 | F | Me | 0 | OCH₂CH₃ | H | H | H | H | nPropyl |
| 862 | F | Me | 1 | OCH₂CH₃ | H | H | H | H | nPropyl |
| 863 | F | Me | 0 | OCH₂CH₂CH₃ | H | H | H | H | nPropyl |
| 864 | F | Me | 1 | OCH₂CH₂CH₃ | H | H | H | H | nPropyl |
| 865 | F | Me | 0 | OCH₂CH₂CH₂CH₃ | H | H | H | H | nPropyl |
| 866 | F | Me | 1 | OCH₂CH₂CH₂CH₃ | H | H | H | H | nPropyl |
| 867 | F | Me | 0 | OCH₂CH₂CH₂CH₂CH₃ | H | H | H | H | nPropyl |
| 868 | F | Me | 1 | SH | H | H | H | H | nPropyl |
| 869 | F | Me | 0 | SH | H | H | H | H | nPropyl |
| 870 | F | Me | 1 | SCH₃ | H | H | H | H | nPropyl |
| 871 | F | Me | 0 | SCH₃ | H | H | H | H | nPropyl |
| 872 | F | Me | 1 | SCH₂CH₃ | H | H | H | H | nPropyl |
| 873 | F | Me | 0 | SCH₂CH₃ | H | H | H | H | nPropyl |
| 874 | F | Me | 1 | SCH₂CH₂CH₃ | H | H | H | H | nPropyl |
| 875 | F | Me | 0 | SCH₂CH₂CH₃ | H | H | H | H | nPropyl |
| 876 | F | Me | 1 | SCH₂CH₂CH₂CH₃ | H | H | H | H | nPropyl |
| 877 | F | Me | 0 | SCH₂CH₂CH₂CH₃ | H | H | H | H | nPropyl |
| 878 | F | Me | 1 | SCH₂CH₂CH₂CH₂CH₃ | H | H | H | H | nPropyl |
| 879 | Me | Me | 0 | Me | H | H | H | H | nPropyl |
| 880 | Me | Me | 1 | Me | H | H | H | H | nPropyl |
| 881 | Me | Me | 0 | Et | H | H | H | H | nPropyl |
| 882 | Me | Me | 1 | Et | H | H | H | H | nPropyl |
| 883 | Me | Me | 0 | nPropyl | H | H | H | H | nPropyl |
| 884 | Me | Me | 1 | nPropyl | H | H | H | H | nPropyl |
| 885 | Me | Me | 0 | isopropyl | H | H | H | H | nPropyl |
| 886 | Me | Me | 1 | isopropyl | H | H | H | H | nPropyl |
| 887 | Me | Me | 0 | nButyl | H | H | H | H | nPropyl |
| 888 | Me | Me | 1 | nButyl | H | H | H | H | nPropyl |
| 889 | Me | Me | 0 | nPentyl | H | H | H | H | nPropyl |
| 890 | Me | Me | 1 | nPentyl | H | H | H | H | nPropyl |
| 891 | Me | Me | 0 | nHexyl | H | H | H | H | nPropyl |
| 892 | Me | Me | 1 | nHexyl | H | H | H | H | nPropyl |
| 893 | Me | Me | 0 | nHeptyl | H | H | H | H | nPropyl |
| 894 | Me | Me | 1 | nHeptyl | H | H | H | H | nPropyl |
| 895 | Me | Me | 0 | nOctyl | H | H | H | H | nPropyl |
| 896 | Me | Me | 1 | nOctyl | H | H | H | H | nPropyl |
| 897 | Me | Me | 0 | nNonyl | H | H | H | H | nPropyl |
| 898 | Me | Me | 1 | nNonyl | H | H | H | H | nPropyl |
| 899 | Me | Me | 0 | nDecyl | H | H | H | H | nPropyl |
| 900 | Me | Me | 1 | nDecyl | H | H | H | H | nPropyl |
| 901 | Me | Me | 0 | F | H | H | H | H | nPropyl |
| 902 | Me | Me | 1 | F | H | H | H | H | nPropyl |
| 903 | Me | Me | 0 | Cl | H | H | H | H | nPropyl |
| 904 | Me | Me | 1 | Cl | H | H | H | H | nPropyl |
| 905 | Me | Me | 0 | Br | H | H | H | H | nPropyl |
| 906 | Me | Me | 1 | Br | H | H | H | H | nPropyl |
| 907 | Me | Me | 0 | I | H | H | H | H | nPropyl |
| 908 | Me | Me | 1 | I | H | H | H | H | nPropyl |
| 909 | Me | Me | 0 | CN | H | H | H | H | nPropyl |
| 910 | Me | Me | 1 | CN | H | H | H | H | nPropyl |
| 911 | Me | Me | 0 | NO₂ | H | H | H | H | nPropyl |
| 912 | Me | Me | 1 | NO₂ | H | H | H | H | nPropyl |
| 913 | Me | Me | 0 | NH₂ | H | H | H | H | nPropyl |
| 914 | Me | Me | 1 | NH₂ | H | H | H | H | nPropyl |
| 915 | Me | Me | 0 | CH₂OH | H | H | H | H | nPropyl |
| 916 | Me | Me | 1 | CH₂OH | H | H | H | H | nPropyl |
| 917 | Me | Me | 0 | COCH₃ | H | H | H | H | nPropyl |
| 918 | Me | Me | 1 | COCH₃ | H | H | H | H | nPropyl |
| 919 | Me | Me | 0 | COCH₂CH₃ | H | H | H | H | nPropyl |

TABLE 1-continued

List of compounds

I

| No. | X | Y | n | R₁ | R₂ | R₃ | R₄ | R₅ | R₆ |
|---|---|---|---|---|---|---|---|---|---|
| 920 | Me | Me | 1 | COCH$_2$CH$_3$ | H | H | H | H | nPropyl |
| 921 | Me | Me | 0 | COCH$_2$CH$_2$CH$_3$ | H | H | H | H | nPropyl |
| 922 | Me | Me | 1 | COCH$_2$CH$_2$CH$_3$ | H | H | H | H | nPropyl |
| 923 | Me | Me | 0 | COCH$_2$CH$_2$CH$_2$CH$_3$ | H | H | H | H | nPropyl |
| 924 | Me | Me | 1 | COCH$_2$CH$_2$CH$_2$CH$_3$ | H | H | H | H | nPropyl |
| 925 | Me | Me | 0 | COCH$_2$CH$_2$CH$_2$CH$_2$CH$_3$ | H | H | H | H | nPropyl |
| 926 | Me | Me | 1 | COCH$_2$CH$_2$CH$_2$CH$_2$CH$_3$ | H | H | H | H | nPropyl |
| 927 | Me | Me | 0 | COOH | H | H | H | H | nPropyl |
| 928 | Me | Me | 1 | COOH | H | H | H | H | nPropyl |
| 929 | Me | Me | 0 | CO$_2$CH$_3$ | H | H | H | H | nPropyl |
| 930 | Me | Me | 1 | CO$_2$CH$_3$ | H | H | H | H | nPropyl |
| 931 | Me | Me | 0 | CO$_2$CH$_2$CH$_3$ | H | H | H | H | nPropyl |
| 932 | Me | Me | 1 | CO$_2$CH$_2$CH$_3$ | H | H | H | H | nPropyl |
| 933 | Me | Me | 0 | CO$_2$CH$_2$CH$_2$CH$_3$ | H | H | H | H | nPropyl |
| 934 | Me | Me | 1 | CO$_2$CH$_2$CH$_2$CH$_3$ | H | H | H | H | nPropyl |
| 935 | Me | Me | 0 | CO$_2$CH$_2$CH$_2$CH$_2$CH$_3$ | H | H | H | H | nPropyl |
| 936 | Me | Me | 1 | CO$_2$CH$_2$CH$_2$CH$_2$CH$_3$ | H | H | H | H | nPropyl |
| 937 | Me | Me | 0 | CO$_2$CH$_2$CH$_2$CH$_2$CH$_2$CH$_3$ | H | H | H | H | nPropyl |
| 938 | Me | Me | 1 | CO$_2$CH$_2$CH$_2$CH$_2$CH$_2$CH$_3$ | H | H | H | H | nPropyl |
| 939 | Me | Me | 0 | CO$_2$CH(CH$_3$)$_2$ | H | H | H | H | nPropyl |
| 940 | Me | Me | 1 | CO$_2$CH(CH$_3$)$_2$ | H | H | H | H | nPropyl |
| 941 | Me | Me | 0 | CO$_2$CH$_2$CH(CH$_3$)$_2$ | H | H | H | H | nPropyl |
| 942 | Me | Me | 1 | CO$_2$CH$_2$CH(CH$_3$)$_2$ | H | H | H | H | nPropyl |
| 943 | Me | Me | 0 | CO$_2$CH=CH$_2$ | H | H | H | H | nPropyl |
| 944 | Me | Me | 1 | CO$_2$CH=CH$_2$ | H | H | H | H | nPropyl |
| 945 | Me | Me | 0 | CO$_2$CH$_2$CH=CH$_2$ | H | H | H | H | nPropyl |
| 946 | Me | Me | 1 | CO$_2$CH$_2$CH=CH$_2$ | H | H | H | H | nPropyl |
| 947 | Me | Me | 0 | CO$_2$CH$_2$CF$_3$ | H | H | H | H | nPropyl |
| 948 | Me | Me | 1 | CO$_2$CH$_2$CF$_3$ | H | H | H | H | nPropyl |
| 949 | Me | Me | 0 | CO$_2$CH$_2$CH$_2$Cl | H | H | H | H | nPropyl |
| 950 | Me | Me | 1 | CO$_2$CH$_2$CH$_2$Cl | H | H | H | H | nPropyl |
| 951 | Me | Me | 0 | CO$_2$CH$_2$CH$_2$Br | H | H | H | H | nPropyl |
| 952 | Me | Me | 1 | CO$_2$CH$_2$CH$_2$Br | H | H | H | H | nPropyl |
| 953 | Me | Me | 0 | CO$_2$CH$_2$OCH$_3$ | H | H | H | H | nPropyl |
| 954 | Me | Me | 1 | CO$_2$CH$_2$COCH$_3$ | H | H | H | H | nPropyl |
| 955 | Me | Me | 0 | CONH$_2$ | H | H | H | H | nPropyl |
| 956 | Me | Me | 1 | CONH$_2$ | H | H | H | H | nPropyl |
| 957 | Me | Me | 0 | CONHCH$_3$ | H | H | H | H | nPropyl |
| 958 | Me | Me | 1 | CONHCH$_3$ | H | H | H | H | nPropyl |
| 959 | Me | Me | 0 | CON(CH$_3$)$_2$ | H | H | H | H | nPropyl |
| 960 | Me | Me | 1 | CON(CH$_3$)$_2$ | H | H | H | H | nPropyl |
| 961 | Me | Me | 0 | CONHCH$_2$CH$_3$ | H | H | H | H | nPropyl |
| 962 | Me | Me | 1 | CONHCH$_2$CH$_3$ | H | H | H | H | nPropyl |
| 963 | Me | Me | 0 | CONHCH$_2$CH$_2$CH$_3$ | H | H | H | H | nPropyl |
| 964 | Me | Me | 1 | CONHCH$_2$CH$_2$CH$_3$ | H | H | H | H | nPropyl |
| 965 | Me | Me | 0 | CONHCH$_2$CH$_2$CH$_2$CH$_3$ | H | H | H | H | nPropyl |
| 966 | Me | Me | 1 | CONHCH$_2$CH$_2$CH$_2$CH$_3$ | H | H | H | H | nPropyl |
| 967 | Me | Me | 0 | CONHCH$_2$CH$_2$CH$_2$CH$_2$CH$_3$ | H | H | H | H | nPropyl |
| 968 | Me | Me | 1 | CONHCH$_2$CH$_2$CH$_2$CH$_2$CH$_3$ | H | H | H | H | nPropyl |
| 969 | Me | Me | 0 | OH | H | H | H | H | nPropyl |
| 970 | Me | Me | 1 | OH | H | H | H | H | nPropyl |
| 971 | Me | Me | 0 | OCH$_3$ | H | H | H | H | nPropyl |
| 972 | Me | Me | 1 | OCH$_3$ | H | H | H | H | nPropyl |
| 973 | Me | Me | 0 | OCH$_2$CH$_3$ | H | H | H | H | nPropyl |
| 974 | Me | Me | 1 | OCH$_2$CH$_3$ | H | H | H | H | nPropyl |
| 975 | Me | Me | 0 | OCH$_2$CH$_2$CH$_3$ | H | H | H | H | nPropyl |
| 976 | Me | Me | 1 | OCH$_2$CH$_2$CH$_3$ | H | H | H | H | nPropyl |
| 977 | Me | Me | 0 | OCH$_2$CH$_2$CH$_2$CH$_3$ | H | H | H | H | nPropyl |
| 978 | Me | Me | 1 | OCH$_2$CH$_2$CH$_2$CH$_3$ | H | H | H | H | nPropyl |
| 979 | Me | Me | 0 | OCH$_2$CH$_2$CH$_2$CH$_2$CH$_3$ | H | H | H | H | nPropyl |
| 980 | Me | Me | 1 | SH | H | H | H | H | nPropyl |

TABLE 1-continued

List of compounds

I

| No. | X | Y | n | R$_1$ | R$_2$ | R$_3$ | R$_4$ | R$_5$ | R$_6$ |
|---|---|---|---|---|---|---|---|---|---|
| 981 | Me | Me | 0 | SH | H | H | H | H | nPropyl |
| 982 | Me | Me | 1 | SCH$_3$ | H | H | H | H | nPropyl |
| 983 | Me | Me | 0 | SCH$_3$ | H | H | H | H | nPropyl |
| 984 | Me | Me | 1 | SCH$_2$CH$_3$ | H | H | H | H | nPropyl |
| 985 | Me | Me | 0 | SCH$_2$CH$_3$ | H | H | H | H | nPropyl |
| 986 | Me | Me | 1 | SCH$_2$CH$_2$CH$_3$ | H | H | H | H | nPropyl |
| 987 | Me | Me | 0 | SCH$_2$CH$_2$CH$_3$ | H | H | H | H | nPropyl |
| 988 | Me | Me | 1 | SCH$_2$CH$_2$CH$_2$CH$_3$ | H | H | H | H | nPropyl |
| 989 | Me | Me | 0 | SCH$_2$CH$_2$CH$_2$CH$_3$ | H | H | H | H | nPropyl |
| 990 | Me | Me | 1 | SCH$_2$CH$_2$CH$_2$CH$_2$CH$_3$ | H | H | H | H | nPropyl |
| 991 | F | Me | 0 | Me | H | H | H | H | CH$_2$CF$_3$ |
| 992 | F | Me | 1 | Me | H | H | H | H | CH$_2$CF$_3$ |
| 993 | F | Me | 0 | CF$_3$ | H | H | H | H | CH$_2$CF$_3$ |
| 994 | F | Me | 1 | CF$_3$ | H | H | H | H | CH$_2$CF$_3$ |
| 995 | F | Me | 0 | Et | H | H | H | H | CH$_2$CF$_3$ |
| 996 | F | Me | 1 | Et | H | H | H | H | CH$_2$CF$_3$ |
| 997 | F | Me | 0 | nPropyl | H | H | H | H | CH$_2$CF$_3$ |
| 998 | F | Me | 1 | nPropyl | H | H | H | H | CH$_2$CF$_3$ |
| 999 | F | Me | 0 | isopropyl | H | H | H | H | CH$_2$CF$_3$ |
| 1000 | F | Me | 1 | isopropyl | H | H | H | H | CH$_2$CF$_3$ |
| 1001 | F | Me | 0 | nButyl | H | H | H | H | CH$_2$CF$_3$ |
| 1002 | F | Me | 1 | nButyl | H | H | H | H | CH$_2$CF$_3$ |
| 1003 | F | Me | 0 | nPentyl | H | H | H | H | CH$_2$CF$_3$ |
| 1004 | F | Me | 1 | nPentyl | H | H | H | H | CH$_2$CF$_3$ |
| 1005 | F | Me | 0 | nHexyl | H | H | H | H | CH$_2$CF$_3$ |
| 1006 | F | Me | 1 | nHexyl | H | H | H | H | CH$_2$CF$_3$ |
| 1007 | F | Me | 0 | nHeptyl | H | H | H | H | CH$_2$CF$_3$ |
| 1008 | F | Me | 1 | nHeptyl | H | H | H | H | CH$_2$CF$_3$ |
| 1009 | F | Me | 0 | nOctyl | H | H | H | H | CH$_2$CF$_3$ |
| 1010 | F | Me | 1 | nOctyl | H | H | H | H | CH$_2$CF$_3$ |
| 1011 | F | Me | 0 | nNonyl | H | H | H | H | CH$_2$CF$_3$ |
| 1012 | F | Me | 1 | nNonyl | H | H | H | H | CH$_2$CF$_3$ |
| 1013 | F | Me | 0 | nDecyl | H | H | H | H | CH$_2$CF$_3$ |
| 1014 | F | Me | 1 | nDecyl | H | H | H | H | CH$_2$CF$_3$ |
| 1015 | F | Me | 0 | F | H | H | H | H | CH$_2$CF$_3$ |
| 1016 | F | Me | 1 | F | H | H | H | H | CH$_2$CF$_3$ |
| 1017 | F | Me | 0 | Cl | H | H | H | H | CH$_2$CF$_3$ |
| 1018 | F | Me | 1 | Cl | H | H | H | H | CH$_2$CF$_3$ |
| 1019 | F | Me | 0 | Br | H | H | H | H | CH$_2$CF$_3$ |
| 1020 | F | Me | 1 | Br | H | H | H | H | CH$_2$CF$_3$ |
| 1021 | F | Me | 0 | I | H | H | H | H | CH$_2$CF$_3$ |
| 1022 | F | Me | 1 | I | H | H | H | H | CH$_2$CF$_3$ |
| 1023 | F | Me | 0 | CN | H | H | H | H | CH$_2$CF$_3$ |
| 1024 | F | Me | 1 | CN | H | H | H | H | CH$_2$CF$_3$ |
| 1025 | F | Me | 0 | NO$_2$ | H | H | H | H | CH$_2$CF$_3$ |
| 1026 | F | Me | 1 | NO$_2$ | H | H | H | H | CH$_2$CF$_3$ |
| 1027 | F | Me | 0 | NH$_2$ | H | H | H | H | CH$_2$CF$_3$ |
| 1028 | F | Me | 1 | NH$_2$ | H | H | H | H | CH$_2$CF$_3$ |
| 1029 | F | Me | 0 | CH$_2$OH | H | H | H | H | CH$_2$CF$_3$ |
| 1030 | Cl | Cl | 1 | CH$_2$OH | H | H | H | H | CH$_2$CF$_3$ |
| 1031 | Cl | Cl | 0 | COCH$_3$ | H | H | H | H | CH$_2$CF$_3$ |
| 1032 | Cl | Cl | 1 | COCH$_3$ | H | H | H | H | CH$_2$CF$_3$ |
| 1033 | Cl | Cl | 0 | COCH$_2$CH$_3$ | H | H | H | H | CH$_2$CF$_3$ |
| 1034 | Cl | Cl | 1 | COCH$_2$CH$_3$ | H | H | H | H | CH$_2$CF$_3$ |
| 1035 | Cl | Cl | 0 | COCH$_2$CH$_2$CH$_3$ | H | H | H | H | CH$_2$CF$_3$ |
| 1036 | Cl | Cl | 1 | COCH$_2$CH$_2$CH$_3$ | H | H | H | H | CH$_2$CF$_3$ |
| 1037 | Cl | Cl | 0 | COCH$_2$CH$_2$CH$_2$CH$_3$ | H | H | H | H | CH$_2$CF$_3$ |
| 1038 | Cl | Cl | 1 | COCH$_2$CH$_2$CH$_2$CH$_3$ | H | H | H | H | CH$_2$CF$_3$ |
| 1039 | Cl | Cl | 0 | COCH$_2$CH$_2$CH$_2$CH$_2$CH$_3$ | H | H | H | H | CH$_2$CF$_3$ |
| 1040 | Cl | Cl | 1 | COCH$_2$CH$_2$CH$_2$CH$_2$CH$_3$ | H | H | H | H | CH$_2$CF$_3$ |
| 1041 | Cl | Cl | 0 | COOH | H | H | H | H | CH$_2$CF$_3$ |

TABLE 1-continued

List of compounds

I

| No. | X | Y | n | $R_1$ | $R_2$ | $R_3$ | $R_4$ | $R_5$ | $R_6$ |
|---|---|---|---|---|---|---|---|---|---|
| 1042 | Cl | Cl | 1 | COOH | H | H | H | H | $CH_2CF_3$ |
| 1043 | Cl | Cl | 0 | $CO_2CH_3$ | H | H | H | H | $CH_2CF_3$ |
| 1044 | Cl | Cl | 1 | $CO_2CH_3$ | H | H | H | H | $CH_2CF_3$ |
| 1045 | Cl | Cl | 0 | $CO_2CH_2CH_3$ | H | H | H | H | $CH_2CF_3$ |
| 1046 | Cl | Cl | 1 | $CO_2CH_2CH_3$ | H | H | H | H | $CH_2CF_3$ |
| 1047 | Cl | Cl | 0 | $CO_2CH_2CH_2CH_3$ | H | H | H | H | $CH_2CF_3$ |
| 1048 | Cl | Cl | 1 | $CO_2CH_2CH_2CH_3$ | H | H | H | H | $CH_2CF_3$ |
| 1049 | Cl | Cl | 0 | $CO_2CH_2CH_2CH_2CH_3$ | H | H | H | H | $CH_2CF_3$ |
| 1050 | Cl | Cl | 1 | $CO_2CH_2CH_2CH_2CH_3$ | H | H | H | H | $CH_2CF_3$ |
| 1051 | Cl | Cl | 0 | $CO_2CH_2CH_2CH_2CH_2CH_3$ | H | H | H | H | $CH_2CF_3$ |
| 1052 | Cl | Cl | 1 | $CO_2CH_2CH_2CH_2CH_2CH_3$ | H | H | H | H | $CH_2CF_3$ |
| 1053 | Cl | Cl | 0 | $CO_2CH(CH_3)_2$ | H | H | H | H | $CH_2CF_3$ |
| 1054 | Cl | Cl | 1 | $CO_2CH(CH_3)_2$ | H | H | H | H | $CH_2CF_3$ |
| 1055 | Cl | Cl | 0 | $CO_2CH_2CH(CH_3)_2$ | H | H | H | H | $CH_2CF_3$ |
| 1056 | Cl | Cl | 1 | $CO_2CH_2CH(CH_3)_2$ | H | H | H | H | $CH_2CF_3$ |
| 1057 | Cl | Cl | 0 | $CO_2CH=CH_2$ | H | H | H | H | $CH_2CF_3$ |
| 1058 | Cl | Cl | 1 | $CO_2CH=CH_2$ | H | H | H | H | $CH_2CF_3$ |
| 1059 | Cl | Cl | 0 | $CO_2CH_2CH=CH_2$ | H | H | H | H | $CH_2CF_3$ |
| 1060 | Cl | Cl | 1 | $CO_2CH_2CH=CH_2$ | H | H | H | H | $CH_2CF_3$ |
| 1061 | Cl | Cl | 0 | $CO_2CH_2CF_3$ | H | H | H | H | $CH_2CF_3$ |
| 1062 | Cl | Cl | 1 | $CO_2CH_2CF_3$ | H | H | H | H | $CH_2CF_3$ |
| 1063 | Cl | Cl | 0 | $CO_2CH_2CH_2Cl$ | H | H | H | H | $CH_2CF_3$ |
| 1064 | Cl | Cl | 1 | $CO_2CH_2CH_2Cl$ | H | H | H | H | $CH_2CF_3$ |
| 1065 | Cl | Cl | 0 | $CO_2CH_2CH_2Br$ | H | H | H | H | $CH_2CF_3$ |
| 1066 | Cl | Cl | 1 | $CO_2CH_2CH_2Br$ | H | H | H | H | $CH_2CF_3$ |
| 1067 | Cl | Cl | 0 | $CO_2CH_2OCH_3$ | H | H | H | H | $CH_2CF_3$ |
| 1068 | Cl | Cl | 1 | $CO_2CH_2COCH_3$ | H | H | H | H | $CH_2CF_3$ |
| 1069 | Cl | Cl | 0 | $CONH_2$ | H | H | H | H | $CH_2CF_3$ |
| 1070 | Cl | Cl | 1 | $CONH_2$ | H | H | H | H | $CH_2CF_3$ |
| 1071 | Cl | Cl | 0 | $CONHCH_3$ | H | H | H | H | $CH_2CF_3$ |
| 1072 | Cl | Cl | 1 | $CONHCH_3$ | H | H | H | H | $CH_2CF_3$ |
| 1073 | Cl | Cl | 0 | $CON(CH_3)_2$ | H | H | H | H | $CH_2CF_3$ |
| 1074 | Cl | Cl | 1 | $CON(CH_3)_2$ | H | H | H | H | $CH_2CF_3$ |
| 1075 | Cl | Cl | 0 | $CONHCH_2CH_3$ | H | H | H | H | $CH_2CF_3$ |
| 1076 | Cl | Cl | 1 | $CONHCH_2CH_3$ | H | H | H | H | $CH_2CF_3$ |
| 1077 | Cl | Cl | 0 | $CONHCH_2CH_2CH_3$ | H | H | H | H | $CH_2CF_3$ |
| 1078 | Cl | Cl | 1 | $CONHCH_2CH_2CH_3$ | H | H | H | H | $CH_2CF_3$ |
| 1079 | Cl | Cl | 0 | $CONHCH_2CH_2CH_2CH_3$ | H | H | H | H | $CH_2CF_3$ |
| 1080 | Cl | Cl | 1 | $CONHCH_2CH_2CH_2CH_3$ | H | H | H | H | $CH_2CF_3$ |
| 1081 | Cl | Cl | 0 | $CONHCH_2CH_2CH_2CH_2CH_3$ | H | H | H | H | $CH_2CF_3$ |
| 1082 | Cl | Cl | 1 | $CONHCH_2CH_2CH_2CH_2CH_3$ | H | H | H | H | $CH_2CF_3$ |
| 1083 | Cl | Cl | 0 | OH | H | H | H | H | $CH_2CF_3$ |
| 1084 | Cl | Cl | 1 | OH | H | H | H | H | $CH_2CF_3$ |
| 1085 | Cl | Cl | 0 | $OCH_3$ | H | H | H | H | $CH_2CF_3$ |
| 1086 | Cl | Cl | 1 | $OCH_3$ | H | H | H | H | $CH_2CF_3$ |
| 1087 | Cl | Cl | 0 | $OCH_2CH_3$ | H | H | H | H | $CH_2CF_3$ |
| 1088 | Cl | Cl | 1 | $OCH_2CH_3$ | H | H | H | H | $CH_2CF_3$ |
| 1089 | Cl | Cl | 0 | $OCH_2CH_2CH_3$ | H | H | H | H | $CH_2CF_3$ |
| 1090 | Cl | Cl | 1 | $OCH_2CH_2CH_3$ | H | H | H | H | $CH_2CF_3$ |
| 1091 | Cl | Cl | 0 | $OCH_2CH_2CH_2CH_3$ | H | H | H | H | $CH_2CF_3$ |
| 1092 | Cl | Cl | 1 | $OCH_2CH_2CH_2CH_3$ | H | H | H | H | $CH_2CF_3$ |
| 1093 | Cl | Cl | 0 | $OCH_2CH_2CH_2CH_2CH_3$ | H | H | H | H | $CH_2CF_3$ |
| 1094 | Cl | Cl | 1 | SH | H | H | H | H | $CH_2CF_3$ |
| 1095 | Cl | Cl | 0 | SH | H | H | H | H | $CH_2CF_3$ |
| 1096 | Cl | Cl | 1 | $SCH_3$ | H | H | H | H | $CH_2CF_3$ |
| 1097 | Cl | Cl | 0 | $SCH_3$ | H | H | H | H | $CH_2CF_3$ |
| 1098 | Cl | Cl | 1 | $SCH_2CH_3$ | H | H | H | H | $CH_2CF_3$ |
| 1099 | Cl | Cl | 0 | $SCH_2CH_3$ | H | H | H | H | $CH_2CF_3$ |
| 1100 | Cl | Cl | 1 | $SCH_2CH_2CH_3$ | H | H | H | H | $CH_2CF_3$ |
| 1101 | Cl | Cl | 0 | $SCH_2CH_2CH_3$ | H | H | H | H | $CH_2CF_3$ |
| 1102 | Cl | Cl | 1 | $SCH_2CH_2CH_2CH_3$ | H | H | H | H | $CH_2CF_3$ |

TABLE 1-continued

List of compounds

I

| No. | X | Y | n | R₁ | R₂ | R₃ | R₄ | R₅ | R₆ |
|---|---|---|---|---|---|---|---|---|---|
| 1103 | Cl | Cl | 0 | SCH₂CH₂CH₂CH₃ | H | H | H | H | CH₂CF₃ |
| 1104 | Cl | Cl | 1 | SCH₂CH₂CH₂CH₂CH₃ | H | H | H | H | CH₂CF₃ |
| 1105 | F | Me | 0 | H | H | H | H | H | CH₂CF₃ |
| 1106 | F | Me | 1 | H | H | H | H | H | CH₂CF₃ |
| 1107 | F | Me | 0 | OCF3 | H | H | H | H | CH₂CF₃ |
| 1108 | F | Me | 1 | OCF3 | H | H | H | H | CH₂CF₃ |
| 1109 | F | Me | 0 | H | H | OCH₃ | H | H | CH₂CF₃ |
| 1110 | F | Me | 1 | H | H | OCH₃ | H | H | CH₂CF₃ |
| 1111 | F | Me | 0 | CO₂CH₃ | H | CO₂CH₃ | H | H | CH₂CF₃ |
| 1112 | F | Me | 1 | CO₂CH₃ | H | CO₂CH₃ | H | H | CH₂CF₃ |
| 1113 | F | Me | 0 | CO₂CH₃ | H | F | H | H | nPropyl |
| 1114 | F | Me | 1 | CO₂CH₃ | H | F | H | H | nPropyl |
| 1115 | F | Me | 0 | CO₂CH₃ | H | Cl | H | H | nPropyl |
| 1116 | F | Me | 1 | CO₂CH₃ | H | Cl | H | H | nPropyl |
| 1117 | F | Me | 0 | CO₂CH₃ | H | Br | H | H | CH₂CF₃ |
| 1118 | F | Me | 1 | CO₂CH₃ | H | Br | H | H | CH₂CF₃ |
| 1119 | F | Me | 0 | CO₂CH₃ | H | I | H | H | CH₂CF₃ |
| 1120 | F | Me | 1 | CO₂CH₃ | H | I | H | H | CH₂CF₃ |
| 1121 | F | Me | 0 | CO₂CH₃ | H | OH | H | H | CH₂CF₃ |
| 1122 | F | Me | 1 | CO₂CH₃ | H | OH | H | H | CH₂CF₃ |
| 1123 | F | Me | 0 | CO₂CH₃ | H | NH₂ | H | H | CH₂CF₃ |
| 1124 | F | Me | 1 | CO₂CH₃ | H | NH₂ | H | H | CH₂CF₃ |
| 1125 | F | Me | 0 | CO₂CH₃ | H | CN | H | H | CH₂CF₃ |
| 1126 | F | Me | 1 | CO₂CH₃ | H | CN | H | H | CH₂CF₃ |
| 1127 | F | Me | 0 | CO₂CH₃ | H | NO₂ | H | H | CH₂CF₃ |
| 1128 | F | Me | 1 | CO₂CH₃ | H | NO₂ | H | H | CH₂CF₃ |
| 1129 | F | Me | 0 | CO₂CH₃ | H | COCH₃ | H | H | CH₂CF₃ |
| 1130 | F | Me | 1 | CO₂CH₃ | H | COCH₃ | H | H | CH₂CF₃ |
| 1131 | F | Me | 0 | CO₂CH₃ | H | OCH₃ | H | H | CH₂CF₃ |
| 1132 | F | Me | 1 | CO₂CH₃ | H | OCH₃ | H | H | CH₂CF₃ |
| 1133 | F | Me | 0 | CO₂CH₃ | H | OCH₂CH₃ | H | H | CH₂CF₃ |
| 1134 | F | Me | 1 | CO₂CH₃ | H | OCH₂CH₃ | H | H | CH₂CF₃ |
| 1135 | F | Me | 0 | CO₂CH₃ | H | OPh | H | H | CH₂CF₃ |
| 1136 | F | Me | 1 | CO₂CH₃ | H | OPh | H | H | CH₂CF₃ |
| 1137 | Me | Me | 0 | CO₂CH₃ | H | CO₂CH₃ | H | H | CH₂CF₃ |
| 1138 | Me | Me | 1 | CO₂CH₃ | H | CO₂CH₃ | H | H | CH₂CF₃ |
| 1139 | Me | Me | 0 | CO₂CH₃ | H | F | H | H | CH₂CF₃ |
| 1140 | Me | Me | 1 | CO₂CH₃ | H | F | H | H | CH₂CF₃ |
| 1141 | Me | Me | 0 | CO₂CH₃ | H | Cl | H | H | CH₂CF₃ |
| 1142 | Me | Me | 1 | CO₂CH₃ | H | Cl | H | H | CH₂CF₃ |
| 1143 | Me | Me | 0 | CO₂CH₃ | H | Br | H | H | CH₂CF₃ |
| 1144 | Me | Me | 1 | CO₂CH₃ | H | Br | H | H | CH₂CF₃ |
| 1145 | Me | Me | 0 | CO₂CH₃ | H | I | H | H | CH₂CF₃ |
| 1146 | Me | Me | 1 | CO₂CH₃ | H | I | H | H | CH₂CF₃ |
| 1147 | Me | Me | 0 | CO₂CH₃ | H | OH | H | H | CH₂CF₃ |
| 1148 | Me | Me | 1 | CO₂CH₃ | H | OH | H | H | CH₂CF₃ |
| 1149 | Me | Me | 0 | CO₂CH₃ | H | NH₂ | H | H | CH₂CF₃ |
| 1150 | Me | Me | 1 | CO₂CH₃ | H | NH₂ | H | H | CH₂CF₃ |
| 1151 | Me | Me | 0 | CO₂CH₃ | H | CN | H | H | CH₂CF₃ |
| 1152 | Me | Me | 1 | CO₂CH₃ | H | CN | H | H | CH₂CF₃ |
| 1153 | Me | Me | 0 | CO₂CH₃ | H | NO₂ | H | H | CH₂CF₃ |
| 1154 | Me | Me | 1 | CO₂CH₃ | H | NO₂ | H | H | CH₂CF₃ |
| 1155 | Me | Me | 0 | CO₂CH₃ | H | COCH₃ | H | H | CH₂CF₃ |
| 1156 | Me | Me | 1 | CO₂CH₃ | H | COCH₃ | H | H | CH₂CF₃ |
| 1157 | Me | Me | 0 | CO₂CH₃ | H | OCH₃ | H | H | CH₂CF₃ |
| 1158 | Me | Me | 1 | CO₂CH₃ | H | OCH₃ | H | H | CH₂CF₃ |
| 1159 | Me | Me | 0 | CO₂CH₃ | H | OCH₂CH₃ | H | H | CH₂CF₃ |
| 1160 | Me | Me | 1 | CO₂CH₃ | H | OCH₂CH₃ | H | H | CH₂CF₃ |
| 1161 | Me | Me | 0 | CO₂CH₃ | H | OPh | H | H | CH₂CF₃ |
| 1162 | Me | Me | 1 | CO₂CH₃ | H | OPh | H | H | CH₂CF₃ |
| 1163 | F | Cl | 0 | CO₂CH₃ | H | CO₂CH₃ | H | H | CH₂CF₃ |

TABLE 1-continued

List of compounds

I

| No. | X | Y | n | $R_1$ | $R_2$ | $R_3$ | $R_4$ | $R_5$ | $R_6$ |
|---|---|---|---|---|---|---|---|---|---|
| 1164 | F | Cl | 1 | $CO_2CH_3$ | H | $CO_2CH_3$ | H | H | $CH_2CF_3$ |
| 1165 | F | Cl | 0 | $CO_2CH_3$ | H | F | H | H | $CH_2CF_3$ |
| 1166 | F | Cl | 1 | $CO_2CH_3$ | H | F | H | H | $CH_2CF_3$ |
| 1167 | F | Cl | 0 | $CO_2CH_3$ | H | Cl | H | H | $CH_2CF_3$ |
| 1168 | F | Cl | 1 | $CO_2CH_3$ | H | Cl | H | H | $CH_2CF_3$ |
| 1169 | F | Cl | 0 | $CO_2CH_3$ | H | Br | H | H | $CH_2CF_3$ |
| 1170 | F | Cl | 1 | $CO_2CH_3$ | H | Br | H | H | $CH_2CF_3$ |
| 1171 | F | Cl | 0 | $CO_2CH_3$ | H | I | H | H | $CH_2CF_3$ |
| 1172 | F | Cl | 1 | $CO_2CH_3$ | H | I | H | H | $CH_2CF_3$ |
| 1173 | F | Cl | 0 | $CO_2CH_3$ | H | OH | H | H | $CH_2CF_3$ |
| 1174 | F | Cl | 1 | $CO_2CH_3$ | H | OH | H | H | $CH_2CF_3$ |
| 1175 | F | Cl | 0 | $CO_2CH_3$ | H | $NH_2$ | H | H | $CH_2CF_3$ |
| 1176 | F | Cl | 1 | $CO_2CH_3$ | H | $NH_2$ | H | H | $CH_2CF_3$ |
| 1177 | F | Cl | 0 | $CO_2CH_3$ | H | CN | H | H | $CH_2CF_3$ |
| 1178 | F | Cl | 1 | $CO_2CH_3$ | H | CN | H | H | $CH_2CF_3$ |
| 1179 | F | Cl | 0 | $CO_2CH_3$ | H | $NO_2$ | H | H | $CH_2CF_3$ |
| 1180 | F | Cl | 1 | $CO_2CH_3$ | H | $NO_2$ | H | H | $CH_2CF_3$ |
| 1181 | F | Cl | 0 | $CO_2CH_3$ | H | $COCH_3$ | H | H | $CH_2CF_3$ |
| 1182 | F | Cl | 1 | $CO_2CH_3$ | H | $COCH_3$ | H | H | $CH_2CF_3$ |
| 1183 | F | Cl | 0 | $CO_2CH_3$ | H | $OCH_3$ | H | H | $CH_2CF_3$ |
| 1184 | F | Cl | 1 | $CO_2CH_3$ | H | $OCH_3$ | H | H | $CH_2CF_3$ |
| 1185 | F | Cl | 0 | $CO_2CH_3$ | H | $OCH_2CH_3$ | H | H | $CH_2CF_3$ |
| 1186 | F | Cl | 1 | $CO_2CH_3$ | H | $OCH_2CH_3$ | H | H | $CH_2CF_3$ |
| 1187 | F | Cl | 0 | $CO_2CH_3$ | H | OPh | H | H | $CH_2CF_3$ |
| 1188 | F | Cl | 1 | $CO_2CH_3$ | H | OPh | H | H | $CH_2CF_3$ |
| 1189 | F | Cl | 1 | $CH_2OH$ | H | H | H | H | $CH_2CF_3$ |
| 1190 | F | Cl | 0 | $COCH_3$ | H | H | H | H | $CH_2CF_3$ |
| 1191 | F | Cl | 1 | $COCH_3$ | H | H | H | H | $CH_2CF_3$ |
| 1192 | F | Cl | 0 | $COCH_2CH_3$ | H | H | H | H | $CH_2CF_3$ |
| 1193 | F | Cl | 1 | $COCH_2CH_3$ | H | H | H | H | $CH_2CF_3$ |
| 1194 | F | Cl | 0 | $COCH_2CH_2CH_3$ | H | H | H | H | $CH_2CF_3$ |
| 1195 | F | Cl | 1 | $COCH_2CH_2CH_3$ | H | H | H | H | $CH_2CF_3$ |
| 1196 | F | Cl | 0 | $COCH_2CH_2CH_2CH_3$ | H | H | H | H | $CH_2CF_3$ |
| 1197 | F | Cl | 1 | $COCH_2CH_2CH_2CH_3$ | H | H | H | H | $CH_2CF_3$ |
| 1198 | F | Cl | 0 | $COCH_2CH_2CH_2CH_2CH_3$ | H | H | H | H | $CH_2CF_3$ |
| 1199 | F | Cl | 1 | $COCH_2CH_2CH_2CH_2CH_3$ | H | H | H | H | $CH_2CF_3$ |
| 1200 | F | Cl | 0 | COOH | H | H | H | H | $CH_2CF_3$ |
| 1201 | F | Cl | 1 | COOH | H | H | H | H | $CH_2CF_3$ |
| 1202 | F | Cl | 0 | $CO_2CH_3$ | H | H | H | H | $CH_2CF_3$ |
| 1203 | F | Cl | 1 | $CO_2CH_3$ | H | H | H | H | $CH_2CF_3$ |
| 1204 | F | Cl | 0 | $CO_2CH_2CH_3$ | H | H | H | H | $CH_2CF_3$ |
| 1205 | F | Cl | 1 | $CO_2CH_2CH_3$ | H | .H | H | H | $CH_2CF_3$ |
| 1206 | F | Cl | 0 | $CO_2CH_2CH_2CH_3$ | H | H | H | H | $CH_2CF_3$ |
| 1207 | F | Cl | 1 | $CO_2CH_2CH_2CH_3$ | H | H | H | H | $CH_2CF_3$ |
| 1208 | F | Cl | 0 | $CO_2CH_2CH_2CH_2CH_3$ | H | H | H | H | $CH_2CF_3$ |
| 1209 | F | Cl | 1 | $CO_2CH_2CH_2CH_2CH_3$ | H | H | H | H | $CH_2CF_3$ |
| 1210 | F | Cl | 0 | $CO_2CH_2CH_2CH_2CH_2CH_3$ | H | H | H | H | $CH_2CF_3$ |
| 1211 | F | Cl | 1 | $CO_2CH_2CH_2CH_2CH_2CH_3$ | H | H | H | H | $CH_2CF_3$ |
| 1212 | F | Cl | 0 | $CO_2CH(CH_3)_2$ | H | H | H | H | $CH_2CF_3$ |
| 1213 | F | Cl | 1 | $CO_2CH(CH_3)_2$ | H | H | H | H | $CH_2CF_3$ |
| 1214 | F | Cl | 0 | $CO_2CH_2CH(CH_3)_2$ | H | H | H | H | $CH_2CF_3$ |
| 1215 | F | Cl | 1 | $CO_2CH_2CH(CH_3)_2$ | H | H | H | H | $CH_2CF_3$ |
| 1216 | F | Cl | 0 | $CO_2CH=CH_2$ | H | H | H | H | $CH_2CF_3$ |
| 1217 | F | Cl | 1 | $CO_2CH=CH_2$ | H | H | H | H | $CH_2CF_3$ |
| 1218 | F | Cl | 0 | $CO_2CH_2CH=CH_2$ | H | H | H | H | $CH_2CF_3$ |
| 1219 | F | Cl | 1 | $CO_2CH_2CH=CH_2$ | H | H | H | H | $CH_2CF_3$ |
| 1220 | F | Cl | 0 | $CO_2CH_2CF_3$ | H | H | H | H | $CH_2CF_3$ |
| 1221 | F | Cl | 1 | $CO_2CH_2CF_3$ | H | H | H | H | $CH_2CF_3$ |
| 1222 | F | Cl | 0 | $CO_2CH_2CH_2Cl$ | H | H | H | H | $CH_2CF_3$ |
| 1223 | F | Cl | 1 | $CO_2CH_2CH_2Cl$ | H | H | H | H | $CH_2CF_3$ |
| 1224 | F | Cl | 0 | $CO_2CH_2CH_2Br$ | H | H | H | H | $CH_2CF_3$ |

TABLE 1-continued

List of compounds

| No. | X | Y | n | R₁ | R₂ | R₃ | R₄ | R₅ | R₆ |
|---|---|---|---|---|---|---|---|---|---|
| 1225 | F | Cl | 1 | CO₂CH₂CH₂Br | H | H | H | H | CH₂CF₃ |
| 1226 | F | Cl | 0 | CO₂CH₂OCH₃ | H | H | H | H | CH₂CF₃ |
| 1227 | F | Cl | 1 | CO₂CH₂COCH₃ | H | H | H | H | CH₂CF₃ |
| 1228 | F | Cl | 0 | CONH₂ | H | H | H | H | CH₂CF₃ |
| 1229 | F | Cl | 1 | CONH₂ | H | H | H | H | CH₂CF₃ |
| 1230 | F | Cl | 0 | CONHCH₃ | H | H | H | H | CH₂CF₃ |
| 1231 | F | Cl | 1 | CONHCH₃ | H | H | H | H | CH₂CF₃ |
| 1232 | F | Cl | 0 | CON(CH₃)₂ | H | H | H | H | CH₂CF₃ |
| 1233 | F | Cl | 1 | CON(CH₃)₂ | H | H | H | H | CH₂CF₃ |
| 1234 | F | Cl | 0 | CONHCH₂CH₃ | H | H | H | H | CH₂CF₃ |
| 1235 | F | Cl | 1 | CONHCH₂CH₃ | H | H | H | H | CH₂CF₃ |
| 1236 | F | Cl | 0 | CONHCH₂CH₂CH₃ | H | H | H | H | CH₂CF₃ |
| 1237 | F | Cl | 1 | CONHCH₂CH₂CH₃ | H | H | H | H | CH₂CF₃ |
| 1238 | F | Cl | 0 | CONHCH₂CH₂CH₂CH₃ | H | H | H | H | CH₂CF₃ |
| 1239 | F | Cl | 1 | CONHCH₂CH₂CH₂CH₃ | H | H | H | H | CH₂CF₃ |
| 1240 | F | Cl | 0 | CONHCH₂CH₂CH₂CH₂CH₃ | H | H | H | H | CH₂CF₃ |
| 1241 | F | Cl | 1 | CONHCH₂CH₂CH₂CH₂CH₃ | H | H | H | H | CH₂CF₃ |
| 1242 | F | Cl | 0 | OH | H | H | H | H | CH₂CF₃ |
| 1243 | F | Cl | 1 | OH | H | H | H | H | CH₂CF₃ |
| 1244 | F | Cl | 0 | OCH₃ | H | H | H | H | CH₂CF₃ |
| 1245 | F | Cl | 1 | OCH₃ | H | H | H | H | CH₂CF₃ |
| 1246 | F | Cl | 0 | OCH₂CH₃ | H | H | H | H | CH₂CF₃ |
| 1247 | F | Cl | 1 | OCH₂CH₃ | H | H | H | H | CH₂CF₃ |
| 1248 | F | Cl | 0 | OCH₂CH₂CH₃ | H | H | H | H | CH₂CF₃ |
| 1249 | F | Cl | 1 | OCH₂CH₂CH₃ | H | H | H | H | CH₂CF₃ |
| 1250 | F | Cl | 0 | OCH₂CH₂CH₂CH₃ | H | H | H | H | CH₂CF₃ |
| 1251 | F | Cl | 1 | OCH₂CH₂CH₂CH₃ | H | H | H | H | CH₂CF₃ |
| 1252 | F | Cl | 0 | SH | H | H | H | H | CH₂CF₃ |
| 1253 | F | Cl | 1 | SH | H | H | H | H | CH₂CF₃ |
| 1254 | F | Cl | 0 | SCH₃ | H | H | H | H | CH₂CF₃ |
| 1255 | F | Cl | 1 | SCH₃ | H | H | H | H | CH₂CF₃ |
| 1256 | F | Cl | 0 | SCH₂CH₃ | H | H | H | H | CH₂CF₃ |
| 1257 | F | Cl | 1 | SCH₂CH₃ | H | H | H | H | CH₂CF₃ |
| 1258 | F | Cl | 0 | SCH₂CH₂CH₃ | H | H | H | H | CH₂CF₃ |
| 1259 | F | Cl | 1 | SCH₂CH₂CH₃ | H | H | H | H | CH₂CF₃ |
| 1260 | F | Cl | 0 | SCH₂CH₂CH₂CH₃ | H | H | H | H | CH₂CF₃ |
| 1261 | F | Cl | 1 | SCH₂CH₂CH₂CH₃ | H | H | H | H | CH₂CF₃ |
| 1262 | F | Cl | 0 | SCH₂CH₂CH₂CH₂CH₃ | H | H | H | H | CH₂CF₃ |
| 1263 | F | Cl | 1 | SCH₂CH₂CH₂CH₂CH₃ | H | H | H | H | CH₂CF₃ |
| 1264 | F | Cl | 0 | SCH₂CF₃ | H | H | H | H | CH₂CF₃ |
| 1265 | F | Cl | 1 | SCH₂CF₃ | H | H | H | H | CH₂CF₃ |
| 1266 | F | Cl | 0 | SCH₂CH₂Cl | H | H | H | H | CH₂CF₃ |
| 1267 | F | Cl | 1 | SCH₂CH₂Cl | H | H | H | H | CH₂CF₃ |
| 1268 | F | Cl | 0 | SCH₂CH₂F | H | H | H | H | CH₂CF₃ |
| 1269 | F | Cl | 1 | SCH₂CH₂F | H | H | H | H | CH₂CF₃ |
| 1270 | F | Cl | 0 | SCH₂CHF₂ | H | H | H | H | CH₂CF₃ |
| 1271 | F | Cl | 1 | SCH₂CHF₂ | H | H | H | H | CH₂CF₃ |
| 1272 | F | Cl | 0 | S(O)CH₂CH₃ | H | H | H | H | CH₂CF₃ |
| 1273 | F | Cl | 1 | S(O)CH₂CH₃ | H | H | H | H | CH₂CF₃ |
| 1274 | F | Cl | 0 | S(O)CH₂CF₃ | H | H | H | H | CH₂CF₃ |
| 1275 | F | Cl | 1 | S(O)CH₂CF₃ | H | H | H | H | CH₂CF₃ |
| 1276 | F | Cl | 0 | S(O)CH₂CH₂Cl | H | H | H | H | CH₂CF₃ |
| 1277 | F | Cl | 1 | S(O)CH₂CH₂Cl | H | H | H | H | CH₂CF₃ |
| 1278 | F | Cl | 0 | S(O)CH₂CH₂F | H | H | H | H | CH₂CF₃ |
| 1279 | F | Cl | 1 | S(O)CH₂CH₂F | H | H | H | H | CH₂CF₃ |
| 1280 | F | Cl | 0 | S(O)CH₂CHF₂ | H | H | H | H | CH₂CF₃ |
| 1281 | F | Cl | 1 | S(O)CH₂CHF₂ | H | H | H | H | CH₂CF₃ |
| 1282 | F | Cl | 0 | SCH₂CF₃ | H | F | H | H | CH₂CF₃ |
| 1283 | F | Cl | 1 | SCH₂CF₃ | H | F | H | H | CH₂CF₃ |
| 1284 | F | Cl | 0 | SCH₂CH₂Cl | H | F | H | H | CH₂CF₃ |
| 1285 | F | Cl | 1 | SCH₂CH₂Cl | H | F | H | H | CH₂CF₃ |

TABLE 1-continued

List of compounds

I

| No. | X | Y | n | R₁ | R₂ | R₃ | R₄ | R₅ | R₆ |
|---|---|---|---|---|---|---|---|---|---|
| 1286 | F | Cl | 0 | SCH₂CH₂F | H | F | H | H | CH₂CF₃ |
| 1287 | F | Cl | 1 | SCH₂CH₂F | H | F | H | H | CH₂CF₃ |
| 1288 | F | Cl | 0 | SCH₂CHF₂ | H | F | H | H | CH₂CF₃ |
| 1289 | F | Cl | 1 | SCH₂CHF₂ | H | F | H | H | CH₂CF₃ |
| 1290 | F | Cl | 0 | S(O)CH₂CH₃ | H | F | H | H | CH₂CF₃ |
| 1291 | F | Cl | 1 | S(O)CH₂CH₃ | H | F | H | H | CH₂CF₃ |
| 1292 | F | Cl | 0 | S(O)CH₂CF₃ | H | F | H | H | CH₂CF₃ |
| 1293 | F | Cl | 1 | S(O)CH₂CF₃ | H | F | H | H | CH₂CF₃ |
| 1294 | F | Cl | 0 | S(O)CH₂CH₂Cl | H | F | H | H | CH₂CF₃ |
| 1295 | F | Cl | 1 | S(O)CH₂CH₂Cl | H | F | H | H | CH₂CF₃ |
| 1296 | F | Cl | 0 | S(O)CH₂CH₂F | H | F | H | H | CH₂CF₃ |
| 1297 | F | Cl | 1 | S(O)CH₂CH₂F | H | F | H | H | CH₂CF₃ |
| 1298 | F | Cl | 0 | S(O)CH₂CHF₂ | H | F | H | H | CH₂CF₃ |
| 1299 | F | Cl | 1 | S(O)CH₂CHF₂ | H | F | H | H | CH₂CF₃ |
| 1300 | F | Me | 0 | SCH₂CF₃ | H | H | H | H | CH₂CF₃ |
| 1301 | F | Me | 1 | SCH₂CF₃ | H | H | H | H | CH₂CF₃ |
| 1302 | F | Me | 0 | SCH₂CH₂Cl | H | H | H | H | CH₂CF₃ |
| 1303 | F | Me | 1 | SCH₂CH₂Cl | H | H | H | H | CH₂CF₃ |
| 1304 | F | Me | 0 | SCH₂CH₂F | H | H | H | H | CH₂CF₃ |
| 1305 | F | Me | 1 | SCH₂CH₂F | H | H | H | H | CH₂CF₃ |
| 1306 | F | Me | 0 | SCH₂CHF₂ | H | H | H | H | CH₂CF₃ |
| 1307 | F | Me | 1 | SCH₂CHF₂ | H | H | H | H | CH₂CF₃ |
| 1308 | F | Me | 0 | S(O)CH₂CH₃ | H | H | H | H | CH₂CF₃ |
| 1309 | F | Me | 1 | S(O)CH₂CH₃ | H | H | H | H | CH₂CF₃ |
| 1310 | F | Me | 0 | S(O)CH₂CF₃ | H | H | H | H | CH₂CF₃ |
| 1311 | F | Me | 1 | S(O)CH₂CF3 | H | H | H | H | CH₂CF₃ |
| 1312 | F | Me | 0 | S(O)CH₂CH₂Cl | H | H | H | H | CH₂CF₃ |
| 1313 | F | Me | 1 | S(O)CH₂CH₂Cl | H | H | H | H | CH₂CF₃ |
| 1314 | F | Me | 0 | S(O)CH₂CH₂F | H | H | H | H | CH₂CF₃ |
| 1315 | F | Me | 1 | S(O)CH₂CH₂F | H | H | H | H | CH₂CF₃ |
| 1316 | F | Me | 0 | S(O)CH₂CHF₂ | H | H | H | H | CH₂CF₃ |
| 1317 | F | Me | 1 | S(O)CH₂CHF₂ | H | H | H | H | CH₂CF₃ |
| 1318 | F | Me | 0 | SCH₂CF₃ | H | F | H | H | CH₂CF₃ |
| 1319 | F | Me | 1 | SCH₂CF₃ | H | F | H | H | CH₂CF₃ |
| 1320 | F | Me | 0 | SCH₂CH₂Cl | H | F | H | H | CH₂CF₃ |
| 1321 | F | Me | 1 | SCH₂CH₂Cl | H | F | H | H | CH₂CF₃ |
| 1322 | F | Me | 0 | SCH₂CH₂F | H | F | H | H | CH₂CF₃ |
| 1323 | F | Me | 1 | SCH₂CH₂F | H | F | H | H | CH₂CF₃ |
| 1324 | F | Me | 0 | SCH₂CHF₂ | H | F | H | H | CH₂CF₃ |
| 1325 | F | Me | 1 | SCH₂CHF₂ | H | F | H | H | CH₂CF₃ |
| 1326 | F | Me | 0 | S(O)CH₂CH₃ | H | F | H | H | CH₂CF₃ |
| 1327 | F | Me | 1 | S(O)CH₂CH₃ | H | F | H | H | CH₂CF₃ |
| 1328 | F | Me | 0 | S(O)CH₂CF₃ | H | F | H | H | CH₂CF₃ |
| 1329 | F | Me | 1 | S(O)CH₂CF₃ | H | F | H | H | CH₂CF₃ |
| 1330 | F | Me | 0 | S(O)CH₂CH₂Cl | H | F | H | H | CH₂CF₃ |
| 1331 | F | Me | 1 | S(O)CH₂CH₂Cl | H | F | H | H | CH₂CF₃ |
| 1332 | F | Me | 0 | S(O)CH₂CH₂F | H | F | H | H | CH₂CF₃ |
| 1333 | F | Me | 1 | S(O)CH₂CH₂F | H | F | H | H | CH₂CF₃ |
| 1334 | F | Me | 0 | S(O)CH₂CHF₂ | H | F | H | H | CH₂CF₃ |
| 1335 | F | Me | 1 | S(O)CH₂CHF₂ | H | F | H | H | CH₂CF₃ |

The disclosure also provides a method for preparing the aryl sulfide, the method having the following synthesis route:

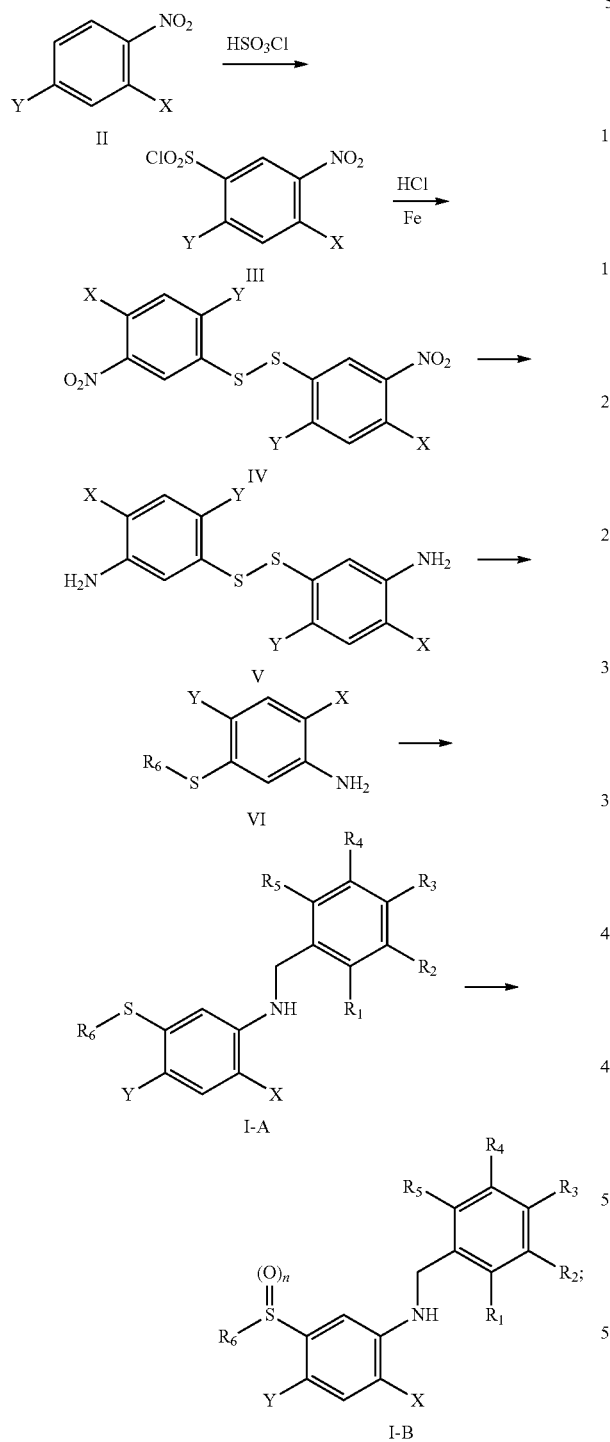

$R_1$, $R_2$, $R_3$, $R_4$, $R_5$, $R_6$, X, Y, n have the same definitions as mentioned above.

Specifically, the method comprises:

heating a mixture of a nitro compound II and chlorosulfonic acid to yield a sulfonyl chloride compound III; reducing the sulfonyl chloride compound III to yield a disulfide compound IV; reducing the disulfide compound IV with hydrogen or a metal to yield an amino compound V; contacting the amino compound V with an electrophilic reagent under alkaline conditions to yield an intermediate VI; contacting the intermediate VI with substituted benzyl bromide to yield a first compound I-A; and contacting the first compound I-A with m-chloroperoxybenzoic acid or hydrogen peroxide for oxidation reaction to yield a second compound I-B.

In a class of this embodiment, the intermediate VI is synthesized as follows:

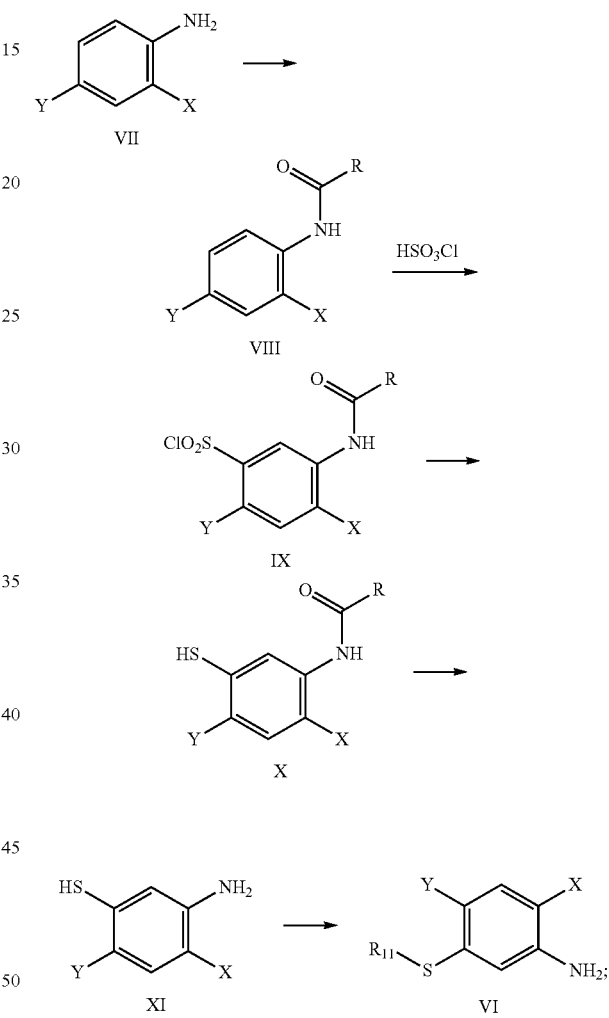

$R_6$, X, and Y have the same definitions as mentioned above.

Specifically, the synthesis of the intermediate VI comprises:

contacting an amino compound VII with acyl chloride or anhydride to yield an amino protected amide compound VIII; contacting the amino protected amide compound VIII with chlorosulfonic acid and heating to yield a compound IX; reducing the compound IX to yield a thiophenol compound X which is hydrolyzed under alkaline conditions and contacts with an electrophilic reagent for substitution reaction to yield the intermediate VI.

In a class of this embodiment, the compound XI is synthesized as follows:

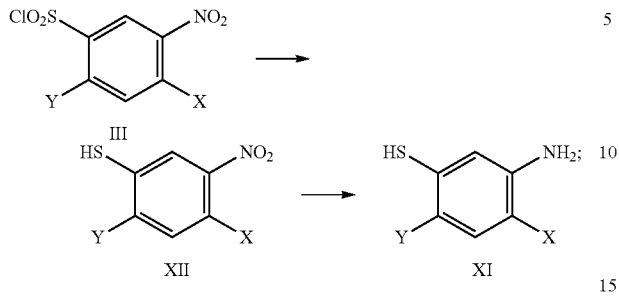

X and Y have the same definitions as mentioned above.

Specifically, the synthesis of the compound XI comprises: reducing the compound III to yield a thiophenol compound XII, and reducing the thiophenol compound XII to yield the compound XI.

The disclosure further provides a method for preparing the aryl sulfide, the method having the following synthesis route:

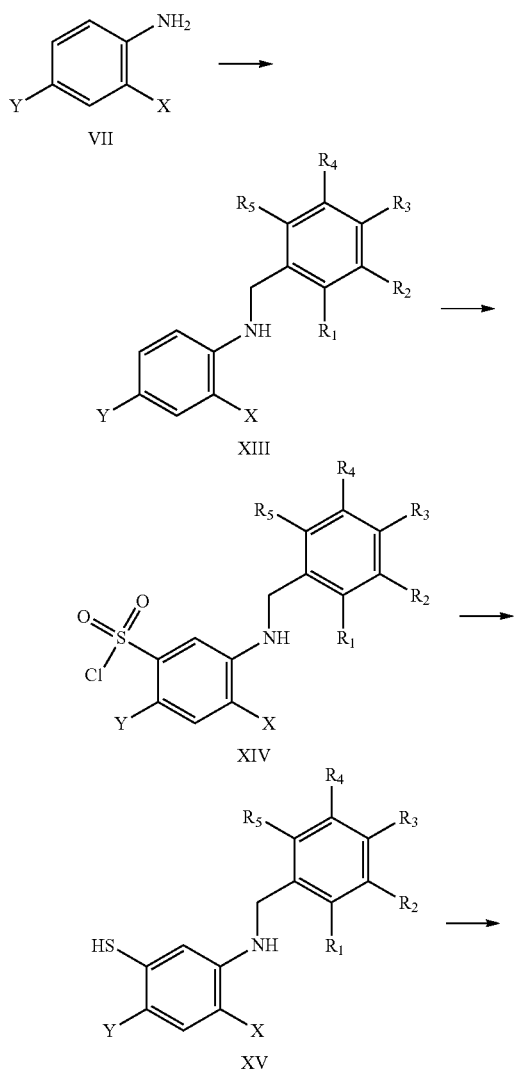

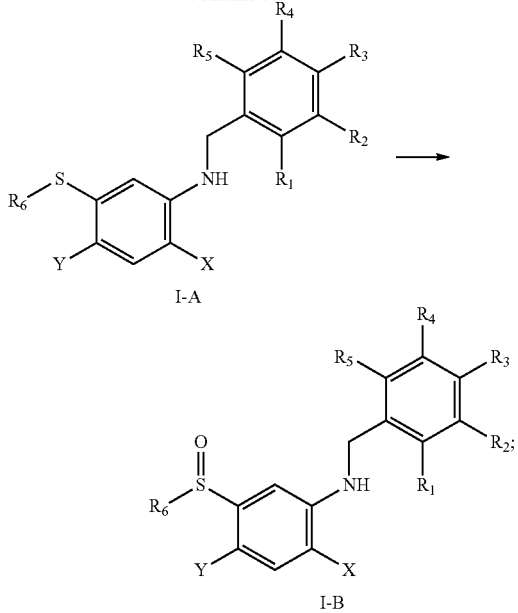

$R_1$, $R_2$, $R_3$, $R_4$, $R_5$, $R_6$, X, Y, and n have the same definitions as mentioned above.

Specifically, the method comprises:
preparing a benzylamine intermediate XIII from an intermediate VII; contacting the benzylamine intermediate XIII with sulfonyl chloride, followed by reduction reaction and substitution reaction, to yield a first compound I-A; and contacting the first compound I-A with m-chloroperoxybenzoic acid or hydrogen peroxide for oxidation reaction to yield a second compound I-B.

The agriculturally acceptable salt is a derivative of the compound represented by the formula I of the disclosure. Specifically, when a hydroxyl, carboxyl, or amino exists in the structure of the formula I, the hydroxyl, carboxyl, or amino reacts with a metal or organic base to form the salt, or reacts with an inorganic acid or organic acid to yield the salt, such as potassium salt, sodium salt, magnesium salt, or calcium salt. The organic bases can be triethylamine or diisopropylamine; the inorganic acid can be hydrochloric acid, sulfuric acid, hydrobromic acid, etc.; the organic acid can be formic acid, acetic acid, methanesulfonic acid, fumaric acid, maleic acid, etc.

The compound represented by general formula I (comprising I-A and I-B) of the disclosure has unexpected high acaricidal activity. Therefore, the technical scheme of the disclosure further includes the use of the compound represented by general formula I in the preparation of acaricide drugs in agriculture or other fields. In particular, the compound of general formula I has high activity to the following species (the objects listed below are only used to illustrate but not to limit the disclosure): Tetranychidae (*Tetranychus cinnabarinus, Panonychus citri, Tetranychus urticae, Panonychus ulmi, Tetranychus kanzawai, Tetranychus viennensis*), Acaridae, zodiaceae, Tetranychidae, *Myzus persicae*, nematodes, etc.

The abovementioned compounds have good properties and thus can be used to protect the crops and livestock in agriculture and horticulture from being damaged by mites.

To obtain the ideal effect, the dosage of the compound varies with various factors, such as the compound used, the to be protected crop, the type of pest, the degree of infection, the application method, the application environment, the dosage form, etc.

8 g to 3 kg of the compound per hectare can provide adequate control of mites.

The composition of the disclosure can be applied in the form of a preparation. The compound of the general formula I is dissolved or dispersed in a carrier as an active ingredient, or configured as a preparation, so that it is easier to disperse when used as acaricide. For example, the active substances can be made into wettable powder, water dispersible granule, suspension agent, water emulsion, water agent or emulsifiable concentrate. At least one liquid or solid carrier is added to the composition, and an appropriate surfactant can be added when necessary.

The disclosure provides a method for preventing mites: applying the composition of the disclosure to the mite or a growth medium thereof. In general, the suitable effective dose is 8 g to 1000 g/ha, and an optimal effective dose is 15 g to 300 g/ha.

For some applications, for example, in agriculture, one or more other insecticides, acaricides, fungicides, herbicides, plant growth regulators or fertilizers can be added to the acaricidal composition of the disclosure, thereby producing additional advantages and effects.

Understandably, various transformations and modifications can be made within the scope of the claims of the disclosure.

The following advantages are associated with the aryl sulfide comprising benzylamine of the disclosure:
1. The aryl sulfide comprising benzylamine exhibits excellent killing effects on various pests, especially on *Tetranychus urticae, Tetranychus kanzawai* and *Tetranychus Panonychus*
2. The compound exhibits good properties in protecting crops of agriculture and horticulture and livestock.

DETAILED DESCRIPTION

To further illustrate the disclosure, embodiments detailing an aryl sulfide comprising benzylamine and preparation method thereof are described below. It should be noted that the following embodiments are intended to describe and not to limit the disclosure.

Example 1

Preparation of N-(4-chloro-3-fluorobenzyl)-2-fluoro-4-methyl-5-((2,2,2-trifluoroethyl) thio) aniline (Compound 249)

S1. Preparation of 4-fluoro-2-methyl-5-nitrobenzenesulfonyl chloride

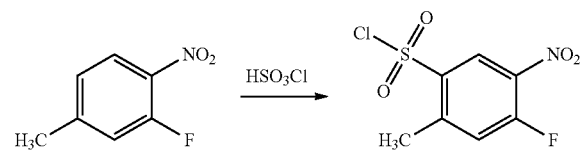

At room temperature, chlorosulfonic acid (34.95 g, 30 mmol) was added into a 250 mL round bottom flask, and 2-fluoro-4-methylnitrobenzene (15.5 g, 10 mmol) was slowly added into the flask in four batches. The reaction solution was exothermic obviously. Thereafter, the reaction flask was heated at 60° C., and 2 hours later, the reaction was detected to be basically completed. The reaction solution was added into 500 mL of ice-water mixture, and 400 mL of dichloromethane was added for extraction and liquid separation. 300 mL of water was added to the organic phase. After extraction and separation, the organic phase was evaporated in a rotary evaporator and extracted by silica gel column chromatography, to obtain 16.5 g of a light yellow solid (yield of 64.45%).

S2. Preparation of 1,2-bis (4-fluoro-2-methyl-5-nitrophenyl) disulfide

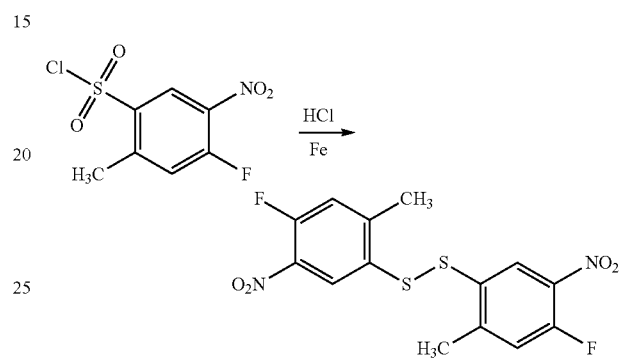

Under the protection of nitrogen, 4-fluoro-2-methyl-5-nitrobenzenesulfonyl chloride (12.7 g, 5 mmol) was dissolved in 200 mL of acetic acid. 40 mL concentrated hydrochloric acid was added, and the reaction solution was heated to reflux. An iron powder (11.2 g, 20 mmol) was slowly added into the reaction solution in 4 batches within 1 hour. 1.5 hours later, 20 mL of concentrated salt acid was added and stirred for an hour. Thereafter, most acetic acid in the reaction solution was evaporated, and 300 mL of ethyl acetate and 300 mL of water were added to the reaction solution for extraction and liquid separation. 150 mL of ethyl acetate was added to the water layer for extraction and liquid separation again. The organic layers were combined and washed with 50 mL of saturated sodium chloride solution, dried over 10 g of anhydrous sodium sulfate for 10 min, evaporated in a rotary evaporator, and purified by silica gel column chromatography, to obtain 7.4 g of a light brown solid (yield of 79.56%).

S3. Preparation of 5,5'-disulfide (2-fluoro-4-methylaniline)

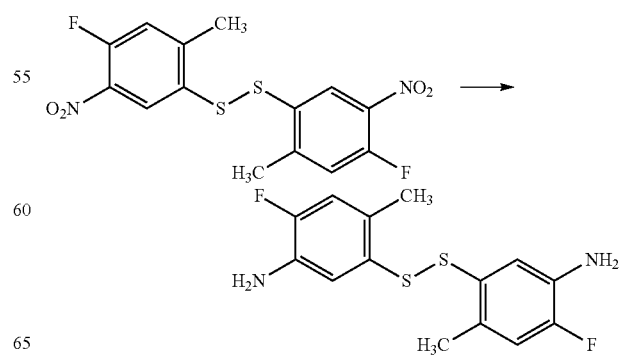

Method 1:

1,2-bis (4-fluoro-2-methyl-5-nitrophenyl) disulfide (3.72 g, 1 mmol) was added to 30 mL of 20% hydrochloric acid. The reaction solution was heated at 60° C., and zinc powder (1.30 g, 2 mmol) was slowly added in batches and stirred for 1 hour under heating. Most of acetic acid was removed by vacuum rotary evaporation, and 100 mL of saturated sodium carbonate solution and 100 mL ethyl acetate were added to the residue for extraction and separation. The organic layer was dried over 5 g of anhydrous sodium sulfate, evaporated in a rotary evaporator, and purified by silica gel column chromatography, to yield 2.45 g of an off-white solid (yield of 78.52%).

Method 2:

1,2-bis (4-fluoro-2-methyl-5-nitrophenyl) disulfide (1.86 g, 0.5 mmol) was dissolved in 30 mL of anhydrous ethanol. The air in the reaction flask was replaced with nitrogen, and 0.3 g of palladium carbon (containing 50% water) with 10% palladium was added. The gas in the reaction flask was replaced with hydrogen, and the reaction solution was stirred in 20 atmospheric pressure in the hydrogen atmosphere at 65° C. for 10 hours. After the reaction, the palladium carbon was removed by vacuum filtration, and the reaction solution was evaporated in a rotary evaporator to obtain 1.50 g of a light brown solid (yield of 96.2%).

S4. Preparation of 2-fluoro-4-methyl-5-((2,2,2-trifluoroethyl) thio) aniline

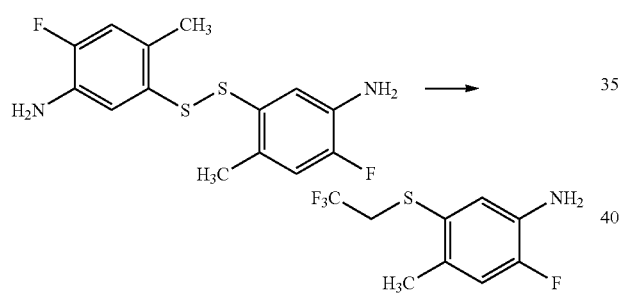

Method 1:

5,5'-disulfide (2-fluoro-4-methylaniline) (1.56 g, 5 mmol) was dissolved in 30 mL of N, N-dimethylformamide (DMF). 50 mL of sodium dihydrogen phosphate (5.0 g, 41.7 mmol) aqueous solution was added to the reaction solution. The air in the reaction flash was purged by nitrogen, and sodium hydrosulfite (2.5 g, 14.4 mmol) was added. The reaction flask was heated at 60° C. for 2 hours, and then 2,2-trifluoroethyltrifluoromethane sulfonate (3.48 g, 14.4 mmol) was added and stirred for 1 hour. Thereafter, the reaction solution was added into 300 mL of water, and 200 mL of ethyl acetate was added for extraction and liquid separation. The organic layer was washed with water four times, 300 mL of water each time. After washing, the organic layer was evaporated in a rotary evaporator, and purified by silica gel column chromatography, to yield to obtain 1.68 g of light brown liquid (yield 70.29%).

¹H-NMR (400 MHz, d6-DMSO): δ=7.01 (m, 2H, Ar—H), 5.12 (s, 2H, N—H), 3.76 (dd, J=21.2, 10.4 Hz, 2H, CH₂), 2.30 (s, 3H, CH₃).

Method 2:

5,5'-disulfide (2-fluoro-4-methylaniline) (1.56 g, 5 mmol) was dissolved in 30 mL of N, N-dimethylformamide (DMF).

Sodium carbonate (0.53 g, 5 mmol) and sodium hydroxymethylsulfinate (0.67 g, 5 mmol) were added, and then 2,2,2-trifluoroioethane (3.15 g, 15 mmol) was added and stirred for 1 hour. Thereafter, the reaction solution was added into 300 mL of water, and 200 mL of ethyl acetate was added for extraction and liquid separation. The organic layer was washed with water four times, 300 mL of water each time. After washing, the organic layer was evaporated in a rotary evaporator, and purified by silica gel column chromatography, to yield to obtain 1.77 g of light brown liquid (yield of 74.06%).

¹H-NMR (400 MHz, d6-DMSO): δ=7.01 (m, 2H, Ar—H), 5.12 (s, 2H, N—H), 3.76 (dd, J=21.2, 10.4 Hz, 2H, CH₂), 2.30 (s, 3H, CH₃).

S5. Preparation of N-(4-chloro-3-fluorobenzyl)-2-fluoro-4-methyl-5-((2,2,2-trifluoroethyl) thio) aniline (Compound 249)

2-fluoro-4-methyl-5-((2,2,2-trifluoroethyl) thio) aniline (239 mg, 1 mmol) was added to DMF (5 mL), and then potassium carbonate (138 mg, 1 mmol) and 4-bromomethyl-1-chloro-2-fluorobenzene (223 mg, 1 mmol) were added sequentially. The reaction solution was stirred at room temperature for 5 hours, added into 100 mL of water, and extracted twice with 100 mL of ethyl acetate. The organic phase was washed with water, dried over anhydrous sodium sulfate, vacuum concentrated, and purified with column chromatography to yield 252 mg of a colorless viscous liquid. The yield was 66.0%.

¹H-NMR (500 MHz, CDCl₃): δ=7.21-7.34 (m, 2H), 7.00-7.04 (m, 1H), 6.79-6.88 (m, 2H), 4.44 (d, J=8.0 Hz, 2H), 3.17 (q, J=7.5 Hz, 2H), 2.36 (d, J=21.5 Hz, 3H).

MS (m/z, ESI): 382.04 (m+H).

Example 2

Preparation of 2-fluoro-N-(3-fluorobenzyl)-4-methyl-5-((2,2,2-trifluoroethyl) thio) aniline (compound 229)

S1. Preparation of 4-fluoro-2-methyl-5-nitrophenylthiophenol 4-fluoro-2-methyl-5-nitrobenzenesulfonyl chloride (0.15 mol, 38.0 g) was placed in a 250 mL single mouthed flask, and 80 mL of hydroiodate was added. The reaction solution turned black, and was stirred at room temperature for 1 hour. Thereafter, 80 mL of saturated sodium sulfite solution was slowly added, and a yellow powdery solid appeared in the reaction solution. The yellow powdery solid was vacuum filtered and washed with water, to yield 28.0 g of a light yellow powder with a yield of 100%.

S2. Preparation of 4-fluoro-2-methyl-5-aminothiophenol 4-fluoro-2-methyl-5-nitrobenzene thiophenol (0.15 mol, 28.0 g) was dissolved in anhydrous ethanol (280 mL), and 10% palladium carbon (1.0 g, 50% water content) was added. The gas in the reaction flask was replaced by hydrogen three times, and the reaction solution was stirred overnight at room temperature under normal pressure in the hydrogen atmosphere. The reaction solution was filtered under reduced pressure to remove palladium carbon, and concentrated to dryness under reduced pressure to remove ethanol. 23.2 g of a gray white solid was obtained with a yield of 98.7%. 1H-NMR (400 MHz, d6-DMSO): δ=6.93 (m, 2H, Ar—H), 5.12 (s, 2H, N—H), 3.35 (br, 0.5H, S—H), 2.15 (s, 3H, CH3).

S3. Preparation of 2-fluoro-4-methyl-5-(2,2,2-trifluoroethyl) thio) aniline 4-fluoro-2-methyl-5-aminothiophenol (25 mmol, 3.9 g) was dissolved in anhydrous DMF (50 mL), and then sodium carbonate (50 mmol, 5.3 g, 2 eq) and sodium hydroxymethyl sulfite (25 mmol, 3.4 g, 1 eq) were added successively. Thereafter, trifluoroethane (27.5 mmol, 5.8 G, 1.1 eq) was added under ice bath. The reaction solution was stirred at room temperature for 2 hours until the reaction was complete. The reaction solution was poured into water, and extracted and separated with ethyl acetate. The organic layer was washed with water for three times, and then washed with saturated salt water once. After separation, the organic layer was dried over anhydrous sodium sulfate, and dried under reduced pressure to yield a light brown oily liquid. The light brown oily liquid was purified by column chromatography with a mobile phase of petroleum ether:ethyl acetate=10:1, to yield 4.2 g of a yellow oily product with a yield of 71.2%.

1H-NMR (400 MHz, d6-DMSO): δ=7.01 (m, 2H, Ar—H), 5.12 (s, 2H, N—H), 3.76 (dd, J=21.2, 10.4 Hz, 2H, CH2), 2.30 (s, 3H, CH3).

S4. Preparation of 2-fluoro-N-(3-fluorobenzyl)-4-methyl-5-((2,2,2-trifluoroethyl) thio) aniline (Compound 229)

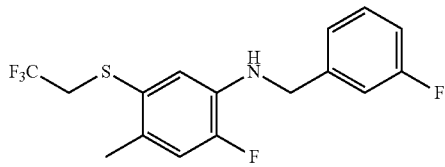

The operations are the same as that in S5 of Example 1.
$^1$H-NMR (500 MHz, CDCl$_3$): δ=7.28-7.33 (m, 1H), 7.05-7.14 (m, 2H), 6.94-6.99 (m, 1H), 6.85 (d, J=15.0 Hz, 1H), 6.75 (d, J=10.5 Hz, 1H), 4.36 (d, J=7.0 Hz, 2H), 3.17 (q, J=12.0 Hz, 2H), 2.35 (d, J=6.0 Hz, 3H).
MS (m/z, ESI): 388.07 (m+H).

Example 3

Preparation of 2-fluoro-N-(3-methoxybenzyl)-4-methyl-5-(2,2,2-trifluoroethyl) thio) aniline (Compound 239)

S1: Preparation of N-(2-fluoro-4-methylphenyl) acetamide

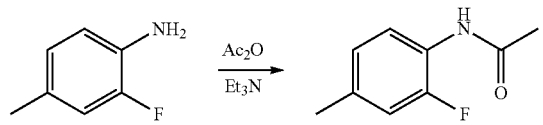

2-fluoro-4-methylaniline (125 g, 1 mol) was dissolved in dichloromethane (1 L), and triethylamine (111 g, 1.1 mol) was added. The mixture solution was cooled in an ice salt bath until the internal temperature thereof was 0° C. Acetic anhydride (102 g, 1 mol) was added slowly. Thereafter, the reaction solution was stirred for reaction at room temperature for 3 hours. 2 L of water was added to the reaction solution for extraction and separation. The organic phase was dried over anhydrous sodium sulfate, and evaporated in a rotary evaporator, to yield 162 g of a white solid, with a yield of 97.0%.

S2: Preparation of 5-acetamino-4-fluoro-2-methylbenzenesulfonyl chloride

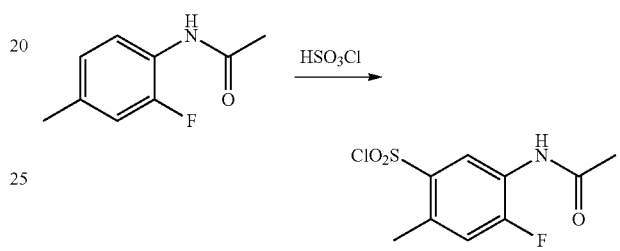

N-(2-fluoro-4-methylphenyl) acetamide (145 g, 868 mmol) was added to a 1 L round bottom flask, and a tail gas absorption device was disposed on the round bottom flask. Chlorosulfonic acid (302 g, 2.60 mol) was slowly added and electrically stirred. Thereafter, the mixed solution was heated until the internal temperature thereof was 60° C. 3 hours later, the temperature was reduced to room temperature. The reaction liquid was stirred and slowly added to 2 kg of ice, and extracted twice with 500 mL of ethyl acetate. The organic phases were combined, dried over anhydrous sodium sulfate, and evaporated in a rotary evaporator, to yield 175.2 g of an off-white solid, with a yield of 76.2%.

S3: Preparation of N-(2-fluoro-5-mercapto-4-methylphenyl) acetamide

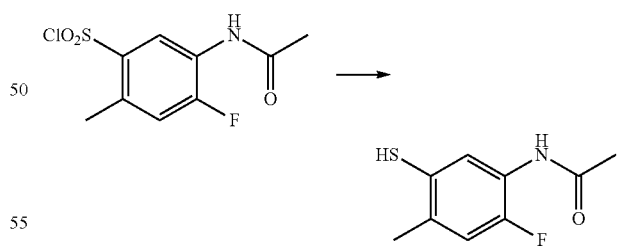

5-acetamino-4-fluoro-2-methylbenzenesulfonyl chloride (174.6 g, 660 mmol) was added to acetic acid (700 mL), and red phosphorus (50 g, 1.61 mol) and iodine (2 g) were added sequentially. The reaction liquid was heated to a reflux state and stirred for 3 hours. The reaction liquid was concentrated under reduced pressure to remove acetic acid. 1.5 L of water and 1 L of ethyl acetate were added for extraction and liquid separation. 500 mL of ethyl acetate was added to the aqueous phase to separate the liquid. The organic phases were combined, washed with sodium carbonate solution, separated and evaporated in a rotary evaporator to yield 103.4 g of a light brown solid with a yield of 78.4%.

S4: Preparation of 5-amino-4-fluoro-2-methylthiophenol

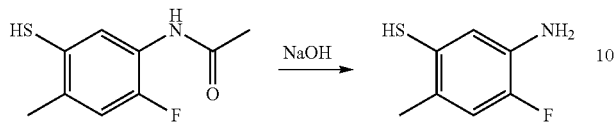

N-(2-fluoro-5-mercapto-4-methylphenyl) acetamide (101 g, 507 mmol) was added to 10% sodium hydroxide aqueous solution (1 L), heated and refluxed for 5 hours. The pH of the reaction solution was adjusted to 7 with dilute hydrochloric acid, and then the reaction solution was extracted with ethyl acetate. The organic phase was dried with anhydrous sodium sulfate and concentrated under reduced pressure. 62.7 g of an off-white solid was obtained with a yield of 78.8%.

S5: Preparation of 2-fluoro-4-methyl-5-((2,2,2-trifluoroethyl) thio) aniline

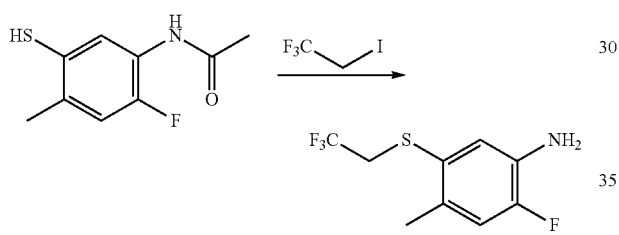

5-amino-4-fluoro-2-methylthiophene (15.72 g, 0.1 mol) was dissolved in DMF (100 mL), and then potassium hydroxide (5.6 g, 0.1 mol), sodium formaldehyde bisulfite (15.4 g, 0.1 mol) and trifluoro iodoethane (20.9 g, 0.1 mol) were successively added. The reaction solution was stirred at room temperature for 5 hours, and then added into 500 mL of water. 500 mL of ethyl acetate extract was added for extraction and liquid separation. 200 mL of ethyl acetate was added to the aqueous phase to extract and separate the liquid. The organic layers were combined, washed with 500 mL of water twice. The organic phase was separated, dried over anhydrous sodium sulfate, concentrated under reduced pressure, and then purified by column chromatography. 16.6 g of a light brown liquid was obtained with a yield of 69.45%.

S6: Preparation of 2-fluoro-N-(3-methoxybenzyl)-4-methyl-5-((2,2,2-trifluoroethyl) thio) aniline (Compound 239)

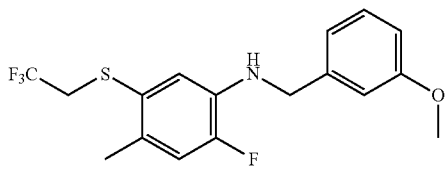 [SMILES: COc1cccc(CNc2cc(SCC(F)(F)F)c(C)cc2F)c1]

The operations are the same as that in S5 of Example 1.
$^1$H-NMR (500 MHz, CDCl$_3$): δ=7.24-7.28 (m, 1H), 6.76-6.98 (m, 5H), 4.30 (d, J=16.5 Hz, 2H), 3.75 (s, 3H), 3.15 (q, J=12.0 Hz, 2H), 2.35 (s, 3H).
MS (m/z, ESI): 360.09 (m+H).

Example 4

Preparation of 2-fluoro-4-methyl-n-(3-nitrobenzyl)-5-((2,2,2-trifluoroethyl) thio) aniline (Compound 241)

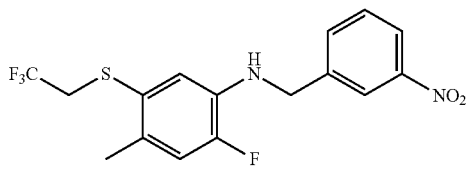 [SMILES: Cc1cc(F)c(NCc2cccc([N+](=O)[O-])c2)cc1SCC(F)(F)F]

The operations are the same as that in S5 of Example 1.
$^1$H-NMR (500 MHz, CDCl$_3$): δ=8.10 (d, J=10.0 Hz, 1H), 7.58-7.60 (m, 2H), 7.44-7.47 (m, 1H), 6.87 (d, J=14.5 Hz, 1H), 6.68 (d, J=11.0 Hz, 1H), 4.75 (d, J=8.0 Hz, 2H), 3.15 (q, J=12.0 Hz, 2H), 2.35 (s, 3H).
MS (m/z, ESI): 375.06 (m+H).

Example 5

Preparation of N-(3,4-dichlorobenzyl)-2-fluoro-4-methyl-5-(2,2,2-trifluoroethyl) thio) aniline (Compound 247)

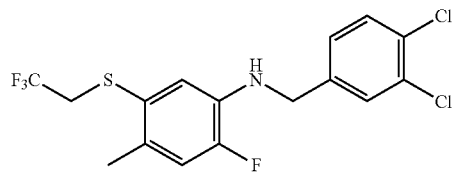 [SMILES: Cc1cc(F)c(NCc2ccc(Cl)c(Cl)c2)cc1SCC(F)(F)F]

The operations are the same as that in S5 of Example 1.
$^1$H-NMR (500 MHz, CDCl$_3$): δ=7.34-7.45 (m, 2H), 7.19 (dd, J$_1$=3.0 Hz, J$_2$=10.5 Hz, 1H), 6.73 (d, J=10.5 Hz, 1H), 6.55 (d, J=10.5 Hz, 1H), 4.31 (d, J=6.5 Hz, 2H), 3.17 (q, J=12.5 Hz, 2H), 2.36 (d, J=14.0 Hz, 3H).
MS (m/z, ESI): 398.01 (m+H).

Example 6

Preparation of 2-(((2-fluoro-4-methyl-5-((2,2,2-trifluoroethyl) thio) phenyl) amino) methyl) benzoate (Compound 53)

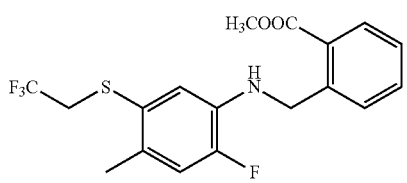

The operations are the same as that in S5 of Example 1.
$^1$H-NMR (500 MHz, CDCl$_3$): δ=7.98 (d, J=9.5 Hz, 1H), 7.46-7.48 (m, 2H), 7.31-7.34 (m, 1H), 6.80-6.84 (m, 2H), 4.68 (s, 2H), 3.92 (s, 3H), 3.18 (q, J=12.0 Hz, 3H), 2.32 (s, 3H).
MS (m/z, ESI): 388.06 (m+H).

Example 7

Preparation of N-(3-bromobenzyl)-2-fluoro-4-methyl-5-((2,2,2-trifluoroethyl) thio) aniline (Compound 233)

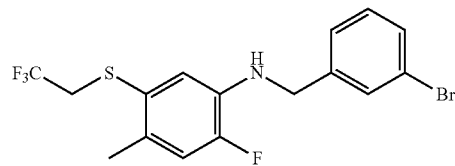 [SMILES: Cc1cc(F)c(NCc2cccc(Br)c2)cc1SCC(F)(F)F]

The operations are the same as that in S5 of Example 1.
$^1$H-NMR (500 MHz, CDCl$_3$): δ=7.51 (s, 1H), 7.38-7.42 (m, 1H), 7.23-7.40 (m, 2H), 6.85-6.88 (m, 1H), 6.76 (d, J=11.0 Hz, 1H), 4.34 (s, 2H), 3.17 (q, J=12.0 Hz, 2H), 2.36 (d, J=10.0 Hz, 3H).
MS (m/z, ESI): 408.00 (m+H).

Example 8

Preparation of 2-fluoro-N-(4-iodobenzyl)-4-methyl-5-((2,2,2-trifluoroethyl) thio) aniline (Compound 707)

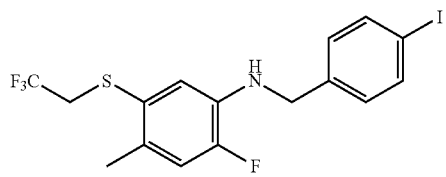 [SMILES: Cc1cc(F)c(NCc2ccc(I)cc2)cc1SCC(F)(F)F]

The operations are the same as that in S5 of Example 1.
$^1$H-NMR (500 MHz, CDCl$_3$): δ=7.72 (s, 1H), 7.62 (d, J=9.5 Hz, 1H), 7.29-7.32 (m, 1H), 7.08-7.12 (m, 1H), 6.87 (d, J=15.5 Hz, 1H), 6.76 (d, J=11.0 Hz, 1H), 4.32 (s, 2H), 3.17 (q, J=12.0 Hz, 2H), 2.33 (d, J=21.5 Hz, 3H).
MS (m/z, ESI): 455.87 (m+H).

Example 9

Preparation of N-(3-bromo-5-fluorobenzyl)-2-fluoro-4-methyl-5-((2,2,2-trifluoroethyl) thio) aniline (Compound 251)

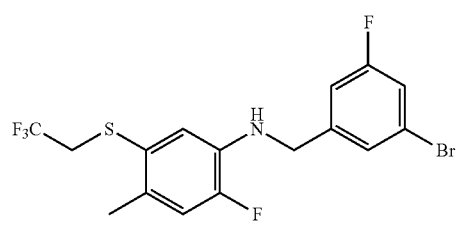 [SMILES: Cc1cc(F)c(NCc2cc(F)cc(Br)c2)cc1SCC(F)(F)F]

The operations are the same as that in S5 of Example 1.
$^1$H-NMR (500 MHz, CDCl$_3$): δ=7.19-7.27 (m, 3H) 6.78-6.87 (m, 2H), 4.37 (d, J=7.0 Hz, 2H), 3.21 (q, J=12.0 Hz, 2H), 2.34-2.36 (m, 3H).
MS (m/z, ESI): 325.98 (m+H).

Example 10

Preparation of 2-fluoro-n-(4-fluorobenzyl)-4-methyl-5-((2,2,2-trifluoroethyl) thio) aniline (Compound 709)

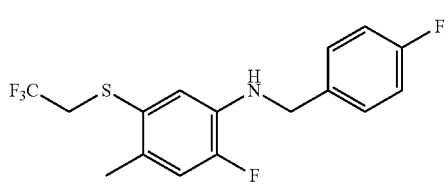 [SMILES: Cc1cc(F)c(NCc2ccc(F)cc2)cc1SCC(F)(F)F]

The operations are the same as that in S5 of Example 1.
$^1$H-NMR (500 MHz, CDCl$_3$): δ=7.30-7.34 (m, 2H), 6.96-7.06 (m, 2H), 6.82 (d, J=11.5 Hz, 1H), 6.76 (d, J=11.0 Hz, 1H), 4.31 (d, J=7.0 Hz, 2H), 3.22 (q, J=12.5 Hz, 2H), 2.34-2.36 (m, 3H).
MS (m/z, ESI): 348.07 (m+H).

Example 11

Preparation of N-(4-chlorobenzyl)-2-fluoro-4-methyl-5-((2,2,2-trifluoroethyl) thio) aniline (Compound 711)

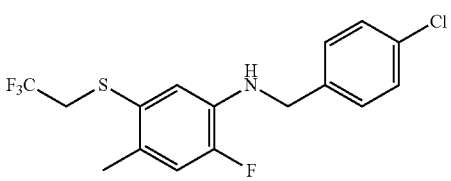 [SMILES: Cc1cc(F)c(NCc2ccc(Cl)cc2)cc1SCC(F)(F)F]

The operations are the same as that in S5 of Example 1.
$^1$H-NMR (500 MHz, CDCl3): δ=7.35 (s, 1H), 7.22-7.28 (m, 3H), 6.87 (d, J=15.0 Hz, 1H), 6.76 (d, J=11.0 Hz, 1H), 4.31 (d, J=7.0 Hz, 2H), 3.21 (q, J=12.0 Hz, 2H), 2.34-2.37 (m, 3H).
MS (m/z, ESI): 364.05 (m+H).

Example 12

Preparation of N-benzyl-2-fluoro-4-methyl-5-((2,2,2-trifluoroethyl) thio) aniline (Compound 1105)

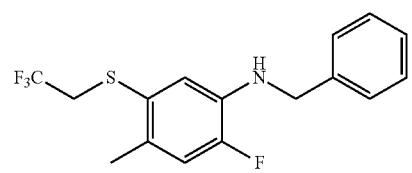 [SMILES: Cc1cc(F)c(NCc2ccccc2)cc1SCC(F)(F)F]

The operations are the same as that in S5 of Example 1.
$^1$H-NMR (500 MHz, CDCl3): δ=7.18-7.28 (m, 6H), 6.73-6.82 (m, 2H), 4.26 (s, 2H), 3.06-3.16 (m, 2H), 2.27 (s, 3H).
MS (m/z, ESI): 330.09 (m+H).

Example 13

Preparation of 4-((2-fluoro-4-methyl-5-((2,2,2-trifluoroethyl) thio) phenyl) amino) methyl) benzylnitrile (Compound 721)

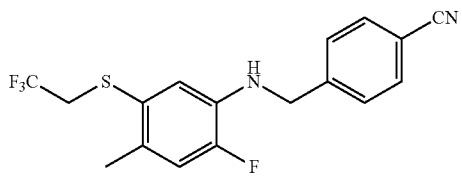 [SMILES: Cc1cc(F)c(NCc2ccc(C#N)cc2)cc1SCC(F)(F)F]

The operations are the same as that in S5 of Example 1.
$^1$H-NMR (500 MHz, CDCl3): δ=7.64 (d, J=10.0 Hz, 2H), 7.46 (d, J=10.5 Hz, 2H), 6.88 (d, J=18.5 Hz, 1H), 6.66 (d, J=11.0 Hz, 1H), 4.44 (s, 2H), 3.14 (q, J=7.0 Hz, 2H), 2.36 (s, 3H).
MS (m/z, ESI): 355.08 (m+H).

Example 14

Preparation of methyl 4-((2-fluoro-4-methyl-5-((2,2,2-trifluoroethyl) thio) phenyl) amino) methyl benzoate (Compound 739)

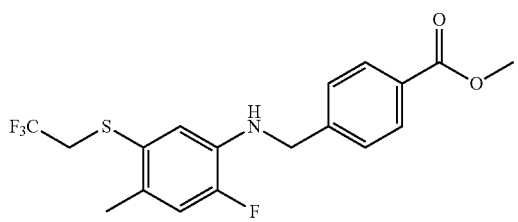 [SMILES: COC(=O)c1ccc(CNc2cc(SCC(F)(F)F)c(C)cc2F)cc1]

The operations are the same as that in S5 of Example 1.
$^1$H-NMR (500 MHz, CDCl3): δ=7.94 (d, J=10.5 Hz, 2H), 7.34 (d, J=10.0 Hz, 2H), 6.77 (d, J=15.5 Hz, 1H), 6.68 (d, J=10.5 Hz, 1H), 4.34 (s, 2H), 3.83 (s, 3H), 3.07 (q, J=12.0 Hz, 2H), 2.27 (s, 3H).
MS (m/z, ESI): 388.06 (m+H).

Example 15

Preparation of 2-fluoro-N-(4-methoxybenzyl)-4-methyl-5-((2,2,2-trifluoroethyl) thio) aniline (Compound 1131)

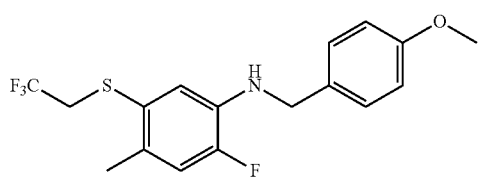 [SMILES: COc1ccc(CNc2cc(SCC(F)(F)F)c(C)cc2F)cc1]

The operations are the same as that in S5 of Example 1.
$^1$H-NMR (500 MHz, CDCl3): δ=7.20-7.26 (m, 2H), 7.67-7.84 (m, 4H), 5.07 (s, 1H), 4.20 (s, 2H), 3.69 (s, 3H), 3.13 (q, J=12.0 Hz, 2H), 2.28 (s, 3H).
MS (m/z, ESI): 360.09 (m+H).

Example 16

Preparation of 2-((2-fluoro-4-methyl-5-((2,2,2-trifluoroethyl) thio) phenyl) amino) methyl) benzylnitrile (Compound 33)

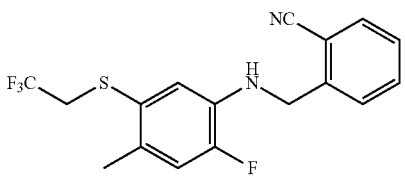 [SMILES: Cc1cc(F)c(NCc2ccccc2C#N)cc1SCC(F)(F)F]

The operations are the same as that in S5 of Example 1.
$^1$H-NMR (500 MHz, CDCl3): δ=7.68 (d, J=9.5 Hz, 1H), 7.50-7.55 (m, 2H), 7.35-7.37 (m, 1H), 6.85 (d, J=8.5 Hz, 1H), 6.74 (d, J=10.5 Hz, 1H), 3.18 (q, J=12.0 Hz, 2H), 2.35 (s, 3H).
MS (m/z, ESI): 355.08 (m+H).

Example 17

Preparation of 2-fluoro-4-methyl-N-(4-nitrobenzyl)-5-((2,2,2-trifluoroethyl) thio) aniline (Compound 755)

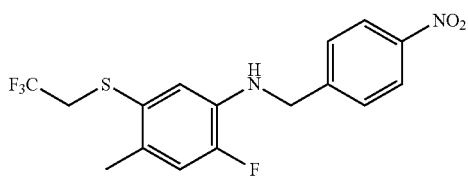 [SMILES: Cc1cc(F)c(NCc2ccc([N+](=O)[O-])cc2)cc1SCC(F)(F)F]

The operations are the same as that in S5 of Example 1.
$^1$H-NMR (500 MHz, CDCl3): δ=7.68 (d, J=9.5 Hz, 1H), 7.50-7.55 (m, 2H), 7.35-7.37 (m, 1H), 6.85 (d, J=8.5 Hz, 1H), 6.74 (d, J=10.5 Hz, 1H), 4.49 (s, 2H), 3.18 (q, J=12.0 Hz, 2H), 2.35 (s, 3H).
MS (m/z, ESI): 375.06 (m+H).

Example 18

Preparation of 2-fluoro-N-(2-iodobenzyl)-4-methyl-5-((2,2,2-trifluoroethyl) thio) aniline (Compound 31)

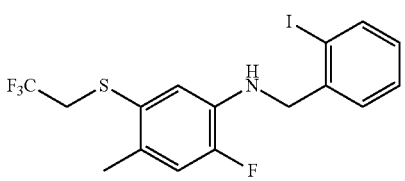 [SMILES: Cc1cc(F)c(NCc2ccccc2I)cc1SCC(F)(F)F]

The operations are the same as that in S5 of Example 1.

$^1$H-NMR (500 MHz, CDCl3): δ=7.86 (d, J=10.0 Hz, 1H), 7.30-7.33 (m, 2H), 6.95-7.00 (m, 1H), 6.85 (d, J=8.5 Hz, 1H), 6.73 (d, J=11.0 Hz, 1H), 4.34 (s, 2H), 3.20 (q, J=12.0 Hz, 2H), 2.35 (s, 3H).

MS (m/z, ESI): 455.87 (m+H).

Example 19

Preparation of 2-fluoro-4-methyl-5-((2,2,2-trifluoroethyl) thio)-N-(2-(trifluoromethoxy) benzyl) aniline (Compound 1107)

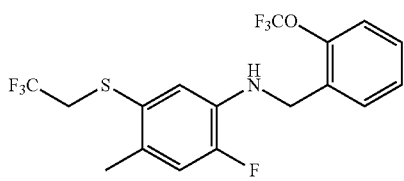 [SMILES: Cc1cc(F)c(NCc2ccccc2OC(F)(F)F)cc1SCC(F)(F)F]

The operations are the same as that in S5 of Example 1.

$^1$H-NMR (500 MHz, CDCl3): δ=7.30-7.53 (m, 4H), 6.85 (d, J=16.5 Hz, 1H), 6.73 (d, J=10.5 Hz, 1H), 4.44 (s, 2H), 3.17 (q, J=12.0 Hz, 2H), 2.36 (s, 3H).

MS (m/z, ESI): 413.95 (m+H).

Example 20

Preparation of 2-fluoro-n-(4-fluorobenzyl)-4-methyl-5-((2,2,2-trifluoroethyl) sulfinyl) aniline (Compound 710)

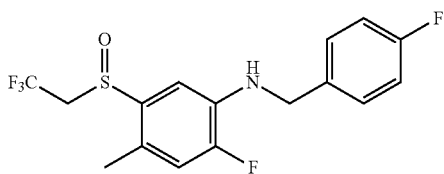 [SMILES: Cc1cc(F)c(NCc2ccc(F)cc2)cc1S(=O)CC(F)(F)F]

2-fluoro-N-(4-fluorobenzyl)-4-methyl-5-((2,2,2-trifluoroethyl) thio) aniline (347 mg, 1 mmol) was dissolved in chloroform (5 mL). m-chloroperoxybenzoic acid (172 mg, 1 mmol) was added under an ice bath. The reaction solution was stirred for 1 hour, and 50 mL of ethyl acetate and 50 mL of water were added for extraction and liquid separation. 50 mL of ethyl acetate was added to the aqueous phase. The organic phases were combined, washed with 50 mL of saturated salt water, evaporated in a rotary evaporator and purified by silica gel column chromatography, to obtain 288 mg of a white solid, with a yield of 79.3%.

$^1$H-NMR (500 MHz, CDCl3): δ=7.30-7.34 (m, 2H), 6.96-7.06 (m, 2H), 6.85 (d, J=11.5 Hz, 1H), 6.56 (d, J=11.0 Hz, 1H), 4.31 (d, J=7.0 Hz, 2H), 3.22 (q, J=12.5 Hz, 2H), 2.26 (s, 3H).

MS (m/z, ESI): 364.07 (m+H).

Example 21

Preparation of 2-((((2-Fluoro-4-methyl-5-((2,2,2-trifluoroethyl) sulfonyl) phenyl) amino) methyl) benzoate (Compound 54)

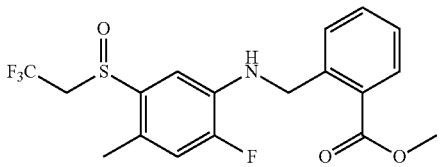 [SMILES: COC(=O)c1ccccc1CNc1cc(S(=O)CC(F)(F)F)c(C)cc1F]

The operations are the same as that in S5 of Example 1 and Example 20.

1H-NMR (500 MHz, CDCl3): δ=7.94-8.04 (m, 1H), 7.45-7.48 (m, 2H), 7.25-7.28 (m, 2H), 6.82 (d, J=14.5 Hz, 1H), 4.73 (s, 2H), 3.94 (s, 3H), 3.29 (q, J=18.0 Hz, 2H), 2.23 (s, 3H).

MS (m/z, ESI): 404.1 (m+H), 424.1 (m+Na).

Example 22

Preparation of 5-Fluoro-2-((((2-Fluoro-4-methyl-5-(2,2,2-trifluoroethyl) thio) phenyl) amino) methyl) benzoate (Compound 303)

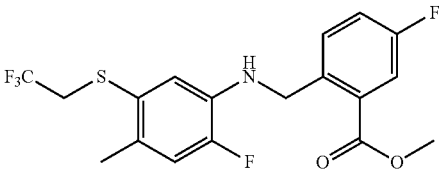 [SMILES: COC(=O)c1cc(F)ccc1CNc1cc(SCC(F)(F)F)c(C)cc1F]

The operations are the same as that in S5 of Example 1.

1H-NMR (500 MHz, CDCl3): δ=7.68 (dd, $J_1$=3.5 Hz, $J_2$=11.5 Hz, 1H), 7.45 (dd, $J_1$=7.0 Hz, $J_2$=10.5 Hz, 1H), 7.16 (t, J=10 Hz, 1H), 6.81 (dd, $J_1$=10.5 Hz, $J_2$=17.5 Hz, 2H), 4.65 (s, 2H), 3.92 (s, 3H), 3.19 (q, J=7.5 Hz, 2H), 2.33 (s, 3H).

MS (m/z, ESI): 406.5 (m+H).

Example 23

Preparation of 2-((((4-chloro-2-fluoro-5-((2,2,2-trifluoroethyl) thio) phenyl) amino) methyl) benzoate (Compound 1202)

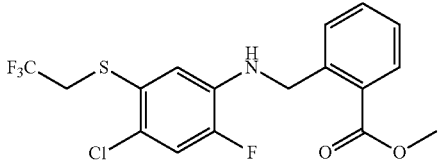 [SMILES: COC(=O)c1ccccc1CNc1cc(SCC(F)(F)F)c(Cl)cc1F]

The operations are the same as that in S5 of Example 1.

1H-NMR (500 MHz, CDCl3): δ=8.00 (dd, $J_1$=1.5 Hz, $J_2$=9.5 Hz, 1H), 7.43-7.50 (m, 2H), 7.33-7.38 (m, 1H), 7.05

(d, J=14 Hz, 1H), 6.91 (d, J=6.0 Hz, 1H), 4.69 (s, 2H), 3.92 (s, 3H), 3.32 (q, J=14.0 Hz, 2H).
MS (m/z, ESI): 408.5 (m+H), 430.5 (m+Na).

Example 24

Preparation of 2-Fluoro-N-(4-Fluoro-Benzyl)-4-methyl-5-((2,2,2-trifluoroethyl) sulfide) aniline (hydrochloride of Compound 709)

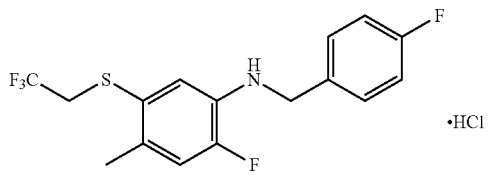 [SMILES: Cc1cc(F)c(NCc2ccc(F)cc2)cc1SCC(F)(F)F ; Cl]

2-fluoro-N-(4-fluoro-benzyl)-4-methyl-5-((2,2,2-trifluoroethyl) sulfide) aniline (347 mg, 1 mmol) was dissolved in methanol (5 mL), and 30% hydrogen chloride methanol solution (5 mL) was added. The mixed solution was stirred at room temperature for 1 hour, and distilled under reduced pressure to remove the solvent and hydrogen chloride. 384 mg of a white solid was obtained with a yield of 100%.
$^1$H-NMR (500 MHz, DMSO): δ=7.11-7.28 (m, 6H), 6.75-6.85 (m, 2H), 4.58 (d, J=7.0 Hz, 2H), 3.22 (q, J=12.5 Hz, 2H), 2.34-2.36 (m, 3H).
MS (m/z, ESI): 348.07 (m+H).

Example of Preparation 1

Emulsifiable Concentrate Comprising 8% of Compound 709
8 parts of the compound 709 were dissolved in a mixture of 10 parts of methylnaphthalene, 2 parts of methylpyrrolidone and 20 parts of methyl oleate 1169. The mixture was stirred, and 8 parts of calcium dodecyl benzene sulfonate and 4 parts of tristyrene phenol polyoxyethylene polyoxypropylene ether were added. The balance was aromatic solvent oil until the total weight was 100 parts. The mixed solution was stirred to yield an emulsifiable concentrate comprising 8% of the compound 709.

Example of Preparation 2

Suspension Agent Comprising 20% of Compound 710
20 parts of the compound 71, 1 part of magnesium aluminum silicate and 0.3 parts of benzoic acid were mixed for use. 3 parts of ammonium tristyrylphenol polyoxyethylene ether sulfate, 3 parts of a block polyether, 5 parts of ethylene glycol and water were sheared and mixed in a high-speed shear machine. Then, the sheared additives were added to the solid mixture, stirred and sheared, and then ground in a grinder for 3 hours. Thereafter, the glass beads were filtered out to obtain a suspending agent comprising 20% of the compound 710.

Example of Preparation 3

Wettable Powders Comprising 20% of Compound 53
20 parts of the compound 53 was added to a mixture of 2 parts of sodium lauryl sulfate, 4 parts of sodium lignosulfonate, 20 parts of silica hydrate and 54 parts of clay. The mixture was fully stirred to yield wettable powders comprising 20% of the compound 53.

Example of Preparation 4

Granules Comprising 5% of Compound 53
2 parts of sodium dodecylbenzene sulfonate, 10 parts of bentonite and 83 parts of clay were added to 5 parts of the compound 53. The mixture was stirred fully, and appropriate amount of water was added. The mixture was continuously stirred, granulated with a granulator, and air dried to yield granules comprising 5% of the compound 53.

Example of Preparation 5

Dry Flowable Comprising 30% of Compound 53
30 parts of the compound 53, 20 parts of sodium lignosulfonate, 2 parts of a wetting agent, and 2 parts of white carbon black were mixed, and Kaolin was added until the total weight was 100 parts. The mixture was mixed with water, smashed and homogenized with a shearing machine, ground in a sand mill, and spray dried to yield a dry flowable comprising 30% of the compound 53.

Example of Use

Activity Test of *Tetranychus cinnabarinus*
The compound under test was dissolved in acetone and diluted to desired concentration with 0.1% Tween 80 solution with acetone content not exceeding 5%.
One true leaf was removed from the bean seedlings having two true leaves. *Tanyanychus cinarinus* was inoculated and the cardinal number thereof investigated. The whole plant was sprayed with a handheld sprayer, and each treatment was repeated for 3 times. After treatment, the bean seedlings were cultured in a constant temperature room. 72 hours later, the number of live mites was investigated and the mortality rate was calculated. The number of *Tetranychus cinnabarinus* was 100-200 per inoculation.

Mortality=(number of inoculated mites−number of live mites after treatment)×number of inoculated mites×100%.

In this test, the following compounds showed a lethal rate of over 90% against mites at 100 ppm (100 mg/L): Nos 1, 2, 3, 4, 5, 6, 25, 26, 27, 28, 29, 30, 33, 34, 39, 40, 41, 42, 43, 44, 53, 54, 55, 56, 57, 58, 67, 68, 71, 72, 95, 96, 97, 98, 99, 100, 108, 109, 110, 111, 139, 140, 141, 142, 153, 154, 155, 156, 167, 168, 169, 170, 229, 230, 231, 232, 247, 248, 249, 250, 253, 254, 255, 256, 257, 258, 275, 276, 277, 278, 283, 284, 285, 286, 289, 290, 291, 292, 293, 294, 303, 304, 305, 306, 307, 308, 317, 318, 321, 322, 331, 332, 355, 356, 357, 358, 366, 367, 368, 369, 423, 424, 425, 426, 507, 508, 509, 510, 523, 524, 535, 536, 537, 538, 577, 578, 619, 620, 635, 636, 647, 648, 649, 650, 805, 806, 807, 808, 817, 818, 819, 820, 929, 930, 931, 932, 957, 958, 1029, 1030, 1031, 1032, 1043, 1044, 1045, 1046, 1071, 1072, 1113, 1114, 1115, 1116, 1117, 1118, 1125, 1126, 1165, 1166, 1167, 1168, 1177, 1178, 1202, 1203, 1204, 1205, 1216, 1217, 1256, 1257, 1264, 1265, 1266, 1267, 1268, 1269, 1270, 1271, 1274, 1275, 1282, 1283, 1284, 1285, 1286, 1287, 1288, 1289, 1292, 1293, 1300, 1301, 1302, 1303, 1304, 1305, 1306, 1307, 1310, 1311, 1318, 1319, 1320, 1321, 1322, 1323, 1324, 1325, 1328, 1329.

In this test, the following compounds showed a lethal rate of more than 90% against mites at 25 ppm (25 mg/L): Nos 53, 54, 55, 56, 108, 109, 303, 304, 305, 306, 366, 367, 535, 536, 1165, 1166, 1167, 1168, 1177, 1178, 1202, 1203, 1264, 1265, 1282, 1283, 1300, 1301, 1318, 1319.

In this test, the following compounds showed a lethal rate of more than 90% against mites at 6.25 ppm (6.25 mg/L): Nos 53, 54, 303, 304, 1165, 1166, 1202, 1203.

According to the above method, the compound Nos 53, 54, 303, 304, 1165, 1166, 1202 and 1203 of the disclosure were selected to carry out the acaricidal parallel test with bifenazate and cyflumetofen. The test results are shown in Table 2 below:

TABLE 2

Test data

| Compound No: | Concentration (ppm) | Mortality % |
|---|---|---|
| 53 | 3.12 | 99 |
| 54 | 3.12 | 100 |
| 303 | 3.12 | 99 |
| 304 | 3.12 | 98 |
| 1165 | 3.12 | 99 |
| 1166 | 3.12 | 98 |
| 1202 | 3.12 | 97 |
| 1203 | 3.12 | 98 |
| Bifenazate | 3.12 | 85 |
| Cyflumetofen | 3.12 | 72 |

It will be obvious to those skilled in the art that changes and modifications may be made, and therefore, the aim in the appended claims is to cover all such changes and modifications.

What is claimed is:

1. An aryl sulfide of formula I, or an agriculturally acceptable salt thereof,

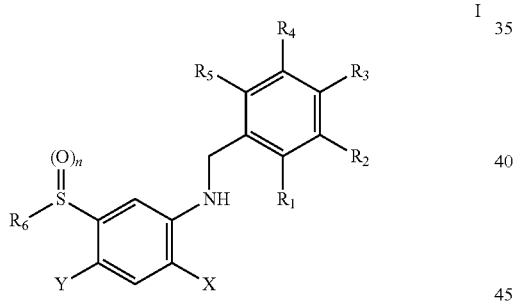

I wherein:
   n is 0 or 1;
   X is fluorine, chlorine, or methyl;
   Y is chlorine or methyl;
   $R_1$ is hydrogen, fluorine, chlorine, bromine, hydroxyl, nitro, hydroxymethyl, a cyano group, trifluoromethyl, $C_{1-3}$ alkyl, $C_{1-4}$ alkoxycarbonyl, acetyl, propionyl, $C_{1-3}$ alkoxy, ethylthio, 2-fluoroethanothioxy, 2-chloroethanothioxy, 2,2-difluoroethylthio, 2,2,2-trifluoroethylthio, propylthio, 2,2,2-trifluoroethylsulfinyl, vinyloxycarbonyl, 2,2,2-trifluoroethoxycarbonyl, or n-methylcarbonyl;
   $R_2$ is hydrogen, fluorine, or chlorine;
   $R_3$ is hydrogen, fluorine, chlorine, bromine, or a cyano group;
   $R_4$ and $R_5$ at each occurrence represent hydrogen; and
   $R_6$ is n-propyl or 2,2,2-trifluoroethyl.

2. The aryl sulfide of claim 1, wherein
   n is 0 or 1;
   X is fluorine;
   Y is chlorine or methyl;
   $R_1$ is methoxycarbonyl, ethoxycarbonyl, ethylthio, or 2,2,2-trifluoroethylthio;
   $R_2$, $R_4$, and $R_5$ at each occurrence represent hydrogen;
   $R_3$ is hydrogen, fluorine, chlorine, or a cyano group; and
   $R_6$ is 2,2,2-trifluoroethyl.

3. The aryl sulfide of claim 1, wherein the aryl sulfide is:

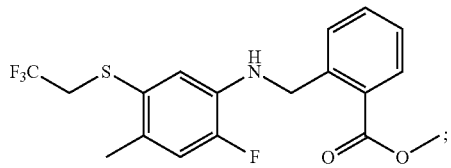

53

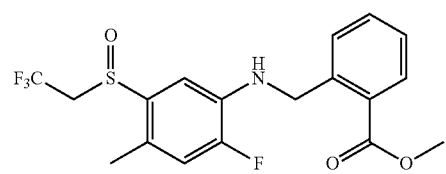

54

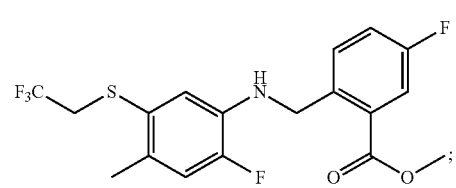

303

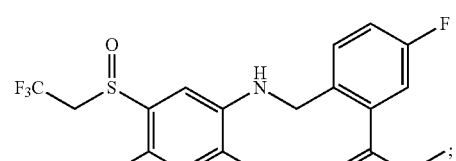

304

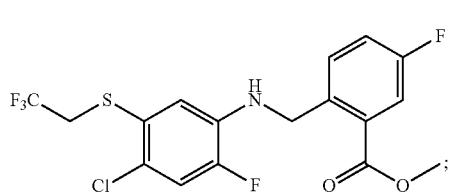

1165

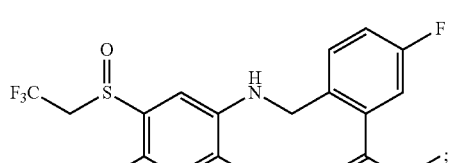

1166

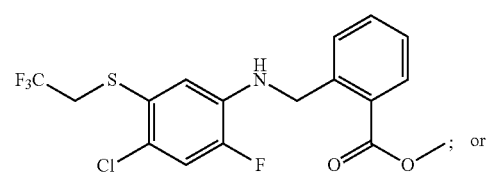

1202 or

-continued
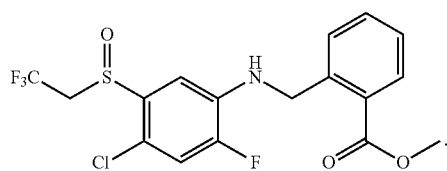
1203
* * * * *